(12) United States Patent
Robertson et al.

(10) Patent No.: US 8,858,432 B2
(45) Date of Patent: Oct. 14, 2014

(54) INGESTIBLE EVENT MARKER SYSTEMS

(75) Inventors: Timothy Robertson, Belmont, CA (US); George Savage, Portola Valley, CA (US); Mark Zdeblick, Portola Valley, CA (US); Yashar Behzadi, San Francisco, CA (US); Benedict Costello, Berkeley, CA (US); Jeremy Frank, San Francisco, CA (US); Hooman Hafezi, Redwood City, CA (US); Tariq Haniff, Redwood City, CA (US); David O'Reilly, Palo Alto, CA (US)

(73) Assignee: Proteus Digital Health, Inc., Redwood City, CA (US)

( * ) Notice: Subject to any disclaimer, the term of this patent is extended or adjusted under 35 U.S.C. 154(b) by 494 days.

(21) Appl. No.: 12/524,837

(22) PCT Filed: Feb. 1, 2008

(86) PCT No.: PCT/US2008/052845
§ 371 (c)(1),
(2), (4) Date: Mar. 19, 2010

(87) PCT Pub. No.: WO2008/095183
PCT Pub. Date: Aug. 7, 2008

(65) Prior Publication Data
US 2010/0185055 A1    Jul. 22, 2010

Related U.S. Application Data

(60) Provisional application No. 60/877,780, filed on Feb. 1, 2007, provisional application No. 60/889,871, filed
(Continued)

(51) Int. Cl.
*A61B 1/00* (2006.01)
*H04B 5/00* (2006.01)
(Continued)

(52) U.S. Cl.
CPC ............ *A61B 5/0031* (2013.01); *A61J 3/007* (2013.01); *H04B 5/0068* (2013.01);
(Continued)

(58) Field of Classification Search
USPC ................. 429/401, 405, 406, 428, 431–432, 429/523–535, 61–63, 90–93, 118–119, 429/121–122, 124–147, 163–187, 208–214, 429/219–231, 247–255; 128/920–925, 128/300–301, 309, 327, 361, 372, 101, 128/117; 600/300–301, 309, 327, 361, 372, 600/101, 117
See application file for complete search history.

(56) References Cited

U.S. PATENT DOCUMENTS 3,607,788 A    9/1971 Adolph
3,642,008 A    2/1972 Bolduc
(Continued)

FOREIGN PATENT DOCUMENTS

CN    1991868    7/2007
CN    101005470    7/2007
(Continued)

OTHER PUBLICATIONS

Jimbo, H. et al, "Gastric-fluid-utilized micro battery for micro medical devices", The Sixth International Workshop on Micro and Nanotechnology for Power Generation and Energy Conversion Applications, Nov. 29-Dec. 1, 2006, Berkeley, U.S.A, p. 97-100.*
(Continued)

*Primary Examiner* — Bill Thomson
*Assistant Examiner* — Marie Archer
(74) *Attorney, Agent, or Firm* — Bret E. Field; Bozicevic, Field & Francis LLP.

(57) ABSTRACT

Ingestible event marker systems that include an ingestible event marker (i.e., an IEM) and a personal signal receiver are provided. Embodiments of the IEM include an identifier, which may or may not be present in a physiologically acceptable carrier. The identifier is characterized by being activated upon contact with a target internal physiological site of a body, such as digestive tract internal target site. The personal signal receiver is configured to be associated with a physiological location, e.g., inside of or on the body, and to receive a signal the IEM. During use, the IEM broadcasts a signal which is received by the personal signal receiver.

25 Claims, 30 Drawing Sheets

Related U.S. Application Data on Feb. 14, 2007, provisional application No. 60/889,868, filed on Feb. 14, 2007, provisional application No. 60/949,198, filed on Jul. 11, 2007, provisional application No. 60/949,223, filed on Jul. 11, 2007, provisional application No. 60/949,208, filed on Jul. 11, 2007, provisional application No. 60/956,694, filed on Aug. 18, 2007, provisional application No. 60/941,444, filed on Jun. 1, 2007.

(51) Int. Cl.
| | | |
|---|---|---|
| *H01M 6/00* | (2006.01) | |
| *H01Q 1/27* | (2006.01) | |
| *A61B 5/07* | (2006.01) | |
| *A61B 5/00* | (2006.01) | |
| *A61J 3/00* | (2006.01) | |
| *H01Q 1/00* | (2006.01) | |
| *A61B 5/0205* | (2006.01) | |

(52) U.S. Cl.
CPC ............. *H01M 6/005* (2013.01); *H01Q 1/273* (2013.01); *A61B 5/6873* (2013.01); *A61B 5/0205* (2013.01); *A61B 5/6846* (2013.01); *A61B 5/0073* (2013.01); *A61B 5/0028* (2013.01); *A61B 2560/0214* (2013.01); *A61B 5/6861* (2013.01); *A61B 5/073* (2013.01); *Y10S 128/903* (2013.01)
USPC ........... 600/300; 600/117; 600/302; 128/903; 340/539.12; 340/573.1; 205/50; 429/400; 429/498; 429/500; 429/523; 429/63; 429/128; 429/149; 429/209; 429/122

(56) References Cited

U.S. PATENT DOCUMENTS

| | | |
|---|---|---|
| 3,679,480 A | 7/1972 | Brown et al. |
| 3,682,160 A | 8/1972 | Murata |
| 3,719,183 A | 3/1973 | Schwartz |
| 3,828,766 A | 8/1974 | Krasnow |
| 3,837,339 A | 9/1974 | Aisenberg et al. |
| 3,893,111 A | 7/1975 | Cotter |
| 3,967,202 A | 6/1976 | Batz |
| 3,989,050 A | 11/1976 | Buchalter |
| 4,017,856 A | 4/1977 | Wiegand |
| 4,055,178 A | 10/1977 | Harrigan |
| 4,077,397 A | 3/1978 | Ellis |
| 4,077,398 A | 3/1978 | Ellis |
| 4,082,087 A | 4/1978 | Howson |
| 4,090,752 A | 5/1978 | Long |
| 4,106,348 A | 8/1978 | Auphan |
| 4,129,125 A | 12/1978 | Lester |
| 4,166,453 A | 9/1979 | McClelland |
| 4,239,046 A | 12/1980 | Ong |
| 4,251,795 A | 2/1981 | Shibasaki et al. |
| 4,269,189 A | 5/1981 | Abraham |
| 4,331,654 A | 5/1982 | Morris |
| 4,345,588 A | 8/1982 | Widder et al. |
| 4,418,697 A | 12/1983 | Tama |
| 4,425,117 A | 1/1984 | Hugemann et al. |
| 4,494,950 A | 1/1985 | Fischell |
| 4,539,660 A * | 9/1985 | Miyauchi et al. ............. 365/229 |
| 4,559,950 A | 12/1985 | Vaughan |
| 4,635,641 A | 1/1987 | Hoffman |
| 4,654,165 A | 3/1987 | Eisenberg |
| 4,669,479 A | 6/1987 | Dunseath |
| 4,681,111 A | 7/1987 | Silvian |
| 4,725,997 A | 2/1988 | Urquhart et al. |
| 4,763,659 A | 8/1988 | Dunseath |
| 4,784,162 A | 11/1988 | Ricks |
| 4,793,825 A | 12/1988 | Benjamin et al. |
| 4,844,076 A | 7/1989 | Lesho |
| 4,896,261 A | 1/1990 | Nolan |
| 4,975,230 A | 12/1990 | Pinkhasov |
| 4,987,897 A | 1/1991 | Funke |
| 5,016,634 A | 5/1991 | Vock et al. |
| 5,079,006 A | 1/1992 | Urquhart |
| 5,167,626 A | 12/1992 | Casper |
| 5,176,626 A | 1/1993 | Soehendra |
| 5,261,402 A | 11/1993 | DiSabito |
| 5,263,481 A | 11/1993 | Axelgaard et al. |
| 5,279,607 A | 1/1994 | Schentag et al. |
| 5,281,287 A | 1/1994 | Lloyd |
| 5,283,136 A | 2/1994 | Peled et al. |
| 5,305,745 A | 4/1994 | Zacouto |
| 5,318,557 A | 6/1994 | Gross |
| 5,394,882 A | 3/1995 | Mawhinney |
| 5,395,366 A | 3/1995 | D'Andrea et al. |
| 5,458,141 A | 10/1995 | Neil et al. |
| 5,485,841 A | 1/1996 | Watkin et al. |
| 5,511,548 A | 4/1996 | Riazzi et al. |
| 5,596,302 A | 1/1997 | Mastrocola et al. |
| 5,600,548 A | 2/1997 | Nguyen et al. |
| 5,634,468 A | 6/1997 | Platt |
| 5,645,063 A | 7/1997 | Straka et al. |
| 5,720,771 A | 2/1998 | Snell |
| 5,740,811 A | 4/1998 | Hedberg |
| 5,757,326 A | 5/1998 | Koyama et al. |
| 5,792,048 A | 8/1998 | Schaefer |
| 5,802,467 A | 9/1998 | Salazar |
| 5,833,716 A | 11/1998 | Bar-Or |
| 5,845,265 A | 12/1998 | Woolston |
| 5,862,803 A | 1/1999 | Besson |
| 5,868,136 A | 2/1999 | Fox |
| 5,921,925 A | 7/1999 | Cartmell et al. |
| 5,925,030 A | 7/1999 | Gross et al. |
| 5,957,854 A | 9/1999 | Besson |
| 5,963,132 A | 10/1999 | Yoakum et al. |
| 5,974,124 A | 10/1999 | Schlueter, Jr. et al. |
| 5,999,846 A | 12/1999 | Pardey et al. |
| 6,023,631 A | 2/2000 | Cartmell et al. |
| 6,038,464 A | 3/2000 | Axelgaard et al. |
| 6,042,710 A | 3/2000 | Dubrow |
| 6,047,203 A | 4/2000 | Sackner |
| 6,076,016 A | 6/2000 | Feierbach |
| 6,081,734 A | 6/2000 | Batz |
| 6,083,248 A | 7/2000 | Thompson |
| 6,095,985 A | 8/2000 | Raymond et al. |
| 6,122,351 A | 9/2000 | Schlueter, Jr. et al. |
| 6,141,592 A | 10/2000 | Pauly |
| 6,200,265 B1 | 3/2001 | Walsh et al. |
| 6,204,764 B1 | 3/2001 | Maloney |
| 6,206,702 B1 | 3/2001 | Hayden et al. |
| 6,217,744 B1 | 4/2001 | Crosby |
| 6,231,593 B1 | 5/2001 | Meserol |
| 6,245,057 B1 | 6/2001 | Sieben et al. |
| 6,269,058 B1 | 7/2001 | Yamanoi et al. |
| 6,275,476 B1 | 8/2001 | Wood |
| 6,285,897 B1 | 9/2001 | Kilcoyne et al. |
| 6,287,252 B1 | 9/2001 | Lugo |
| 6,288,629 B1 | 9/2001 | Cofino et al. |
| 6,289,238 B1 | 9/2001 | Besson |
| 6,315,719 B1 | 11/2001 | Rode et al. |
| 6,358,202 B1 | 3/2002 | Arent |
| 6,364,834 B1 | 4/2002 | Reuss |
| 6,366,206 B1 | 4/2002 | Ishikawa et al. |
| 6,371,927 B1 | 4/2002 | Brune |
| 6,374,670 B1 | 4/2002 | Spelman |
| 6,380,858 B1 | 4/2002 | Yarin et al. |
| 6,394,997 B1 | 5/2002 | Lemelson |
| 6,409,674 B1 | 6/2002 | Brockway et al. |
| 6,426,863 B1 | 7/2002 | Munshi |
| 6,432,292 B1 | 8/2002 | Pinto et al. |
| 6,440,069 B1 | 8/2002 | Raymond et al. |
| 6,441,747 B1 | 8/2002 | Khair |
| 6,453,199 B1 | 9/2002 | Kobozev |
| 6,477,424 B1 | 11/2002 | Thompson et al. |
| 6,496,705 B1 | 12/2002 | Ng et al. |
| 6,526,315 B1 | 2/2003 | Inagawa |
| 6,544,174 B2 | 4/2003 | West |
| 6,564,079 B1 | 5/2003 | Cory |
| 6,577,893 B1 | 6/2003 | Besson |

(56) References Cited

U.S. PATENT DOCUMENTS

| | | |
|---|---|---|
| 6,579,231 B1 | 6/2003 | Phipps |
| 6,609,018 B2 | 8/2003 | Cory |
| 6,612,984 B1 | 9/2003 | Kerr |
| 6,632,175 B1 | 10/2003 | Marshall |
| 6,632,216 B2 | 10/2003 | Houzego et al. |
| 6,643,541 B2 | 11/2003 | Mok et al. |
| 6,654,638 B1 | 11/2003 | Sweeney |
| 6,663,846 B1 | 12/2003 | McCombs |
| 6,673,474 B2 | 1/2004 | Yamamoto |
| 6,680,923 B1 | 1/2004 | Leon |
| 6,689,117 B2 | 2/2004 | Sweeney et al. |
| 6,694,161 B2 | 2/2004 | Mehrotra |
| 6,704,602 B2 | 3/2004 | Berg et al. |
| 6,720,923 B1 | 4/2004 | Hayward et al. |
| 6,738,671 B2 | 5/2004 | Christophersom et al. |
| 6,740,033 B1 | 5/2004 | Olejniczak et al. |
| 6,745,082 B2 | 6/2004 | Axelgaard et al. |
| 6,755,783 B2 | 6/2004 | Cosentino |
| 6,757,523 B2 | 6/2004 | Fry |
| 6,800,060 B2 | 10/2004 | Marshall |
| 6,801,137 B2 | 10/2004 | Eggers et al. |
| 6,822,554 B2 | 11/2004 | Vrijens et al. |
| 6,836,862 B1 | 12/2004 | Erekson et al. |
| 6,839,659 B2 | 1/2005 | Tarassenko et al. |
| 6,840,904 B2 | 1/2005 | Goldberg |
| 6,842,636 B2 | 1/2005 | Perrault |
| 6,845,272 B1 | 1/2005 | Thomsen |
| 6,864,780 B2 | 3/2005 | Doi |
| 6,879,810 B2 | 4/2005 | Bouet |
| 6,909,878 B2 | 6/2005 | Haller |
| 6,922,592 B2 | 7/2005 | Thompson et al. |
| 6,928,370 B2 | 8/2005 | Anuzis et al. |
| 6,929,636 B1 | 8/2005 | von Alten |
| 6,937,150 B2 | 8/2005 | Medema |
| 6,942,616 B2 | 9/2005 | Kerr |
| 6,951,536 B2 | 10/2005 | Yokoi |
| 6,957,107 B2 | 10/2005 | Rogers et al. |
| 6,968,153 B1 | 11/2005 | Heinonen |
| 6,987,965 B2 | 1/2006 | Ng et al. |
| 6,990,082 B1 | 1/2006 | Zehavi et al. |
| 7,002,476 B2 | 2/2006 | Rapchak |
| 7,004,395 B2 | 2/2006 | Koenck |
| 7,009,634 B2 | 3/2006 | Iddan et al. |
| 7,009,946 B1 | 3/2006 | Kardach |
| 7,013,162 B2 | 3/2006 | Gorsuch |
| 7,016,648 B2 | 3/2006 | Haller |
| 7,020,508 B2 | 3/2006 | Stivoric |
| 7,024,248 B2 | 4/2006 | Penner et al. |
| 7,031,745 B2 | 4/2006 | Shen |
| 7,031,857 B2 | 4/2006 | Tarassenko et al. |
| 7,039,453 B2 | 5/2006 | Mullick |
| 7,046,649 B2 | 5/2006 | Awater et al. |
| 7,118,531 B2 | 10/2006 | Krill |
| 7,127,300 B2 | 10/2006 | Mazar et al. |
| 7,146,228 B2 | 12/2006 | Nielsen |
| 7,146,449 B2 | 12/2006 | Do et al. |
| 7,149,581 B2 | 12/2006 | Goedeke et al. |
| 7,154,071 B2 | 12/2006 | Sattler et al. |
| 7,155,232 B2 | 12/2006 | Godfrey et al. |
| 7,160,258 B2 | 1/2007 | Imran |
| 7,164,942 B2 | 1/2007 | Avrahami |
| 7,171,166 B2 | 1/2007 | Ng et al. |
| 7,171,177 B2 | 1/2007 | Park et al. |
| 7,171,259 B2 | 1/2007 | Rytky |
| 7,187,960 B2 | 3/2007 | Abreu |
| 7,188,767 B2 | 3/2007 | Penuela |
| 7,194,038 B1 | 3/2007 | Inkinen |
| 7,206,630 B1 | 4/2007 | Tarler |
| 7,209,790 B2 | 4/2007 | Thompson et al. |
| 7,215,660 B2 | 5/2007 | Perlman |
| 7,215,991 B2 | 5/2007 | Besson |
| 7,218,967 B2 | 5/2007 | Bergelson |
| 7,231,451 B2 | 6/2007 | Law |
| 7,243,118 B2 | 7/2007 | Lou |
| 7,246,521 B2 | 7/2007 | Kim |
| 7,249,212 B2 | 7/2007 | Do |
| 7,252,792 B2 | 8/2007 | Perrault |
| 7,253,716 B2 | 8/2007 | Lovoi et al. |
| 7,261,690 B2 | 8/2007 | Teller |
| 7,270,633 B1 | 9/2007 | Goscha |
| 7,273,454 B2 | 9/2007 | Raymond et al. |
| 7,289,855 B2 | 10/2007 | Nghiem |
| 7,291,497 B2 | 11/2007 | Holmes |
| 7,292,139 B2 | 11/2007 | Mazar et al. |
| 7,294,105 B1 | 11/2007 | Islam |
| 7,313,163 B2 | 12/2007 | Liu |
| 7,317,378 B2 | 1/2008 | Jarvis et al. |
| 7,318,808 B2 | 1/2008 | Tarassenko et al. |
| 7,336,929 B2 | 2/2008 | Yasuda |
| 7,342,895 B2 | 3/2008 | Serpa |
| 7,346,380 B2 | 3/2008 | Axelgaard et al. |
| 7,349,722 B2 | 3/2008 | Witkowski et al. |
| 7,352,998 B2 | 4/2008 | Palin |
| 7,353,258 B2 | 4/2008 | Washburn |
| 7,357,891 B2 | 4/2008 | Yang et al. |
| 7,359,674 B2 | 4/2008 | Markki |
| 7,366,558 B2 | 4/2008 | Virtanen et al. |
| 7,373,196 B2 | 5/2008 | Ryu et al. |
| 7,375,739 B2 | 5/2008 | Robbins |
| 7,376,435 B2 | 5/2008 | McGowan |
| 7,382,263 B2 | 6/2008 | Danowski et al. |
| 7,387,607 B2 | 6/2008 | Holt |
| 7,388,903 B2 | 6/2008 | Godfrey et al. |
| 7,389,088 B2 | 6/2008 | Kim |
| 7,392,015 B1 | 6/2008 | Farlow |
| 7,395,106 B2 | 7/2008 | Ryu et al. |
| 7,396,330 B2 | 7/2008 | Banet |
| 7,404,968 B2 | 7/2008 | Abrams et al. |
| 7,413,544 B2 | 8/2008 | Kerr |
| 7,414,534 B1 | 8/2008 | Kroll et al. |
| 7,414,543 B2 | 8/2008 | Rye et al. |
| 7,415,242 B1 | 8/2008 | Ngan |
| 7,424,268 B2 | 9/2008 | Diener |
| 7,424,319 B2 | 9/2008 | Muehlsteff |
| 7,427,266 B2 | 9/2008 | Ayer et al. |
| 7,471,665 B2 | 12/2008 | Perlman |
| 7,499,674 B2 | 3/2009 | Salokannel |
| 7,502,643 B2 | 3/2009 | Farringdon et al. |
| 7,510,121 B2 | 3/2009 | Koenck |
| 7,512,448 B2 | 3/2009 | Malick |
| 7,515,043 B2 | 4/2009 | Welch |
| 7,519,416 B2 | 4/2009 | Sula et al. |
| 7,523,756 B2 | 4/2009 | Minai |
| 7,525,426 B2 | 4/2009 | Edelstein |
| 7,539,533 B2 | 5/2009 | Tran |
| 7,542,878 B2 | 6/2009 | Nanikashvili |
| 7,551,590 B2 | 6/2009 | Haller |
| 7,554,452 B2 | 6/2009 | Cole |
| 7,575,005 B2 | 8/2009 | Mumford |
| 7,616,111 B2 | 11/2009 | Covannon |
| 7,617,001 B2 | 11/2009 | Penner et al. |
| 7,639,473 B2 | 12/2009 | Hsu et al. |
| 7,640,802 B2 | 1/2010 | King et al. |
| 7,647,112 B2 | 1/2010 | Tracey |
| 7,647,185 B2 | 1/2010 | Tarassenko et al. |
| 7,653,031 B2 | 1/2010 | Godfrey et al. |
| 7,672,714 B2 | 3/2010 | Kuo |
| 7,673,679 B2 | 3/2010 | Harrison et al. |
| 7,678,043 B2 | 3/2010 | Gilad |
| 7,697,994 B2 | 4/2010 | VanDanacker et al. |
| 7,720,036 B2 | 5/2010 | Sadri |
| 7,729,776 B2 | 6/2010 | Von Arx et al. |
| 7,733,224 B2 | 6/2010 | Tran |
| 7,736,318 B2 | 6/2010 | Cosentino |
| 7,756,587 B2 | 7/2010 | Penner et al. |
| 7,796,043 B2 | 9/2010 | Euliano et al. |
| 7,797,033 B2 | 9/2010 | D'Andrea et al. |
| 7,809,399 B2 | 10/2010 | Lu |
| 7,844,341 B2 | 11/2010 | Von Arx et al. |
| 7,904,133 B2 | 3/2011 | Gehman et al. |
| 8,083,128 B2 | 12/2011 | Dembo et al. |
| 8,123,576 B2 | 2/2012 | Kim |
| 8,180,425 B2 | 5/2012 | Selvitelli et al. |
| 8,200,320 B2 | 6/2012 | Kovacs |

(56) References Cited

U.S. PATENT DOCUMENTS

| | | |
|---|---|---|
| 8,214,007 B2 | 7/2012 | Baker et al. |
| 8,224,667 B1 | 7/2012 | Miller et al. |
| 8,238,998 B2 | 8/2012 | Park |
| 8,249,686 B2 | 8/2012 | Libbus et al. |
| 8,258,962 B2 | 9/2012 | Robertson et al. |
| 8,285,356 B2 | 10/2012 | Bly et al. |
| 8,290,574 B2 | 10/2012 | Felid et al. |
| 8,301,232 B2 | 10/2012 | Albert et al. |
| 8,308,640 B2 | 11/2012 | Baldus et al. |
| 8,315,687 B2 | 11/2012 | Cross et al. |
| 8,369,936 B2 | 2/2013 | Farringdon et al. |
| 8,386,009 B2 | 2/2013 | Lindberg et al. |
| 2001/0027331 A1 | 10/2001 | Thompson |
| 2001/0044588 A1 | 11/2001 | Mault |
| 2001/0051766 A1 | 12/2001 | Gazdzinski et al. |
| 2002/0002326 A1 | 1/2002 | Causey, III |
| 2002/0026111 A1 | 2/2002 | Ackerman |
| 2002/0032385 A1 | 3/2002 | Raymond et al. |
| 2002/0040278 A1 | 4/2002 | Anuzis et al. |
| 2002/0077620 A1 | 6/2002 | Sweeney et al. |
| 2002/0132226 A1* | 9/2002 | Nair et al. ................ 435/4 |
| 2002/0193669 A1 | 12/2002 | Glukhovsky |
| 2002/0193846 A1 | 12/2002 | Pool et al. |
| 2003/0017826 A1 | 1/2003 | Fishman |
| 2003/0023150 A1 | 1/2003 | Yokoi et al. |
| 2003/0028226 A1 | 2/2003 | Thompson |
| 2003/0063522 A1 | 4/2003 | Sagar |
| 2003/0065536 A1 | 4/2003 | Hansen |
| 2003/0076179 A1 | 4/2003 | Branch et al. |
| 2003/0083559 A1 | 5/2003 | Thompson |
| 2003/0126593 A1 | 7/2003 | Mault |
| 2003/0130714 A1 | 7/2003 | Nielsen et al. |
| 2003/0135128 A1 | 7/2003 | Suffin et al. |
| 2003/0135392 A1 | 7/2003 | Vrijens et al. |
| 2003/0152622 A1 | 8/2003 | Louie-Helm et al. |
| 2003/0158466 A1 | 8/2003 | Lynn et al. |
| 2003/0158756 A1 | 8/2003 | Abramson |
| 2003/0162556 A1 | 8/2003 | Libes |
| 2003/0167000 A1 | 9/2003 | Mullick et al. |
| 2003/0171791 A1 | 9/2003 | KenKnight |
| 2003/0171898 A1 | 9/2003 | Tarassenko et al. |
| 2003/0181788 A1 | 9/2003 | Yokoi et al. |
| 2003/0181815 A1 | 9/2003 | Ebner et al. |
| 2003/0185286 A1 | 10/2003 | Yuen |
| 2003/0187337 A1 | 10/2003 | Tarassenko et al. |
| 2003/0187338 A1 | 10/2003 | Say et al. |
| 2003/0195403 A1 | 10/2003 | Berner et al. |
| 2003/0213495 A1 | 11/2003 | Fujita et al. |
| 2003/0214579 A1 | 11/2003 | Iddan |
| 2003/0216622 A1 | 11/2003 | Meron et al. |
| 2003/0216625 A1 | 11/2003 | Phipps |
| 2003/0216666 A1 | 11/2003 | Ericson et al. |
| 2003/0216729 A1 | 11/2003 | Marchitto |
| 2004/0008123 A1 | 1/2004 | Carrender et al. |
| 2004/0018476 A1 | 1/2004 | LaDue |
| 2004/0019172 A1 | 1/2004 | Yang et al. |
| 2004/0034295 A1 | 2/2004 | Salganicoff |
| 2004/0049245 A1 | 3/2004 | Gass |
| 2004/0073095 A1 | 4/2004 | Causey et al. |
| 2004/0073454 A1 | 4/2004 | Urquhart et al. |
| 2004/0077995 A1 | 4/2004 | Ferek-Petric |
| 2004/0082982 A1 | 4/2004 | Gord et al. |
| 2004/0087839 A1 | 5/2004 | Raymond et al. |
| 2004/0092801 A1 | 5/2004 | Drakulic |
| 2004/0106859 A1 | 6/2004 | Say et al. |
| 2004/0111011 A1 | 6/2004 | Uchiyama et al. |
| 2004/0115517 A1 | 6/2004 | Fukuda et al. |
| 2004/0121015 A1 | 6/2004 | Chidlaw et al. |
| 2004/0148140 A1 | 7/2004 | Tarassenko et al. |
| 2004/0153007 A1 | 8/2004 | Harris |
| 2004/0167226 A1 | 8/2004 | Serafini |
| 2004/0167801 A1 | 8/2004 | Say et al. |
| 2004/0171914 A1 | 9/2004 | Avni |
| 2004/0193020 A1 | 9/2004 | Chiba |
| 2004/0193029 A1 | 9/2004 | Glukhovsky |
| 2004/0193446 A1 | 9/2004 | Mayer et al. |
| 2004/0199222 A1 | 10/2004 | Sun et al. |
| 2004/0215084 A1 | 10/2004 | Shimizu et al. |
| 2004/0218683 A1 | 11/2004 | Batra |
| 2004/0220643 A1 | 11/2004 | Schmidt |
| 2004/0224644 A1 | 11/2004 | Wu |
| 2004/0225199 A1 | 11/2004 | Evanyk |
| 2004/0253304 A1 | 12/2004 | Gross et al. |
| 2004/0260154 A1 | 12/2004 | Sidelnik |
| 2005/0017841 A1 | 1/2005 | Doi |
| 2005/0020887 A1 | 1/2005 | Goldberg |
| 2005/0021370 A1 | 1/2005 | Riff |
| 2005/0024198 A1 | 2/2005 | Ward |
| 2005/0027205 A1 | 2/2005 | Tarassenko et al. |
| 2005/0038321 A1 | 2/2005 | Fujita et al. |
| 2005/0043634 A1 | 2/2005 | Yokoi et al. |
| 2005/0054897 A1 | 3/2005 | Hashimoto et al. |
| 2005/0062644 A1 | 3/2005 | Leci |
| 2005/0065407 A1 | 3/2005 | Nakamura et al. |
| 2005/0070778 A1 | 3/2005 | Lackey |
| 2005/0092108 A1 | 5/2005 | Andermo |
| 2005/0096514 A1 | 5/2005 | Starkebaum |
| 2005/0096562 A1 | 5/2005 | Delalic et al. |
| 2005/0101843 A1 | 5/2005 | Quinn |
| 2005/0101872 A1 | 5/2005 | Sattler |
| 2005/0115561 A1 | 6/2005 | Stahmann et al. |
| 2005/0116820 A1 | 6/2005 | Goldreich |
| 2005/0117389 A1 | 6/2005 | Worledge |
| 2005/0121322 A1 | 6/2005 | Say et al. |
| 2005/0131281 A1 | 6/2005 | Ayer et al. |
| 2005/0137480 A1 | 6/2005 | Alt et al. |
| 2005/0143623 A1 | 6/2005 | Kojima |
| 2005/0148883 A1 | 7/2005 | Boesen |
| 2005/0151625 A1 | 7/2005 | Lai |
| 2005/0154428 A1 | 7/2005 | Bruinsma |
| 2005/0165323 A1 | 7/2005 | Montgomery |
| 2005/0177069 A1 | 8/2005 | Takizawa |
| 2005/0182389 A1 | 8/2005 | LaPorte |
| 2005/0187789 A1 | 8/2005 | Hatlestad et al. |
| 2005/0192489 A1 | 9/2005 | Marshall |
| 2005/0197680 A1 | 9/2005 | DelMain et al. |
| 2005/0228268 A1 | 10/2005 | Cole |
| 2005/0234307 A1 | 10/2005 | Heinonen |
| 2005/0240305 A1 | 10/2005 | Bogash et al. |
| 2005/0245794 A1 | 11/2005 | Dinsmoor |
| 2005/0259768 A1 | 11/2005 | Yang et al. |
| 2005/0261559 A1 | 11/2005 | Mumford et al. |
| 2005/0267556 A1 | 12/2005 | Shuros et al. |
| 2005/0267756 A1 | 12/2005 | Schultz et al. |
| 2005/0277912 A1 | 12/2005 | John |
| 2005/0277999 A1 | 12/2005 | Strother et al. |
| 2005/0285746 A1 | 12/2005 | Sengupta |
| 2005/0288594 A1 | 12/2005 | Lewkowicz et al. |
| 2006/0001496 A1 | 1/2006 | Abrosimov et al. |
| 2006/0036134 A1 | 2/2006 | Tarassenko et al. |
| 2006/0061472 A1 | 3/2006 | Lovoi et al. |
| 2006/0065713 A1 | 3/2006 | Kingery |
| 2006/0074283 A1 | 4/2006 | Henderson |
| 2006/0078765 A1 | 4/2006 | Yang et al. |
| 2006/0095091 A1 | 5/2006 | Drew |
| 2006/0095093 A1 | 5/2006 | Bettesh et al. |
| 2006/0100533 A1 | 5/2006 | Han |
| 2006/0109058 A1 | 5/2006 | Keating |
| 2006/0110962 A1 | 5/2006 | Powell |
| 2006/0122667 A1 | 6/2006 | Chavan et al. |
| 2006/0136266 A1 | 6/2006 | Tarassenko et al. |
| 2006/0142648 A1 | 6/2006 | Banet |
| 2006/0145876 A1 | 7/2006 | Kimura |
| 2006/0148254 A1 | 7/2006 | McLean |
| 2006/0149339 A1 | 7/2006 | Burnes |
| 2006/0155174 A1 | 7/2006 | Glukhovsky et al. |
| 2006/0155183 A1 | 7/2006 | Kroecker |
| 2006/0158820 A1 | 7/2006 | Takiguchi |
| 2006/0161225 A1 | 7/2006 | Sormann et al. |
| 2006/0179949 A1 | 8/2006 | Kim |
| 2006/0183992 A1 | 8/2006 | Kawashima |
| 2006/0183993 A1 | 8/2006 | Horn |
| 2006/0184092 A1 | 8/2006 | Atanasoska et al. |
| 2006/0204738 A1 | 9/2006 | Dubrow et al. |

(56) References Cited

U.S. PATENT DOCUMENTS

| | | |
|---|---|---|
| 2006/0210626 A1 | 9/2006 | Spaeder |
| 2006/0216603 A1 | 9/2006 | Choi |
| 2006/0218011 A1 | 9/2006 | Walker |
| 2006/0229053 A1 | 10/2006 | Sivard |
| 2006/0235489 A1 | 10/2006 | Drew |
| 2006/0247505 A1 | 11/2006 | Siddiqui |
| 2006/0253005 A1 | 11/2006 | Drinan |
| 2006/0265246 A1 | 11/2006 | Hoag |
| 2006/0270346 A1 | 11/2006 | Ibrahim et al. |
| 2006/0273882 A1 | 12/2006 | Posamentier |
| 2006/0280227 A1 | 12/2006 | Pinkney |
| 2006/0282001 A1 | 12/2006 | Noel |
| 2006/0289640 A1 | 12/2006 | Mercure |
| 2006/0293607 A1 | 12/2006 | Alt |
| 2007/0002038 A1 | 1/2007 | Suzuki |
| 2007/0006636 A1 | 1/2007 | King et al. |
| 2007/0008113 A1 | 1/2007 | Spoonhower et al. |
| 2007/0016089 A1 | 1/2007 | Fischell et al. |
| 2007/0027386 A1 | 2/2007 | Such |
| 2007/0027388 A1 | 2/2007 | Chou |
| 2007/0038054 A1 | 2/2007 | Zhou |
| 2007/0049339 A1 | 3/2007 | Barak et al. |
| 2007/0055098 A1 | 3/2007 | Shimizu et al. |
| 2007/0060797 A1 | 3/2007 | Ball |
| 2007/0073353 A1 | 3/2007 | Rooney et al. |
| 2007/0096765 A1 | 5/2007 | Kagan |
| 2007/0106346 A1 | 5/2007 | Bergelson |
| 2007/0123772 A1 | 5/2007 | Euliano |
| 2007/0129622 A1 | 6/2007 | Bourget |
| 2007/0130287 A1 | 6/2007 | Kumar |
| 2007/0135691 A1 | 6/2007 | Zingelewicz et al. |
| 2007/0135803 A1 | 6/2007 | Belson |
| 2007/0142721 A1 | 6/2007 | Berner et al. |
| 2007/0156016 A1 | 7/2007 | Betesh |
| 2007/0162089 A1 | 7/2007 | Mosesov |
| 2007/0162090 A1 | 7/2007 | Penner |
| 2007/0167495 A1 | 7/2007 | Brown et al. |
| 2007/0167848 A1 | 7/2007 | Kuo et al. |
| 2007/0173701 A1 | 7/2007 | Al-Ali |
| 2007/0179347 A1 | 8/2007 | Tarassenko et al. |
| 2007/0185393 A1 | 8/2007 | Zhou |
| 2007/0191002 A1 | 8/2007 | Ge |
| 2007/0196456 A1 | 8/2007 | Stevens |
| 2007/0207793 A1 | 9/2007 | Myer |
| 2007/0207858 A1 | 9/2007 | Breving |
| 2007/0208233 A1 | 9/2007 | Kovacs |
| 2007/0213659 A1 | 9/2007 | Trovato et al. |
| 2007/0237719 A1 | 10/2007 | Jones |
| 2007/0244370 A1 | 10/2007 | Kuo et al. |
| 2007/0255198 A1 | 11/2007 | Leong et al. |
| 2007/0255330 A1 | 11/2007 | Lee |
| 2007/0270672 A1 | 11/2007 | Hayter |
| 2007/0279217 A1 | 12/2007 | Venkatraman |
| 2007/0282174 A1 | 12/2007 | Sabatino |
| 2007/0282177 A1 | 12/2007 | Pilz |
| 2007/0299480 A1 | 12/2007 | Hill |
| 2008/0014866 A1 | 1/2008 | Lipowski |
| 2008/0015421 A1 | 1/2008 | Penner |
| 2008/0020037 A1 | 1/2008 | Robertson et al. |
| 2008/0021519 A1 | 1/2008 | DeGeest |
| 2008/0021521 A1 | 1/2008 | Shah |
| 2008/0027679 A1 | 1/2008 | Shklarski |
| 2008/0033273 A1 | 2/2008 | Zhou |
| 2008/0039700 A1 | 2/2008 | Drinan et al. |
| 2008/0046038 A1 | 2/2008 | Hill |
| 2008/0051667 A1 | 2/2008 | Goldreich |
| 2008/0051767 A1 | 2/2008 | Rossing et al. |
| 2008/0058614 A1 | 3/2008 | Banet |
| 2008/0062856 A1 | 3/2008 | Feher |
| 2008/0065168 A1 | 3/2008 | Bitton et al. |
| 2008/0074307 A1 | 3/2008 | Boric-Lubecke |
| 2008/0077015 A1 | 3/2008 | Boric-Lubecke |
| 2008/0077028 A1 | 3/2008 | Schaldach et al. |
| 2008/0077188 A1 | 3/2008 | Denker et al. |
| 2008/0091089 A1 | 4/2008 | Guillory et al. |
| 2008/0091114 A1 | 4/2008 | Min |
| 2008/0097549 A1 | 4/2008 | Colbaugh |
| 2008/0097917 A1 | 4/2008 | Dicks |
| 2008/0103440 A1 | 5/2008 | Ferren et al. |
| 2008/0114224 A1 | 5/2008 | Bandy et al. |
| 2008/0119705 A1 | 5/2008 | Patel |
| 2008/0119716 A1 | 5/2008 | Boric-Lubecke |
| 2008/0137566 A1 | 6/2008 | Marholev |
| 2008/0140403 A1 | 6/2008 | Hughes et al. |
| 2008/0146871 A1 | 6/2008 | Arneson et al. |
| 2008/0146889 A1 | 6/2008 | Young |
| 2008/0146892 A1 | 6/2008 | LeBoeuf |
| 2008/0154104 A1 | 6/2008 | Lamego |
| 2008/0166992 A1 | 7/2008 | Ricordi |
| 2008/0183245 A1 | 7/2008 | Van Oort |
| 2008/0188837 A1 | 8/2008 | Belsky et al. |
| 2008/0194912 A1 | 8/2008 | Trovato et al. |
| 2008/0208009 A1 | 8/2008 | Shklarski |
| 2008/0214901 A1 | 9/2008 | Gehman |
| 2008/0214985 A1 | 9/2008 | Yanaki |
| 2008/0243020 A1 | 10/2008 | Chou |
| 2008/0249360 A1 | 10/2008 | Li |
| 2008/0262320 A1 | 10/2008 | Schaefer et al. |
| 2008/0262336 A1 | 10/2008 | Ryu |
| 2008/0269664 A1 | 10/2008 | Trovato et al. |
| 2008/0275312 A1 | 11/2008 | Mosesov |
| 2008/0281636 A1 | 11/2008 | Jung et al. |
| 2008/0284599 A1 | 11/2008 | Zdeblick et al. |
| 2008/0288026 A1 | 11/2008 | Cross et al. |
| 2008/0288027 A1 | 11/2008 | Kroll |
| 2008/0294020 A1 | 11/2008 | Sapounas |
| 2008/0300572 A1 | 12/2008 | Rankers |
| 2008/0303638 A1 | 12/2008 | Nguyen |
| 2008/0306357 A1 | 12/2008 | Korman |
| 2008/0306359 A1 | 12/2008 | Zdeblick et al. |
| 2008/0306360 A1 | 12/2008 | Robertson et al. |
| 2008/0311852 A1 | 12/2008 | Hansen |
| 2008/0312522 A1 | 12/2008 | Rowlandson |
| 2008/0316020 A1 | 12/2008 | Robertson |
| 2009/0009332 A1 | 1/2009 | Nunez et al. |
| 2009/0024045 A1 | 1/2009 | Prakash |
| 2009/0030293 A1 | 1/2009 | Cooper et al. |
| 2009/0030297 A1 | 1/2009 | Miller |
| 2009/0034209 A1 | 2/2009 | Joo |
| 2009/0043171 A1 | 2/2009 | Rule |
| 2009/0048498 A1 | 2/2009 | Riskey |
| 2009/0062634 A1 | 3/2009 | Say et al. |
| 2009/0062670 A1 | 3/2009 | Sterling |
| 2009/0069642 A1 | 3/2009 | Gao |
| 2009/0069655 A1 | 3/2009 | Say et al. |
| 2009/0069656 A1 | 3/2009 | Say et al. |
| 2009/0069657 A1 | 3/2009 | Say et al. |
| 2009/0069658 A1 | 3/2009 | Say et al. |
| 2009/0076340 A1 | 3/2009 | Libbus et al. |
| 2009/0076343 A1 | 3/2009 | James |
| 2009/0076397 A1 | 3/2009 | Libbus et al. |
| 2009/0082645 A1 | 3/2009 | Hafezi et al. |
| 2009/0088618 A1 | 4/2009 | Arneson |
| 2009/0099435 A1 | 4/2009 | Say et al. |
| 2009/0105561 A1 | 4/2009 | Boyden et al. |
| 2009/0110148 A1 | 4/2009 | Zhang |
| 2009/0112626 A1 | 4/2009 | Talbot |
| 2009/0124871 A1 | 5/2009 | Arshak |
| 2009/0131774 A1 | 5/2009 | Sweitzer |
| 2009/0135886 A1 | 5/2009 | Robertson et al. |
| 2009/0157113 A1 | 6/2009 | Marcotte |
| 2009/0157358 A1 | 6/2009 | Kim |
| 2009/0161602 A1 | 6/2009 | Matsumoto |
| 2009/0163789 A1 | 6/2009 | Say et al. |
| 2009/0171180 A1 | 7/2009 | Pering |
| 2009/0173628 A1 | 7/2009 | Say et al. |
| 2009/0177055 A1 | 7/2009 | Say et al. |
| 2009/0177056 A1 | 7/2009 | Say et al. |
| 2009/0177057 A1 | 7/2009 | Say et al. |
| 2009/0177058 A1 | 7/2009 | Say et al. |
| 2009/0177059 A1 | 7/2009 | Say et al. |
| 2009/0177060 A1 | 7/2009 | Say et al. |
| 2009/0177061 A1 | 7/2009 | Say et al. |
| 2009/0177062 A1 | 7/2009 | Say et al. |

(56) References Cited

U.S. PATENT DOCUMENTS

| | | |
|---|---|---|
| 2009/0177063 A1 | 7/2009 | Say et al. |
| 2009/0177064 A1 | 7/2009 | Say et al. |
| 2009/0177065 A1 | 7/2009 | Say et al. |
| 2009/0177066 A1 | 7/2009 | Say et al. |
| 2009/0182206 A1 | 7/2009 | Najafi |
| 2009/0182212 A1 | 7/2009 | Say et al. |
| 2009/0182213 A1 | 7/2009 | Say et al. |
| 2009/0182214 A1 | 7/2009 | Say et al. |
| 2009/0182215 A1 | 7/2009 | Say et al. |
| 2009/0182388 A1 | 7/2009 | Von Arx |
| 2009/0187088 A1 | 7/2009 | Say et al. |
| 2009/0187089 A1 | 7/2009 | Say et al. |
| 2009/0187090 A1 | 7/2009 | Say et al. |
| 2009/0187091 A1 | 7/2009 | Say et al. |
| 2009/0187092 A1 | 7/2009 | Say et al. |
| 2009/0187093 A1 | 7/2009 | Say et al. |
| 2009/0187094 A1 | 7/2009 | Say et al. |
| 2009/0187095 A1 | 7/2009 | Say et al. |
| 2009/0187381 A1 | 7/2009 | King et al. |
| 2009/0192351 A1 | 7/2009 | Nishino |
| 2009/0192368 A1 | 7/2009 | Say et al. |
| 2009/0192369 A1 | 7/2009 | Say et al. |
| 2009/0192370 A1 | 7/2009 | Say et al. |
| 2009/0192371 A1 | 7/2009 | Say et al. |
| 2009/0192372 A1 | 7/2009 | Say et al. |
| 2009/0192373 A1 | 7/2009 | Say et al. |
| 2009/0192374 A1 | 7/2009 | Say et al. |
| 2009/0192375 A1 | 7/2009 | Say et al. |
| 2009/0192376 A1 | 7/2009 | Say et al. |
| 2009/0192377 A1 | 7/2009 | Say et al. |
| 2009/0192378 A1 | 7/2009 | Say et al. |
| 2009/0192379 A1 | 7/2009 | Say et al. |
| 2009/0198115 A1 | 8/2009 | Say et al. |
| 2009/0198116 A1 | 8/2009 | Say et al. |
| 2009/0198175 A1 | 8/2009 | Say et al. |
| 2009/0203964 A1 | 8/2009 | Shimizu et al. |
| 2009/0203971 A1 | 8/2009 | Sciarappa |
| 2009/0203972 A1 | 8/2009 | Heneghan |
| 2009/0203978 A1 | 8/2009 | Say et al. |
| 2009/0204265 A1 | 8/2009 | Hackett |
| 2009/0210164 A1 | 8/2009 | Say et al. |
| 2009/0216101 A1 | 8/2009 | Say et al. |
| 2009/0216102 A1 | 8/2009 | Say et al. |
| 2009/0227204 A1 | 9/2009 | Robertson et al. |
| 2009/0227876 A1 | 9/2009 | Tran |
| 2009/0227940 A1 | 9/2009 | Say et al. |
| 2009/0227941 A1 | 9/2009 | Say et al. |
| 2009/0228214 A1 | 9/2009 | Say et al. |
| 2009/0231125 A1 | 9/2009 | Baldus |
| 2009/0234200 A1 | 9/2009 | Husheer |
| 2009/0243833 A1 | 10/2009 | Huang |
| 2009/0253960 A1 | 10/2009 | Takenaka et al. |
| 2009/0256702 A1 | 10/2009 | Robertson |
| 2009/0264714 A1 | 10/2009 | Chou |
| 2009/0264964 A1 | 10/2009 | Abrahamson |
| 2009/0265186 A1 | 10/2009 | Tarassenko et al. |
| 2009/0273467 A1 | 11/2009 | Elixmann |
| 2009/0281539 A1 | 11/2009 | Selig |
| 2009/0292194 A1 | 11/2009 | Libbus et al. |
| 2009/0295548 A1 | 12/2009 | Ronkka |
| 2009/0296677 A1 | 12/2009 | Mahany |
| 2009/0303920 A1 | 12/2009 | Mahany |
| 2009/0312619 A1 | 12/2009 | Say et al. |
| 2009/0318761 A1 | 12/2009 | Rabinovitz |
| 2009/0318779 A1 | 12/2009 | Tran |
| 2009/0318783 A1 | 12/2009 | Rohde et al. |
| 2009/0318793 A1 | 12/2009 | Datta |
| 2010/0006585 A1 | 1/2010 | Flowers et al. |
| 2010/0010330 A1 | 1/2010 | Rankers |
| 2010/0049006 A1 | 2/2010 | Magar |
| 2010/0049012 A1 | 2/2010 | Dijksman et al. |
| 2010/0049069 A1 | 2/2010 | Tarassenko et al. |
| 2010/0056878 A1 | 3/2010 | Partin |
| 2010/0056891 A1 | 3/2010 | Say et al. |
| 2010/0056939 A1 | 3/2010 | Tarassenko et al. |
| 2010/0057041 A1 | 3/2010 | Hayter |
| 2010/0062709 A1 | 3/2010 | Kato |
| 2010/0063438 A1 | 3/2010 | Bengtsson |
| 2010/0063841 A1 | 3/2010 | D'Ambrosia et al. |
| 2010/0069002 A1 | 3/2010 | Rong |
| 2010/0069717 A1 | 3/2010 | Hafezi et al. |
| 2010/0099967 A1 | 4/2010 | Say et al. |
| 2010/0099968 A1 | 4/2010 | Say et al. |
| 2010/0099969 A1 | 4/2010 | Say et al. |
| 2010/0100077 A1 | 4/2010 | Rush |
| 2010/0100078 A1 | 4/2010 | Say et al. |
| 2010/0106001 A1 | 4/2010 | Say et al. |
| 2010/0118853 A1 | 5/2010 | Godfrey |
| 2010/0139672 A1 | 6/2010 | Kroll et al. |
| 2010/0160742 A1 | 6/2010 | Seidl et al. |
| 2010/0168659 A1 | 7/2010 | Say et al. |
| 2010/0179398 A1 | 7/2010 | Say et al. |
| 2010/0185055 A1 | 7/2010 | Robertson et al. |
| 2010/0191073 A1 | 7/2010 | Tarassenko et al. |
| 2010/0210299 A1 | 8/2010 | Gorbachov |
| 2010/0222652 A1 | 9/2010 | Cho |
| 2010/0228113 A1 | 9/2010 | Solosko |
| 2010/0234706 A1 | 9/2010 | Gilland |
| 2010/0234715 A1 | 9/2010 | Shin |
| 2010/0234914 A1 | 9/2010 | Shen |
| 2010/0245091 A1 | 9/2010 | Singh |
| 2010/0249881 A1 | 9/2010 | Corndorf |
| 2010/0256461 A1 | 10/2010 | Mohamedali |
| 2010/0259543 A1 | 10/2010 | Tarassenko et al. |
| 2010/0268048 A1 | 10/2010 | Say et al. |
| 2010/0268049 A1 | 10/2010 | Say et al. |
| 2010/0268050 A1 | 10/2010 | Say et al. |
| 2010/0274111 A1 | 10/2010 | Say et al. |
| 2010/0280345 A1 | 11/2010 | Say et al. |
| 2010/0280346 A1 | 11/2010 | Say et al. |
| 2010/0295694 A1 | 11/2010 | Kauffman et al. |
| 2010/0298730 A1 | 11/2010 | Tarassenko et al. |
| 2010/0299155 A1 | 11/2010 | Findlay et al. |
| 2010/0312188 A1 | 12/2010 | Robertson et al. |
| 2010/0312580 A1 | 12/2010 | Tarassenko et al. |
| 2010/0332443 A1 | 12/2010 | Gartenberg |
| 2011/0009715 A1 | 1/2011 | O'Reilly et al. |
| 2011/0040203 A1 | 2/2011 | Savage et al. |
| 2011/0050431 A1 | 3/2011 | Hood et al. |
| 2011/0054265 A1 | 3/2011 | Hafezi et al. |
| 2011/0144470 A1 | 6/2011 | Mazar et al. |
| 2011/0279963 A1 | 11/2011 | Kumar et al. |
| 2012/0029309 A1 | 2/2012 | Paquet et al. |
| 2012/0101396 A1 | 4/2012 | Solosko et al. |
| 2012/0197144 A1 | 8/2012 | Christ et al. |
| 2012/0265544 A1 | 10/2012 | Hwang et al. |
| 2012/0310070 A1 | 12/2012 | Kumar et al. |
| 2012/0316413 A1 | 12/2012 | Liu et al. |
| 2013/0030259 A1 | 1/2013 | Thomsen et al. |
| 2013/0060115 A1 | 3/2013 | Gehman et al. |

FOREIGN PATENT DOCUMENTS

| | | |
|---|---|---|
| CN | 201076456 | 6/2008 |
| EP | 0344939 | 12/1989 |
| EP | 1246356 | 10/2002 |
| EP | 1534054 | 5/2005 |
| EP | 1702553 | 9/2006 |
| EP | 1789128 | 5/2007 |
| EP | 2143369 | 1/2010 |
| GB | 2432862 | 6/2007 |
| IL | 172917 | 6/2010 |
| JP | 61017949 | 1/1986 |
| JP | 61072712 | 4/1986 |
| JP | 05-228128 | 9/1993 |
| JP | 10-14898 | 1/1998 |
| JP | 2000-506410 | 5/2000 |
| JP | 2002-224053 | 8/2002 |
| JP | 2002263185 | 9/2002 |
| JP | 2002291684 | 10/2002 |
| JP | 2004-7187 | 1/2004 |
| JP | 2004134384 | 4/2004 |
| JP | 2005-073886 | 3/2005 |
| JP | 2005-304880 | 4/2005 |

(56) References Cited

FOREIGN PATENT DOCUMENTS

| | | |
|---|---|---|
| JP | 2005-532841 | 11/2005 |
| JP | 2005-532849 | 11/2005 |
| JP | 2006006377 | 1/2006 |
| JP | 2006509574 | 3/2006 |
| JP | 2006-177699 | 7/2006 |
| JP | 2006-187611 | 7/2006 |
| JP | 2006278091 | 10/2006 |
| JP | 2007-313340 | 12/2007 |
| JP | 2009-061236 | 3/2009 |
| KR | 20020015907 | 3/2002 |
| KR | 20020061744 | 7/2002 |
| KR | 200609977523 | 7/2006 |
| KR | 927471 | 11/2009 |
| TW | 553735 | 9/2003 |
| TW | 200724094 | 7/2007 |
| WO | 8802237 | 4/1988 |
| WO | WO8802237 | 4/1988 |
| WO | WO9308734 | 5/1993 |
| WO | WO9319667 | 10/1993 |
| WO | WO9739963 | 10/1997 |
| WO | WO9843537 | 10/1998 |
| WO | WO9959465 | 11/1999 |
| WO | WO0033246 | 6/2000 |
| WO | WO0100085 | 1/2001 |
| WO | 01/47466 | 7/2001 |
| WO | WO0149364 | 7/2001 |
| WO | WO0174011 | 10/2001 |
| WO | WO0180731 | 11/2001 |
| WO | WO0245489 | 6/2002 |
| WO | WO02058330 | 7/2002 |
| WO | WO02062276 | 8/2002 |
| WO | WO02087681 | 11/2002 |
| WO | WO03050643 | 6/2003 |
| WO | WO2004014225 | 2/2004 |
| WO | WO2004039256 | 5/2004 |
| WO | WO2004066834 | 8/2004 |
| WO | WO2004066903 | 8/2004 |
| WO | WO2004068748 | 8/2004 |
| WO | WO2004068881 | 8/2004 |
| WO | WO2004075751 | 9/2004 |
| WO | WO2004109316 | 12/2004 |
| WO | WO2005011237 | 2/2005 |
| WO | 2005/020023 | 3/2005 |
| WO | 2006/055892 | 3/2005 |
| WO | WO2005024687 | 3/2005 |
| WO | WO2005047837 | 5/2005 |
| WO | WO2005051166 | 6/2005 |
| WO | WO2005082436 | 9/2005 |
| WO | WO2005110238 | 11/2005 |
| WO | WO2006027586 | 3/2006 |
| WO | WO2006035351 | 4/2006 |
| WO | 2006/055956 | 5/2006 |
| WO | 2006/104843 | 5/2006 |
| WO | WO2006075016 | 7/2006 |
| WO | WO2006100620 | 9/2006 |
| WO | WO2006109072 | 10/2006 |
| WO | 2006/116718 | 11/2006 |
| WO | 2006/127355 | 11/2006 |
| WO | WO2006119345 | 11/2006 |
| WO | 2007/001724 | 1/2007 |
| WO | 2007/001742 | 1/2007 |
| WO | 2007/013952 | 2/2007 |
| WO | 2007/014084 | 2/2007 |
| WO | 2007/021496 | 2/2007 |
| WO | WO2007014527 | 2/2007 |
| WO | 2007/027660 | 3/2007 |
| WO | 2007/028035 | 3/2007 |
| WO | WO2007028035 | 3/2007 |
| WO | 2007036741 | 4/2007 |
| WO | 2007036746 | 4/2007 |
| WO | WO2007036687 | 4/2007 |
| WO | WO2007036741 | 4/2007 |
| WO | WO2007036746 | 4/2007 |
| WO | WO2007040878 | 4/2007 |
| WO | WO2007067054 | 6/2007 |
| WO | WO2007071180 | 6/2007 |
| WO | WO2007096810 | 8/2007 |
| WO | WO2007101141 | 9/2007 |
| WO | WO2007120946 | 10/2007 |
| WO | 2007130491 | 11/2007 |
| WO | WO2007127316 | 11/2007 |
| WO | WO2007127879 | 11/2007 |
| WO | WO2007127945 | 11/2007 |
| WO | WO2007128165 | 11/2007 |
| WO | WO2007133526 | 11/2007 |
| WO | 2007/149546 | 12/2007 |
| WO | WO2007143535 | 12/2007 |
| WO | 2008/008281 | 1/2008 |
| WO | WO2008030482 | 3/2008 |
| WO | 2008/052136 | 5/2008 |
| WO | 2008/063626 | 5/2008 |
| WO | 2008/066617 | 6/2008 |
| WO | WO2008076464 | 6/2008 |
| WO | WO2008089232 | 7/2008 |
| WO | WO2008091683 | 7/2008 |
| WO | 2008/095183 | 8/2008 |
| WO | 2008/101107 | 8/2008 |
| WO | WO2008097652 | 8/2008 |
| WO | 2008/112577 | 9/2008 |
| WO | 2008/112578 | 9/2008 |
| WO | 2008/120156 | 10/2008 |
| WO | WO2008133394 | 11/2008 |
| WO | WO2008134185 | 11/2008 |
| WO | 2009001108 | 12/2008 |
| WO | WO2008150633 | 12/2008 |
| WO | WO2009001108 | 12/2008 |
| WO | WO2009006615 | 1/2009 |
| WO | WO2009029453 | 3/2009 |
| WO | WO2009036334 | 3/2009 |
| WO | WO2009051829 | 4/2009 |
| WO | WO2009051830 | 4/2009 |
| WO | WO2009063377 | 5/2009 |
| WO | WO2009081348 | 7/2009 |
| WO | WO2009111664 | 9/2009 |
| WO | WO2009146082 | 12/2009 |
| WO | WO2010000085 | 1/2010 |
| WO | WO2010009100 | 1/2010 |
| WO | WO2010011833 | 1/2010 |
| WO | 2010019778 | 2/2010 |
| WO | 2010057049 | 5/2010 |
| WO | WO2010080765 | 7/2010 |
| WO | WO2010080843 | 7/2010 |
| WO | WO2010107563 | 9/2010 |
| WO | WO2010132331 | 11/2010 |
| WO | WO2010135516 | 11/2010 |
| WO | WO2011068963 | 6/2011 |
| WO | WO2011133799 | 10/2011 |
| WO | WO2011159336 | 12/2011 |
| WO | WO2011159337 | 12/2011 |
| WO | WO2011159338 | 12/2011 |
| WO | WO2011159339 | 12/2011 |
| WO | WO2012104657 | 8/2012 |
| WO | WO2012158190 | 11/2012 |

OTHER PUBLICATIONS

Gilson, D.R. "Molecular dynamics simulation of dipole interactions", Department of Physics, Hull University, Dec. 2002, p. 1-43.
Li, P-Y, et al. "An electrochemical intraocular drug delivery device", Sensors and Actuators A 143 (2008) p. 41-48.
NPL_AntennaBasics.pdf, p. 1-3.
Santini, J.T. et al, "Microchips as controlled drug delivery-devices", Agnew. Chem. Int. Ed. 2000, vol. 39, p. 2396-2407.
Shawgo, R.S. et al. "BioMEMS from drug delivery", Current Opinion in Solid State and Material Science 6 (2002), p. 329-334.
Soper, S.A. et al. "Bio-Mems Technologies and Applications", Chapter 12, "MEMS for Drug Delivery", p. 325-346.
Tierney, M.J. et al "Electroreleasing Composite Membranes for Delivery of Insulin and other Biomacromolecules", J. Electrochem. Soc., vol. 137, No. 6, Jun. 1990, p. 2005-2006.
Description of ePatch Technology Platform for ECG and EMG, located it http://www.madebydelta.com/imported/images/DELTA_Web/documents/ME/ePatch_ECG_EMG.pdf, Dated Sep. 2, 2010.

(56) References Cited

OTHER PUBLICATIONS

Heydari et al., "Analysis of the PLL jitter due to power/ground and substrate noise"; IEEE Transactions on Circuits and Systems (2004) 51(12): 2404-16.
Philips Respironics (http/minimitter.com/products.cfm) Products, Noninvasive Technology to Help Your Studies Succeed. 510(k) Permanent Notification for Vital Sense. Apr. 22, 2004.
Sanduleanu et al., "Octave tunable, highly linear, RC-ring oscillator with differential fine-coarse tuning, quadrature outputs and amplitude control for fiber optic transceivers" (2002) IEEE MTT-S International Microwave Symposium Digest 545-8.
Tajalli et al., "Improving the power-delay performance in subthreshold source-coupled logic circuits" Integrated Circuit and System Design. Power and Timing Modeling, Optimization and Simulation, Springer Berlin Heidelberg (2008) 21-30.
Yang et al., "Fast-switching frequency synthesizer with a discriminator-aided phase detector" IEEE Journal of Solid-State Circuits (2000) 35(10): 1445-52.
Arshak et al., A Review and Adaptation of Methods of Object Tracking to Telemetry Capsules IC-Med (2007) vol. 1, No. 1, Issue 1, pp. 35 of 46.
"ASGE Technology Status Evaluation Report: wireless capsule endoscopy" American Soc. For Gastrointestinal Endoscopy (2006) vol. 63, No. 4; 7 pp.
Aydin et al., "Design and implementation considerations for an advanced wireless interface in miniaturized integrated sensor Microsystems" Sch. of Eng. & Electron., Edinburgh Univ., UK; (2003); abstract.
Brock, "Smart Medicine: The Application of Auto-ID Technology to Healthcare" Auto-ID Labs (2002) http://www.autoidlabs.org/uploads/media/MIT-AUTOID-WH-010.pdf.
Delvaux et al., "Capsule endoscopy: Technique and indications" Clinical Gastoenterology (2008) vol. 22, Issue 5, pp. 813-837.
Fawaz et al., "Enhanced Telemetry System using CP-QPSK Band-Pass Modulation Technique Suitable for Smart Pill Medical Application" IFIP IEEE Dubai Conference (N.D.); http://www.asic.fh-offenburg.de/downloads/ePille/IFIP_IEEE_Dubai_Conference.pdf.
Given Imaging, "Agile Patency Brochure" http://www.inclino.no/documents/AgilePatencyBrochure_Global_GMB-0118-01.pdf;(N.D.) 4pp.
Gonzalez-Guillaumin et al., "Ingestible capsule for impedance and pH monitoring in the esophagus" IEEE Trans Biomed Eng. (2007) 54(12: 2231-6; abstract.
Greene, "Edible RFID microchip monitor can tell if you take your medicine" Bloomberg Businessweek (2010) 2 pp.; http://www.businessweek.com/idg/2010-03-31/edible-rfid-microchip-monitor-can-tell-if-you-take-your-medicine.html.
Melanson, "Walkers swallow RFID pills for science" Engadget (2008); http://www.engadget.com/2008/07/29/walkers-swallow-rfid-pills-for-science/.
"New 'smart pill' to track adherence" E-Health-Insider (2010) http://www.e-health-insider.com/news/5910/new_'smart_pill'_monitors_medicines.
"RFID "pill" monitors marchers" RFID News (2008) http://www.rfidnews.org/2008/07/23/rfid-pill-monitors-marchers/.
"SensiVida minimally invasive clinical systems" Investor Presentation Oct. (2009) 28pp; http://www.sensividamedtech.com/SensiVidaGeneralOctober09.pdf.
Shrivas et al., "A New Platform for Bioelectronics-Electronic Pill", Cummins College, N.D.; http://www.cumminscollege.org/downloads/electronics_and_telecommunication/New sletters/Currenr%20Newsletters.pdf.
"The SmartPill Wireless Motility Capsule" SMARTPILL, The Measure of GI Health; http://www.smartpillcorp.com/index.cfm?pagepath=Products/The_SmartPill_Capsule &id=17814.
Solanas et al., "RFID Technology for the Health Care Sector" Recent Patents on Electrical Engineering (2008) 1, 22-31.
Swedberg, "University Team Sees Ingestible RFID Tag as a Boon to Clinical Trials" RFID Journal (2010) Apr. 27th; http://www.rfidjournal.com/article/view/7560/1.
University of Florida News "Rx for health: Engineers design pill that signals it has been swallowed" (2010) 2pp.; http://news.ufl.edu/2010/03/31/antenna-pill-2/.
Mackay et al., Radio telemetering from within the body: Inside information is revealed by tiny transmitters that can be swallowed or implanted in man or animal. Science 1961;134(3486):1196-1202.
Mackay et al., Endoradiosonde. Nature 1957;179(4572):1239-40, 179.
Zworkin, A 'radio pill.' Nature 1957;179:898.
Yao et al., Low Power Digital Communication in Implantable Devices Using Volume Conduction of Biological Tissues. Proceedings of the 28th IEEE, EMBC Annual International Conference 2006 (Aug. 30-Sep. 3); New York, USA.
McKenzie et al., Validation of a new telemetric core temperature monitor. J. Therm. Biol. 2004;29(7-8):605-11.
Tatbul et al., Confidence-based data management for personal area sensor networks. ACM International Conference Proceeding Series 2004;72.
Zimmerman: Personal Area Networks: Near-field intrabody communication. IBM Systems Journal 1996;35(3-4):609-17.
Mini Mitter Co, Inc, 510(k) Premarket Notification Mini-Logger for Diagnostic Spirometer. Sep. 21, 1999.
Mini Mitter Co, Inc. 510(k) Premarket Notification for VitalSense. Apr. 22, 2004.
Mini Mitter Co, Inc. Actineart. Traditional 510(k) Summary. Sep. 27, 2005.
Mini Mitter Co, Inc. VitalSense Integrated Physiological Monitoring System. Product Description.
Mini Mitter Co. Inc. VitalSense-Wireless Vital Signs Monitoring. Temperatures.com Mar. 31, 2009.
Mini Mitter Co, Inc. Noninvasive technology to help your studies succeed. Mini Mitter.com Mar. 31, 2009.
Barrie, Heidelberg pH capsule gastric analysis, Textbook of Natural Medicine, 1992, Pizzorno, Murray & Barrie.
Carlson et al., Evaluation of a non-invasive respiratory monitoring system for sleeping subjects. Physiological Measurement 1999;20(1):53.
Mojaverian et al., Estimation of gastric residence time of the Heidelberg capsule in humans: effect of varying food composition. Gastroenterology 1985;89(2):392-7.
Xiaoming et al., A telemedicine system for wireless home healthcare based on bluetooth and the internet. Telemedicine Journal and e-health 2004;10(S2):S110-6.
Intromedic, MiroCam Innovative Capsule Endoscope Pamphlet. 8 pages. (http://www.intromedic.com/en/productinfo.asp).
"Smartlife awarded patent for knitted transducer" Innovation in Textiles News: http://www.innovationintextiles.com/articles/208.php; 2pp. (2009).
Hotz "The Really Smart Phone" The Wall Street Journal, What They Know (2011); 6 pp.; http://online.wsj.com/article/SB10001424052748704547604576263261679848814.html?mod=djemTECH_t.
Evanczuk, S., "PIC MCU software library uses human body for secure communications link" EDN Network; edn.com; Feb. 26, 2013 Retrieved from Internet Jun. 19, 2013 at http://www.edn.com/electronicsproducts/other/4407842/PIC-MCU-software-library-uses-human-body-for-secure-communications-link; 5 pp.
Trutag, Technologies, Inc., Spectral Microtags for Authentication and Anti-Counterfeiting; "Product Authentication and Brand Protection Solutions"; http://www.trutags.com/;downloaded Feb. 12, 2013; 1 pp.
Eldek A., "Design of double dipole antenna with enhanced usable bandwidth for wideband phased array applications" Progress in Electromagnetics Research PIER 59, 1-15 (2006).
Ferguson et al., "Dialectric Constant Studies III Aqueous Gelatin Solutions" J. Chem. Phys. 2, 94 (1934) p. 94-98.
Furse C. M., "Dipole Antennas" J. Webster (ed). Wiley Encyclopedia of Electrical and Electronics Engineering (1999) p. 575-581.

(56) References Cited

OTHER PUBLICATIONS

Gaglani S. "Put Your Phone, or Skin, on Vibrate" MedGadget (2012) http://medgadget.com/2012/03/put-your-phone-or-skin-on-vibrate.html 8pp.

ISFET—Ion Sensitive Field-Effect Transistor; MICROSENS S.A. pdf document. First in Office Action dated Jun. 13 (2011) for U.S. Appl. No. 12/238,345; 4pp.

Kamada K., "Electrophoretic deposition assisted by soluble anode" Materials Letters 57 (2003) 2348-2351.

O'Brien et al., "The Production and Characterization of Chemically Reactive Porous Coatings of Zirconium Via Unbalanced Magnetron Sputtering" Surface and Coatings Technology (1996) 86-87; 200-206.

Rolison et al., "Electrically conductive oxide aerogels: new materials in electrochemistry" J. Mater. Chem. (2001) 1, 963-980.

Roulstone, et al., "Studies on Polymer Latex Films: I. A study of latex film morphology" Polymer International 24 (1991) pp. 87-94.

Shin et al., "A Simple Route to Metal Nanodots and Nanoporous Metal Films"; Nano Letters, vol. 2, No. 9 (2002) pp. 933-936.

U.S. Appl. No. 12/238,345, filed Sep. 25, 2008, Hooman et al., Non-Final Office Action mailed Jun. 13, 2011 22pp.

Walkey, "MOSFET Structure and Processing"; 97.398* Physical Electronics Lecture 20; First in Office Action dated Jun. 13, 2011 for U.S. Appl. No. 12/238,345; 24 pp.

Watson, et al., "Determination of the relationship between the pH and conductivity of gastric juice" Physiol Meas. 17 (1996) pp. 21-27.

Wongmanerod et al., "Determination of pore size distribution and surface area of thin porous silicon layers by spectroscopic ellipsometry" Applied Surface Science 172 (2001) 117-125.

Jung, S. "Dissolvable 'Transient Electronics' Will Be Good for Your Body and the Environment" MedGadget; Oct. 1, 2012; Onlne website: http://medgadget.com/2012/10/dissolvable-transient-electronics-will-be-good-for-your-body-and-the-environment.html; downloaded Oct. 24, 2012; 4 pp.

Platt, D., "Modulation and Deviation" AE6EO, Foothills Amateur Radio Society; Oct. 26, 2007; 61 pp.

Baskiyar, S. "A Real-time Fault Tolerant Intra-body Network" Dept. of Comp. Sci & Soft Eng; Auburn University; Proceedings of the 27th Annual IEEE Conference; 0742-1303/02 (2002) IEEE; 6 pp.

Lin et al., "Do Physiological Data Relate to Traditional Usability Indexes?" Proceedings of OZCHI 2005, Canberra, Australia (2005) 10 pp.

Mandryk et al., "A physiological approach for continuously modeling user emotion in interactive play environments" Proceedings of Measuring Behavior (2008) (Maastrichtm the Netherlandsm Aug. 26-29) 2 pp.

Mandryk et al., "Objectively Evaluating Entertainment Technology" Simon Fraser University; CHI (2004) ACM 1-58113-703-6/04/0004; 2 pp.

* cited by examiner

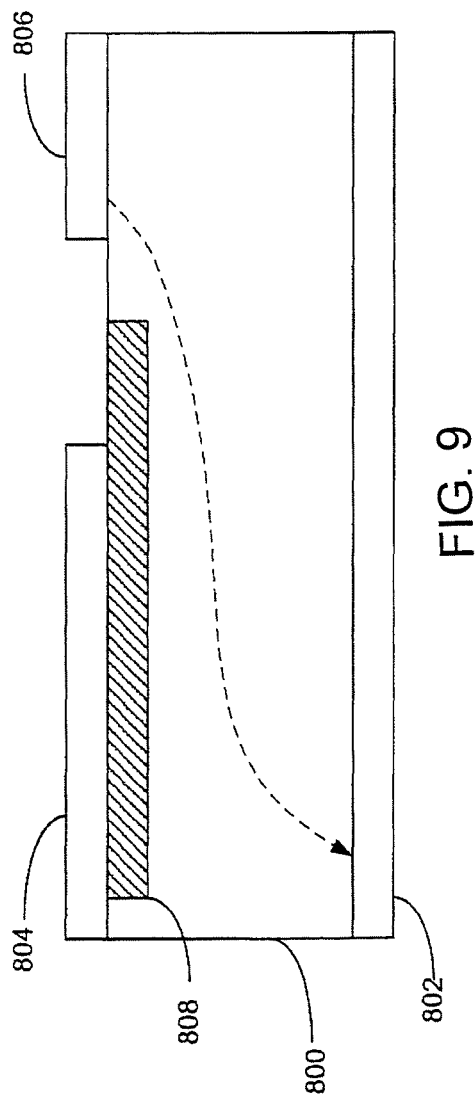
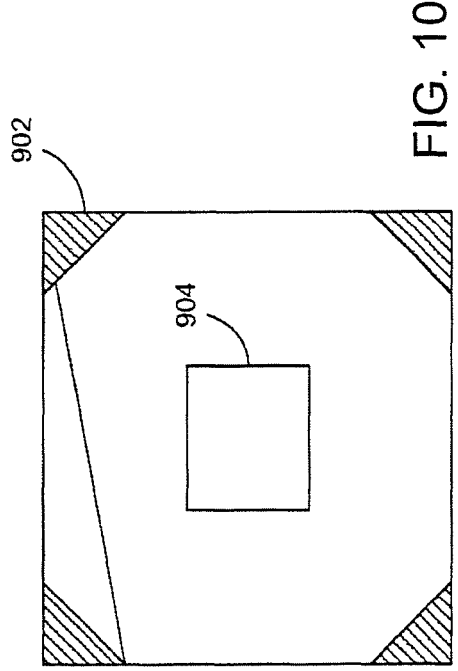

Blood pressure trace (n-time points)     Dosing Pattern     Dose response (m-time points)

$$y_{n \times 1} = X_{n \times m} h_{m \times 1}$$

Solve the linear equation for the dose response, $h$ $$h = (X^T X)^{-1} X^T y$$

INGESTIBLE EVENT MARKER SYSTEMS

CROSS-REFERENCE TO RELATED APPLICATIONS

Pursuant to 35 U.S.C. §119(e), this application claims priority to the filing dates of: U.S. Provisional Patent Application Ser. No. 60/877,780 filed on Feb. 1, 2007; U.S. Provisional Patent Application Ser. No. 60/889,871 filed Feb. 14, 2007; U.S. Provisional Patent Application Ser. No. 60/889,868 filed Feb. 14, 2007; U.S. Provisional Patent Application Ser. No. 60/941,144 filed Jun. 1, 2007; U.S. Provisional Patent Application Ser. No. 60/949,198 filed on Jul. 11, 2007; U.S. Provisional Patent Application Ser. No. 60/949,223 filed on Jul. 11, 2007; U.S. Provisional Patent Application Ser. No. 60/949,208 filed on Jul. 11, 2007; and U.S. Provisional Patent Application Ser. No. 60/956,694 filed on Aug. 18, 2007; the disclosures of which applications are herein incorporated by reference.

INTRODUCTION

There are many instances in both medical and non-medical applications where one desires to note a personal event, i.e., an event that is specific to a given individual. Examples of medical applications where one may wish to note an event that is specific to a given individual include, but are not limited to, the onset of one or more physiological parameters of interest, including disease symptoms, the administration of a medication, etc. Examples of non-medical applications where one desires to note an event that is specific to a given individual include, but are not limited to: the ingestion of certain types of foods (e.g., for individuals on controlled diets), the commencement of an exercise regimen, etc.

Because there are many instances where one wishes to note a personal event, a variety of different methods and technologies have been developed to make such notation possible. For example, log books and techniques have been developed in which individuals, e.g., patients and/or their health care provides, can record, e.g., by manually writing or data entry, time and date of an event.

However, there continues to be a need for improvements in personal event monitoring. For example, manually logging when an event takes place can be time consuming and prone to error.

SUMMARY

The present invention provides for rapid and simple notation of a personal event of interest, i.e., an event that is specific to a given individual. The event may vary widely, ranging from onset of a physiological parameter of interest, e.g., a disease symptom, the start of a given activity, the administration of a therapeutic agent, etc. Notation or marking of personal events according to the present invention finds application in a variety of different applications, including medical and non-medical applications.

The present invention is made possible through an inventive system that includes an ingestible event marker (i.e., an IEM) and a personal signal receiver. Embodiments of the IEM include an identifier, which may or may not be present in a physiologically acceptable carrier. The identifier is characterized by being activated upon contact with a target internal physiological site of a body (e.g., a specific target environment, including a target chemical environment, target physical environment etc.), such as digestive tract internal target site. The personal signal receiver is configured to be associated with a physiological location, e.g., inside of or on the body, and to receive a signal from the IEM. During use, the IEM broadcasts a signal which is received by the personal signal receiver. Where desired, the signal receiver performs one or more subsequent operations, such as relaying the signal to a third external device, recording the signal, processing the recorded signal with additional data points, etc.

BRIEF DESCRIPTION OF THE FIGURES

FIG. 9 illustrates one exemplary IEM chip configuration where two separate electrodes are used for battery and signal transmission, respectively.

FIG. 10 illustrates an exemplary chip configuration that minimizes circuit latch-ups in accordance with one embodiment of the present invention.

DETAILED DESCRIPTION

Figure 1:
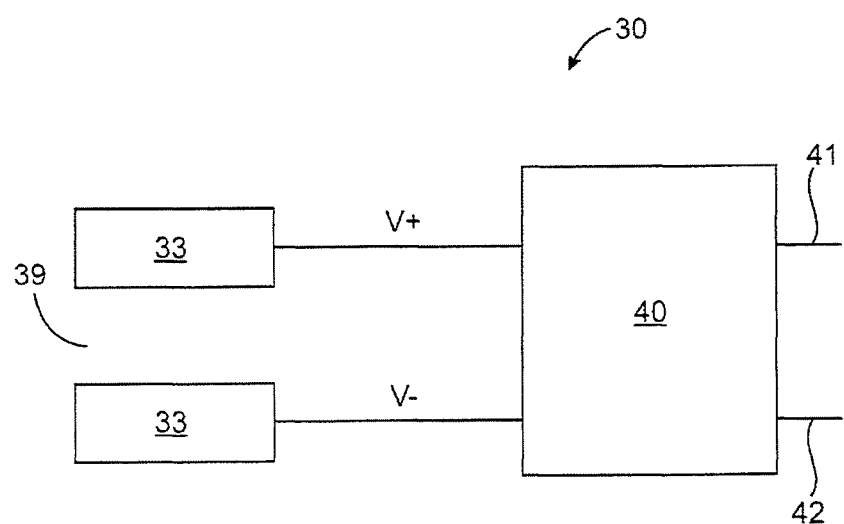
FIG. 1 provides a diagrammatic representation of an identifier according to an embodiment of the invention.

The present invention provides for rapid and simple notation of a personal event of interest, i.e., an event that is specific to a given individual. The event may vary widely, ranging from a disease symptom, the start of a given activity, etc. Notation or marking of personal events according to the present invention finds application in a variety of different applications, including medical and non-medical applications.

The present invention is made possible through an inventive system that includes an ingestible event marker (i.e., IEM) and a personal signal receiver configured to receive a signal emitted from the IEM. Embodiments of the IEM include an identifier, which may or may not be present in a physiologically acceptable carrier. The identifier is characterized by being activated upon contact with an internal target site, such as digestive tract internal target site. The personal signal receiver is configured to be associated with a physiological location, e.g., inside of or on the body, and to receive a signal the IEM.

In further describing the invention in greater detail, embodiments of the physical components of the systems, e.g., IEMS, personal signal receivers and optional external devices, are reviewed first in greater detail. Next, general methods of using the systems of the invention are described. Following this description, a review of various applications in which the systems and methods find use is provided. Also reviewed in greater detail below are kits that include components of the systems, e.g., IEMs, receivers, etc.

Ingestible Event Marker Compositions

Embodiments of the invention include ingestible event marker compositions having an identifier stably associated therewith. The identifier of the IEM compositions is one that generates (i.e., emits) a detectable signal upon contact of the identifier with a target physiological sight. The identifiers of the present compositions may vary depending on the particular embodiment and intended application of the composition so long as they are activated (i.e., turned on) upon contact with a target physiological location, e.g., stomach. As such, the identifier may be an identifier that emits a signal when it contacts a target body (i.e., physiological) site. The identifier may be any component or device that is capable of providing a detectable signal following activation, e.g., upon contact with the target site. In certain embodiments, the identifier emits a signal once the composition comes into contact with a physiological target site, e.g., as summarized above.

Depending on the embodiment, the target physiological site or location may vary, where representative target physiological sites of interest include, but are not limited to: a location in the gastrointestinal tract, such as the mouth, esophagus, stomach, small intestine, large intestine, etc. In certain embodiments, the identifier is configured to be activated upon contact with fluid in the target site, regardless of the particular composition of the target site.

Depending on the needs of a particular application, the signal obtained from the identifier may be a generic signal, e.g., a signal that merely identifies that the composition has contacted the target site, or a unique signal, e.g., a signal which in some way uniquely identifies that a particular ingestible event marker from a group or plurality of different markers in a batch has contacted a target physiological site. As such, the identifier may be one that, when employed with a batch of unit dosages, e.g., a batch of tablets, emits a signal which cannot be distinguished from the signal emitted by the identifier of any other unit dosage member of the batch. In yet other embodiments, the identifier emits a signal that uniquely identifies that particular identifier. Accordingly, in certain embodiments the identifier emits a unique signal that distinguishes one class of identifier from other types of identifiers. In certain embodiments, the identifier emits a unique signal that distinguishes that identifier from other identifiers. In certain embodiments, the identifier emits a signal that is unique, i.e., distinguishable, from a signal emitted by any other identifier ever produced, where such a signal may be viewed as a universally unique signal (e.g., analogous to a human fingerprint which is distinct from any other fingerprint of any other individual and therefore uniquely identifies an individual on a universal level). In one embodiment, the signal may either directly convey information about a given event, or provide an identifying code, which may be used to retrieve information about the event from a database, i.e., a database linking identifying codes with compositions.

The identifier may generate a variety of different types of signals, including but not limited to: RF signals, magnetic signals, conductive (near field) signals, acoustic signals, etc. Of interest in certain embodiments are the specific signals described in pending PCT application serial no. PCT/US2006/16370 filed on Apr. 28, 2006; the disclosures of various types of signals in this application being specifically incorporated herein by reference. The transmission time of the identifier may vary, where in certain embodiments the transmission time may range from about 0.1 μsec to about 48 hours or longer, e.g., from about 0.1 μsec to about 24 hours or longer, such as from about 0.1 μsec to about 4 hours or longer, such as from about 1 sec to about 4 hours, including about 1 minute to about 10 minutes. Depending on the given embodiment, the identifier may transmit a signal once or transmit a signal two or more times, such that the signal may be viewed as a redundant signal.

In certain embodiments, the identifier is dimensioned to be orally ingestible, e.g., either by itself or upon combination with a physiologically acceptable carrier component of the composition so as to produce a composition that can be readily administered to a subject in need thereof. As such, in certain embodiments, the identifier element is dimensioned to have a width ranging from about 0.05 to about 2 or more mm, e.g., from about 0.05 mm to about 1 mm, such as from about 0.1 mm to about 0.2 mm; a length ranging from about 0.05 to about 2 or more mm, e.g., from about 0.05 mm to about 1 mm, such as from about 0.1 mm to about 0.2 mm and a height ranging from about 0.05 to about 2 or more mm, e.g., from about 0.1 mm to about 1 mm, such as from about 0.05 mm to about 0.3 mm, including from about 0.1 mm to about 0.2 mm. In certain embodiments the identifier is 1 mm$^3$ or smaller, such as 0.1 mm$^3$ or smaller, including 0.2 mm$^3$ or smaller. The identifier element may take a variety of different configurations, such as but not limited to: a chip configuration, a cylinder configuration, a spherical configuration, a disc configuration, etc, where a particular configuration may be selected based on intended application, method of manufacture, etc.

In certain embodiments, the identifier may be one that is programmable following manufacture. For example, the signal generated by the identifier may be determined after the identifier is produced, where the identifier may be field programmable, mass programmable, fuse programmable, and even reprogrammable. Such embodiments are of interest where uncoded identifiers are first produced and following incorporation into a composition are then coded to emit an identifying signal for that composition. Any convenient programming technology may be employed. In certain embodiments, the programming technology employed is RFID technology. RFID smart tag technology of interest that may be employed in the subject identifiers includes, but is not limited to: that described in U.S. Pat. Nos. 7,035,877; 7,035,818; 7,032,822; 7,031,946, as well as published application no. 20050131281, and the like, the disclosures of which are herein incorporated by reference. With RFID or other smart tag technology, a manufacturer/vendor may associate a unique ID code with a given identifier, even after the identifier has been incorporated into the composition. In certain embodiments, each individual or entity involved in the handling of the composition prior to use may introduce information into the identifier, e.g., in the form of programming with respect to the signal emitted by the identifier, e.g., as described in U.S. Pat. No. 7,031,946 the disclosure of which is herein incorporated by reference.

The identifier of certain embodiments includes a memory element, where the memory element may vary with respect to its capacity. In certain embodiments, the memory element has a capacity ranging from about 1 bit to 1 gigabyte or more, such as 1 bit to 1 megabyte, including from about 1 bit to about 128 bit. The particular capacity employed may vary depending on the application, e.g., whether the signal is a generic signal or coded signal, and where the signal may or may not be annotated with some additional information, e.g., name of active agent associated with the identifier, etc.

Identifier components of embodiments of the invention have: (a) an activation component; and (b) a signal generation component, where the signal generation component is activated by the activation component to produce an identifying signal, e.g., as described above.

The activation component is a component that activates the signal generation element of the identifier to provide a signal, e.g., by emission or upon interrogation, following contact of the composition with a target physiological site of interest, such as the stomach. As reviewed in co-pending PCT application serial no. PCT/US2006/016370, activation of the identifier may be achieved in a number of different ways, where such approaches include, but are not limited to: battery completion, battery connection, etc. The different activation approaches disclosed in this co-pending application may be readily adapted to provide activation, as described herein, and as such are herein incorporated by reference in their entirety.

Embodiments of activation elements based on battery completion formats employ a battery that includes, when completed, a cathode, an anode, and an electrolyte, where the electrolyte is made up, at least in part, by fluid present at the target physiologic site (stomach fluid present in the stomach, where the stomach is the target physiological site). For example, when a stomach fluid activated IEM is ingested, it travels through the esophagus and proceeds to enter the stomach. The cathode and anode provided on the IEM do not constitute a full battery. However, when the cathode and anode are exposed to stomach fluid, the stomach fluid acts as the electrolyte component of the battery and completes the battery. Therefore, as the IEM contacts the target site, a power source is provided which activates the identifier. The data signal is then transmitted.

In certain embodiments, the battery that is employed is one that comprises two dissimilar electrochemical materials which constitute the two electrodes (e.g., anode and cathode) of the battery. When the electrode materials are exposed and come in contact with the body fluid, such as stomach acid or other types of fluid, a potential difference (i.e., voltage), is generated between the electrodes as a result of the respective oxidation and reduction reactions that occur the two electrode materials. The two dissimilar materials in an electrolyte are at different potentials. As an example, copper and zinc when put into a cell have different potentials. Similarly, gold and magnesium have different potentials.

Materials and pairings of interest include, but are not limited to those reported in the table below.

| | Electrode Materials | |
|---|---|---|
| | Anode | Cathode |
| Metals | Magnesium, Zinc Sodium (†), Lithium (†) Iron and alloys thereof | |
| Salts | | Copper salts: iodide, chloride, bromide, sulfate, formate, (other anions possible) $Fe^{3+}$ salts: e.g. orthophosphate, pyrophosphate, (other anions possible) Oxygen or hydrogen (††) on platinum, gold or other catalytic surfaces |
| Intercalation compounds | Graphite with Li, K, Ca, Na, Mg | Vanadium oxide Manganese oxide |

(†) Protected anodes: certain high energy anode material such as Li, Na, and other alkali metals are unstable in their pure form in the presence of water or oxygen. These may however be used in an aqueous environment if stabilized. One example of this stabilization is the so-called "protected lithium anode" developed by Polyplus Corporation (Berkeley, CA), where a polymer film is deposited on the surface of lithium metal to protect it from rapid oxidation and allow its use in aqueous environment or air ambient. (Polyplus has IP pending on this).

(††) Dissolved oxygen can also serve as a cathode. In this case, the dissolved oxygen in the bodily fluids would be reduced to OH– at a suitable catalytic surface such at Pt or gold. Other catalysts are also possible. Also of interest dissolved hydrogen in a hydrogen reduction reaction.

In certain embodiments, one or both of the metals may be doped with a non-metal, e.g., to enhance the voltage output of the battery. Non-metals that may be used as doping agents in certain embodiments include, but are not limited to: sulfur, iodine and the like.

In certain embodiments, the electrode materials are cuprous iodine (CuI) or cuprous chloride as the cathode and magnesium (Mg) metal or magnesium alloy as the anode.

Embodiments of the present invention use electrode materials that are not harmful to the human body.

In certain of these embodiments, the battery power source may be viewed as a power source that exploits electrochemical reaction in an ionic solution such as gastric fluid, blood, or other bodily fluids and some tissues. FIG. 1 provides a diagrammatic representation of an identifier according to an embodiment of the invention. First and second electrode materials (32 and 33) are in an ionic solution 39 (e.g., stomach fluid). This configuration creates a low voltage (V−) and a high voltage (V+) as applied to an electronic circuit 40. The two outputs of that electronic circuit 40 are E0 41 and E1 42, which are the signal-transmission electrodes. In an alternate embodiment, the signal generation element 30 includes a single electrode. In an alternative embodiment, a coil for communication may be provided. In certain embodiments, a structure, e.g., membrane, larger than the chip which defines a path for the current to travel is provided.

Electrodes 32 and 33 can be made of any two materials appropriate to the environment in which the identifier 30 will be operating. The active materials are any pair of materials with different electrochemical potentials. For instance, in some embodiments where ionic solution 39 comprises stomach acids, electrodes 32 and 33 may be made of a noble metal (e.g., gold, silver, platinum, palladium or the like) so that they do not corrode prematurely. Alternatively, the electrodes can be fabricated of aluminum or any other conductive material whose survival time in the applicable ionic solution is long enough to allow identifier 30 to perform its intended function. Suitable materials are not restricted to metals, and in certain embodiments the paired materials are chosen from metals and non-metals, e.g., a pair made up of a metal (such as Mg) and a salt (such as CuI). With respect to the active electrode materials, any pairing of substances—metals, salts, or intercalation compounds—with suitably different electrochemical potentials (voltage) and low interfacial resistance are suitable.

In certain embodiments, the IEMs are characterized by including series battery structures, where these series battery structures may be configured to substantially reduce, if not eliminate, shorting between electrode elements of different battery structures of the series. As the batteries of the present invention are series batteries, the batteries include two or more individual battery structures or units, where the number of battery structures that may be present in a given series battery of the invention may be two or more, three or more, four or more, five or more, etc., as desired for a given application of the battery. Each individual battery structure includes at least one anode and at least one cathode, where the anode and the cathode are present on a surface of a solid support, where the support for each of the anode and cathode may be the same or different.

Aspects of the series batteries include configurations that substantially reduce, if not eliminate, shorting between two or more of the batteries of a given series. This elimination of shorting is provided despite the small area that is occupied by the two or more batteries of the series, e.g., where the battery units are present on the surface of a solid support. Embodiments of the subject series batteries include configurations in which the resistance between electrodes of two different battery structures of the series battery is much higher than the resistance between electrodes within a given battery structure. In certain embodiments, the ratio of the ionic resistance between electrodes of two different battery structures as compared to electrodes (i.e., anode and cathode) within a single battery structure is about 1.5× or more, such as about 5× or more, including about 10× or more.

Depending on a particular series battery configuration, shorting between batteries can be reduced, if not eliminated, using a variety of different approaches. Certain approaches that can be employed are reviewed in greater detail below, where the below approaches may or may not be used in combination, depending on the particular battery configuration of interest.

In certain embodiments, two or more battery structures are provided in series, where each battery structure includes a chamber having an anode and cathode positioned inside the chamber, e.g., on the same internal wall or different internal walls. The chamber has a volume that may vary, and in certain embodiments ranges from about $10^{-12}$ to about $10^{-5}$ L, such as from about $10^{-11}$ to about $10^{-7}$ L and including from about $10^{-10}$ to about $10^{-8}$ L. In certain embodiments, the chamber may include an amount of a dried conductive medium, e.g., as described in PCT Application Serial No. PCT/US07/82563, the disclosure of which is herein incorporated by reference.

In certain embodiments, a given chamber includes at least one fluid entry port and at least one fluid exit port, so that liquid, e.g., stomach fluid, can enter the chamber when the composition in which the battery is present reaches the target site of interest and gas can exit the chamber upon entry of the liquid. While the dimensions of the fluid entry and exit ports may vary, in certain embodiments the ports have a diameter ranging from about 0.01μ to about 2 mm, such as from about 5 μm to about 500 μm.

The ports of a given chamber are positioned relative to ports of other chambers to provide for efficient entry of fluid into and exit of gas from the chamber, and are also positioned to provide for substantially no, if any, shorting between two or more different chambers of the series battery. As such, location of the ports is chosen in view of both the battery structure itself and its physical relation to other battery structures of the series battery. Any configuration of fluid ports may be chosen, so long as the configuration provides the desired resistance ratio, e.g., as described above.

Figure 28:
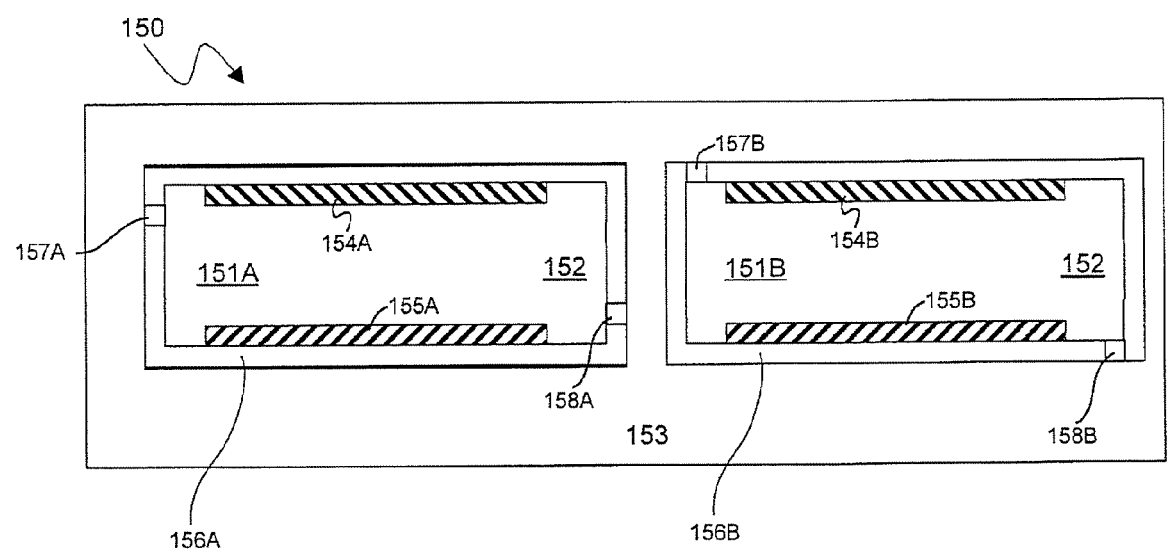
FIG. 28 provides an overhead view of a series battery according to one embodiment of the invention.

FIG. 28 provides an overhead view of a series battery according to an embodiment of the invention. In FIG. 28, series battery 150 is made up of two different battery structures 151A and 151B present on surface 152 of solid support 153. Battery structure 151A includes cathode 154A and anode 155A while structure 151B includes cathode 154B and anode 155B. As illustrated, the cathodes and anodes of each battery structure are present in a chamber defined by boundary 156A and 156B. Present in the wall 156A of structure 151A are ports 157A and 158A, which provide for fluid entry and exit from the chamber. Ports 157A and 158A of structure 151A are positioned relative to ports 157B and 158B of structure 151B so that the potential for shorting between the electrodes of structures 151A and 151B is substantially, if not completely eliminated. In the configuration shown in FIG. 28, ports 157A and 158A are positioned on opposing walls of boundary 156A and ports 157B and 158B are positioned on opposing walls of boundary 156B. Furthermore, ports 157A and 158A are present on opposing walls of their boundary element 156A with respect to the positioning of ports 157B and 158B in boundary element 156B.

Figure 29:
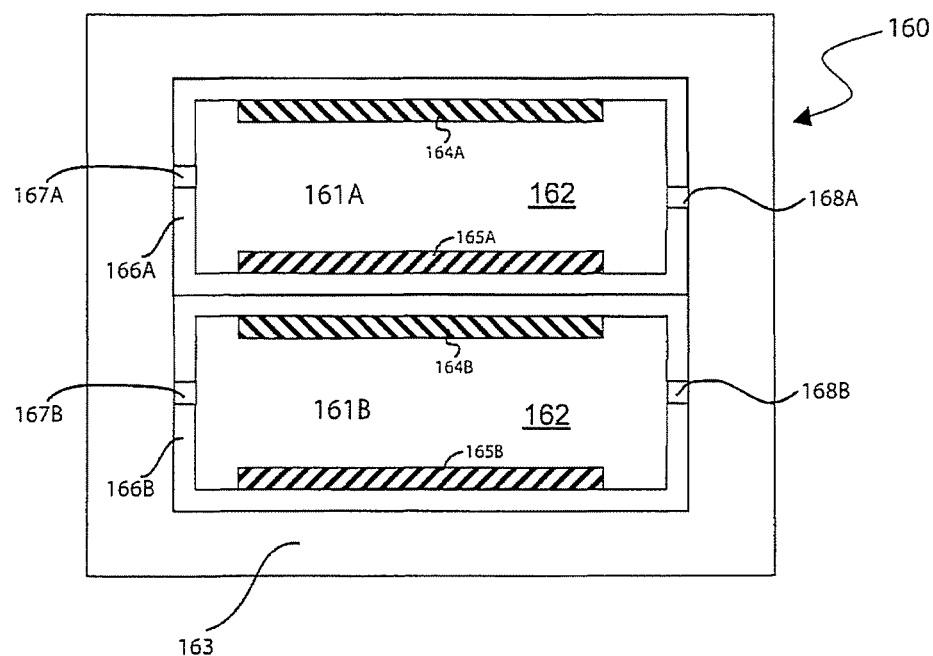
FIG. 29 provides an overhead view of a series battery according to another embodiment of the invention.

FIG. 29 provides an overhead view of a series battery according to another embodiment of the invention. In FIG. 29, series battery 160 is made up of two different battery structures 161A and 161B present on surface 162 of solid support 163. Battery structure 161A includes cathode 164A and anode 165A while structure 161B includes cathode 164B and anode 165B. The structure illustrated in FIG. 29 differs from that shown in FIG. 28 as the battery structures are stacked next to each other. As illustrated, the cathodes and anodes of each battery structure are present in a chamber defined by boundary 166A and 166B. Present in the wall 166A of structure 161A are ports 167A and 168A, which provide for fluid entry and exit from the chamber. Ports 167A and 168A of structure 161A are positioned relative to ports 167B and 168B of structure 161B so that the potential for shorting between the electrodes of structures 161A and 161B is substantially, if not completely eliminated.

In addition to, or instead of, locating fluid ports to provide for the desired resistance ratio, the fluid ports may be modified to provide the desired resistance between battery structures. For example, the port may include a selective semi-permeable membrane. Any convenient semi-permeable membrane may be employed. The semi-permeable membrane may comprise ePTFE, Dacron®, polyurethane, silicone rubber, poly(lactide-co-glycolide) (PLGA), poly(caprolactone) (PCL), poly(ethylene glycol) (PEG), collagen, polypropylene, cellulose acetate, poly(vinylidene fluoride) (PVDF), nafion or other biocompatible material. The pore size of the membrane may vary depending on the particular configuration, where in certain embodiments the membrane have a pore size (MW cutoff of about 1000 d or less, such as about 500 d or less, including about 250 d or less, e.g., about 100 d or less, such as about 50 d or less). In certain embodiments, the membrane is a water only permeable membrane, such that water, but little if any other fluid constituents at the target site, pass through the membrane to reach to the dried conductive medium precursor of the identifier.

In certain embodiments, the solid support 153, 163 is a circuitry support element. The circuitry support element may take any convenient configuration, and in certain embodiments is an integrated circuit (IC) chip. The surface upon which the electrode elements are positioned may be the top surface, bottom surface or some other surface, e.g., side surface, as desired, where in certain embodiments the surface upon which the electrode elements are at least partially present is a top surface of an IC chip.

In certain embodiments, the series batteries have a small form factor. Batteries may be about 20 mm$^3$ or smaller, e.g., about 10 mm$^3$ or smaller, such as 1.0 mm$^3$ or smaller, including 0.1 mm$^3$ or smaller, including 0.02 mm$^3$ or smaller. In certain embodiments, the battery element is dimensioned to have a width ranging from about 0.01 mm to about 100 mm, e.g., from about 0.1 mm to about 20 mm, including from about 0.5 mm to about 2 mm; a length ranging from about 0.01 mm to about 100 mm, e.g., from about 0.1 mm to about 20 mm, including from about 0.5 mm to about 2 mm, and a height ranging from about 0.01 mm to about 10 mm, e.g., from about 0.05 mm to about 2 mm, including from about 0.1 mm to about 0.5 mm.

Series battery embodiments includes those further described in U.S. Provisional Application Ser. No. 60/889, 871; the disclosure of which is herein incorporated by reference.

The signal generation component of the identifier element is a structure that, upon activation by the activation component, emits a detectable signal, e.g., that can be received by a receiver, e.g., as described in greater detail below. The signal generation component of certain embodiments can be any convenient component or element that is capable of producing a detectable signal and/or modulating transduced broadcast power, upon activation by the activation component. Detectable signals of interest include, but are not limited to: conductive signals, acoustic signals, etc. As reviewed above, the signals emitted by the signal generator may be generic or unique signals, where representative types of signals of interest include, but are not limited to: frequency shift coded signals; amplitude modulation signals; frequency modulation signals; etc.

In certain embodiments, the signal generation element includes circuitry, as developed in more detail below, which produces or generates the signal. The type of circuitry chosen may depend, at least in part, on the driving power that is supplied by the power source of the identifier. For example, where the driving power is 1.2 volts or above, standard CMOS circuitry may be employed. In other embodiments where the driving power ranges from about 0.7 to about 1.2 V, sub-threshold circuit designs may be employed. For driving powers of about 0.7 V or less, zero-threshold transistor designs may be employed.

In certain embodiments, the signal generation component includes a voltage-controlled oscillator (VCO) that can generate a digital clock signal in response to activation by the activation component. The VCO can be controlled by a digital circuit, which is assigned an address and which can control the VCO with a control voltage. This digital control circuit can be embedded onto a chip that includes the activation component and oscillator. Using amplitude modulation or phase shift keying to encode the address, an identifying signal is transmitted.

The signal generation component may include a distinct transmitter component that serves to transmit the generated signal to a remote receiver, which may be internal or external to the patient, as reviewed in greater detail below. The transmitter component, when present, may take a number of different configurations, e.g., depending on the type of signal that is generated and is to be emitted. In certain embodiments, the transmitter component is made up of one or more electrodes. In certain embodiments, the transmitter component is made up of one or more wires, e.g., in the form of antenna(e). In certain embodiments, the transmitter component is made up of one or more coils. As such, the signal transmitter may include a variety of different transmitters, e.g., electrodes, antennas (e.g., in the form of wires) coils, etc. In certain embodiments, the signal is transmitted either by one or two electrodes or by one or two wires (a two-electrode transmitter is a dipole; a one electrode transmitter forms a monopole). In certain embodiments, the transmitter only requires one diode drop of power. In some embodiments, the transmitter unit uses an electric dipole or electric monopole antenna to transmit signals. In certain embodiments, the identifier employs a conductive near-field mode of communication in which the body itself is employed as a conductive medium. In such embodiments, the signal is not a magnetic signal or high frequency (RF) signal.

Figure 2:
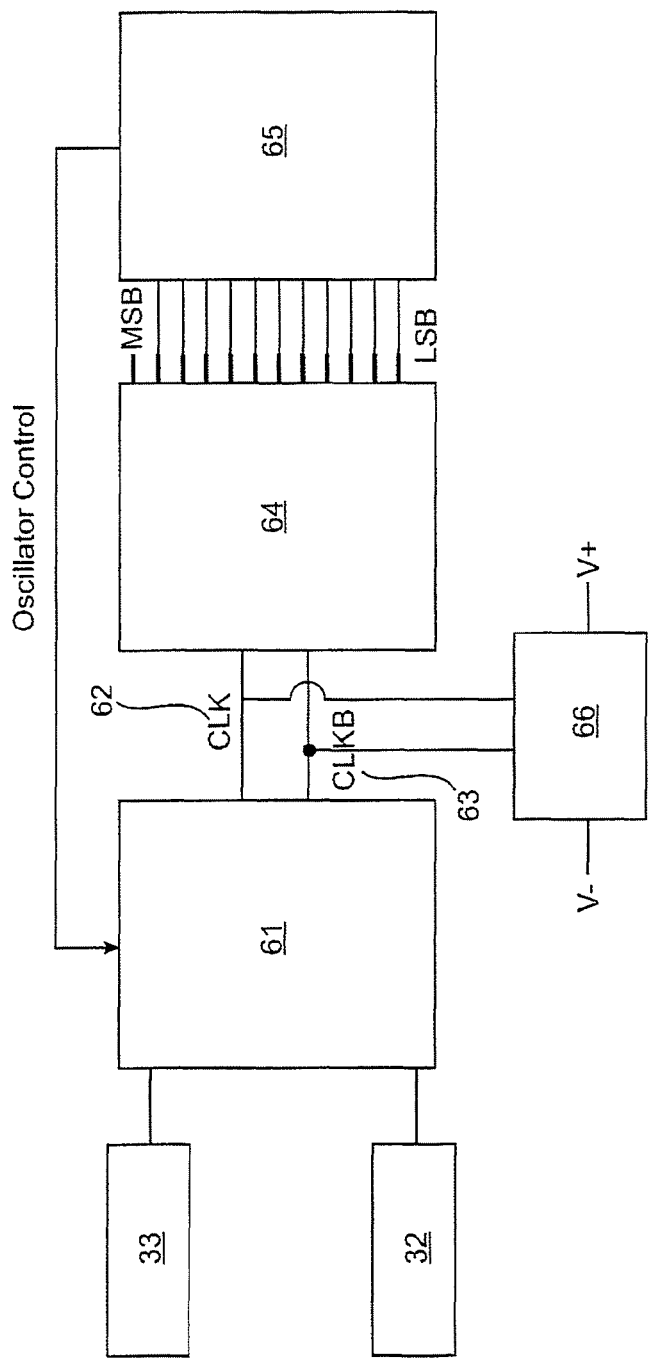
FIG. 2 provides detail of certain implementations of an electronic circuit of various embodiments of the invention.

FIG. 2 shows the detail of one implementation of an electronic circuit that can be employed in an identifier according to the present invention. On the left side are the two battery electrodes, metal 1 and metal 2 (32 and 33). These metals, when in contract with an electrolyte, form a battery that provides power to an oscillator 61, in this case shown as a schematic. The metal 1 32 provides a low voltage, (ground) to the oscillator 61. Metal 2 33 provides a high voltage (V-high) to the oscillator 61. As the oscillator 61 becomes operative, it generates a clock signal 62 and an inverted clock signal 63, which are opposites of each other. These two clock signals go into the counter 64 which simply counts the number of clock cycles and stores the count in a number of registers. In the example shown here, an 8 bit counter is employed. Thus, the output of counter 64 begins with a value of "00000000," changes to "00000001" at the first clock cycle, and continues up to "11111111." The 8-bit output of counter 64 is coupled to the input of an address multiplexer (mux) 65. In one embodiment, mux 65 contains an address interpreter, which can be hard-wired in the circuit, and generates a control voltage to control the oscillator 61. Mux 65 uses the output of counter 64 to reproduce the address in a serial bit stream, which is further fed to the signal-transmission driving circuit. Mux 65 can also be used to control the duty-cycle of the signal transmission. In one embodiment, mux 65 turns on signal transmission only one sixteenth of the time, using the clock counts generated by counter 64. Such a low duty cycle conserves power and also allows other devices to transmit without jamming their signals. The address of a given chip can be 8 bits, 16 bits or 32 bits.

According to one embodiment, mux 65 produces a control voltage, which encodes the address serially and is used to vary the output frequency of oscillator 61. By example, when the control voltage is low, that is, when the serial address bit is at a 0, a 1 megahertz signal is generated by the oscillator. When the control voltage is high, that is, when the address bit is a 1, a 2 megahertz signal is generated the oscillator. Alternately, this can be 10 megahertz and 20 megahertz, or a phase shift keying approach where the device is limited to modulating the phase. The purpose of mux 65 is to control the frequency of the oscillator or an AC alternative embodiment of the amplified signal of oscillation.

The outputs of mux 65 are coupled to electrode drive 66 which can drive the electrodes to impose a differential potential to the solution, drive an oscillating current through a coil to generate a magnetic signal, or drive a single electrode to push or pull charge to or from the solution.

In this manner, the device broadcasts the sequence of 0's and 1's which constitute the address stored in mux 65. That address would be broadcast repeatedly, and would continue broadcasting until metal 1 or metal 2 (32 and 33) is consumed and dissolved in the solution, when the battery no longer operates.

Other configurations for the signal generation component are of course possible. Other configurations of interest include, but are not limited to: those described in copending PCT application serial no. PCT/US2006/016370; provisional application Ser. No. 60/807,060 filed on Jul. 11, 2006; the disclosure of which is herein incorporated by reference.

In certain embodiments, the activation component includes a power storage element. For example, a duty cycle configuration may be employed, e.g., where slow energy production from a battery is stored in a power storage element, e.g., in a capacitor, which then provides a burst of power that is deployed to the signal generation component. In certain embodiments, the activation component includes a timing element which modulates, e.g., delays, delivery of power to the signal generation element, e.g., so signals from different compositions, e.g., different IEMs, that are administered at substantially the same time are produced at different times and are therefore distinguishable.

In certain embodiments, the components or functional blocks of the identifiers of the ingestible event markers are present on integrated circuits, where the integrated circuits include a number of distinct functional blocks, i.e., modules. Within a given identifier, at least some of, e.g., two or more, up to an including all of, the functional blocks, e.g., power source, transmitter, etc., may be present in a single integrated circuit in the receiver. By single integrated circuit is meant a single circuit structure that includes all of the different functional blocks. As such, the integrated circuit is a monolithic integrated circuit (also known as IC, microcircuit, microchip, silicon chip, computer chip or chip) that is a miniaturized electronic circuit (which may include semiconductor devices, as well as passive components) that has been manufactured in the surface of a thin substrate of semiconductor material. The integrated circuits of certain embodiments of the present invention may be hybrid integrated circuits, which are miniaturized electronic circuits constructed of individual semiconductor devices, as well as passive components, bonded to a substrate or circuit board.

Embodiments of the present invention provide a low-power, miniature, ingestible marker that includes an integrated circuit (IC) which automatically activates itself after the contacts a patient's body fluid, transmits a predetermined signal based on locally generated power, and de-activates itself after a certain period of time. In these embodiments, as described above, the IEM uses the patient's body fluid, such as the stomach acid, to form a voltaic cell. Furthermore, the IEM uses a special circuit that changes the impedance of a closed circuit which forms the voltaic cell, thereby creating an external signal by modulating the amplitude and waveform of the current that flows through the patient's tissue and body fluid. As described in more detail below, such a circuit configuration allows the circuitry to operate at a low voltage while generating a signal that is sufficiently strong to be detected by a receiver in contact with the patient's body.

An IEM's IC can be packaged with an integrated voltaic cell which can be manufactured on the same substrate as the IC circuit. This wafer level integration significantly reduces the chip and simplifies the manufacturing process. As a result, each IEM's cost can be considerably lowered. In one embodiment, the anode and cathode electrode materials are fabricated on each side of the substrate, whereby the IC logic is situated between the two electrodes. In one embodiment, the logic circuit is situated in a location chosen to minimize the area overlapping vertically with the anode or cathode electrode.

Figure 3:
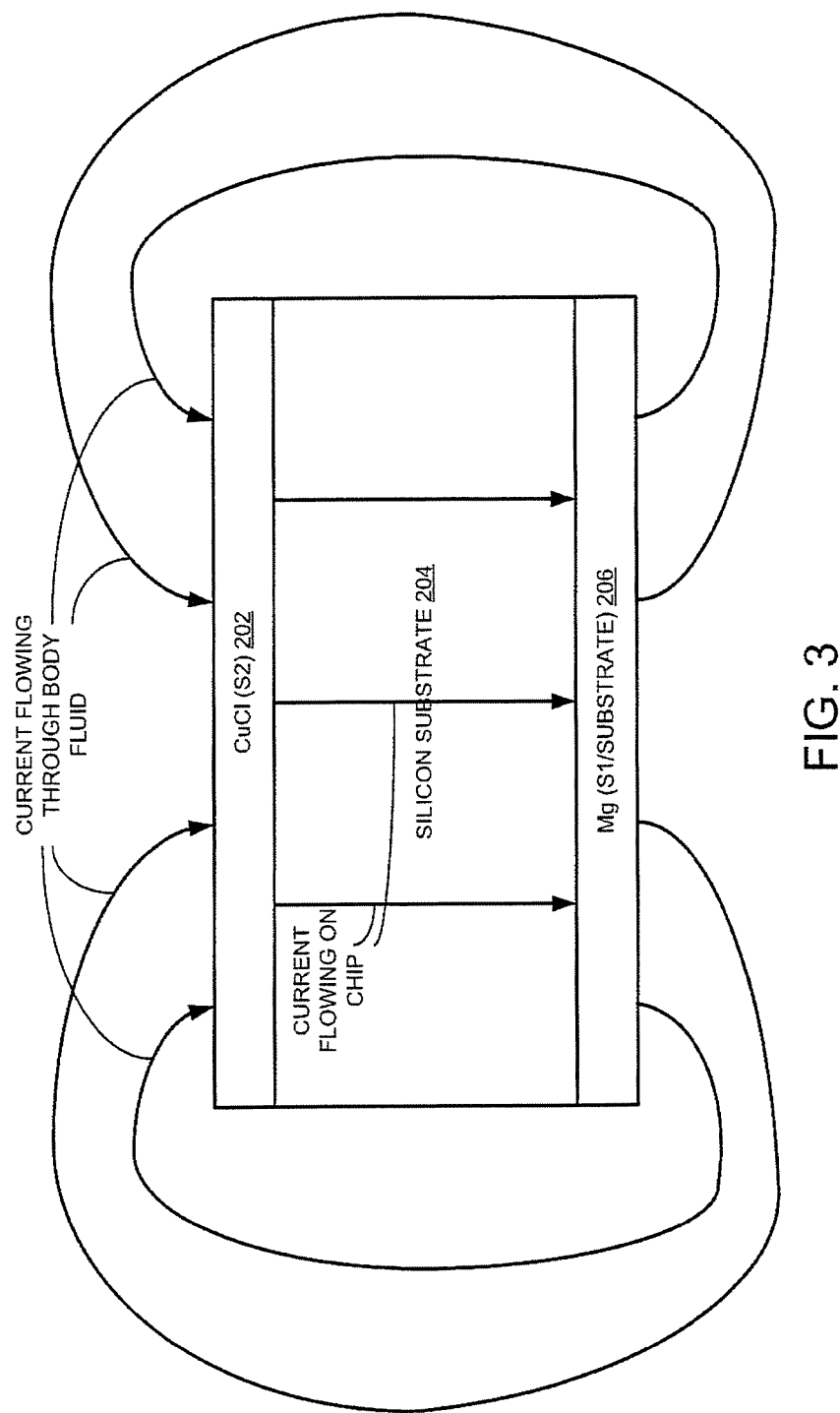
FIG. 3 illustrates an exemplary device configuration of an IEM IC in accordance with one embodiment of the present invention.

FIG. 3 illustrates an exemplary device configuration of the IEM IC in accordance with one embodiment of the present invention. In one embodiment, the IC chip's substrate 204 is coupled to the anode (S1) of the voltaic cell, which can be a layer of Magnesium (Mg) 206 coated on the backside of substrate 204. On the opposite side of substrate 204 is a layer of cathode (S2) material 202, which in this example is Copper Chloride (CuCl). The electrodes 202 and 206, and the body fluid which serves as an electrolyte fluid, form the voltaic cell. The IEM IC circuitry, which is fabricated on substrate 204, is the "external" circuit that forms a return circuit for the voltaic cell. Essentially, the IEM IC changes the impedance of this "external" circuit, thereby changing the total amount of current flowing through the body fluid. A receiving circuit, e.g., on a personal health receiver as described in greater detail below, in contact with the body fluid can detect this current change and receive the encoded messages.

Note that the two electrodes S1 and S2 of the voltaic cell also serve as the transmission electrodes for the IC. This configuration significantly reduces the complexity of the IC chip. Furthermore, since a fluid-metal interface often exhibits high impedances, using a separate pair of electrodes which are different from the voltaic-cell electrodes can introduce additional high impedance to the circuit, thereby reducing the transmission efficiency and increasing power consumption. Therefore, using the voltaic-cell electrodes for transmission also improves the power-efficiency of the IC circuitry.

The IC of the IEM functions as an ingestible transmitter that transmits a unique identification code once powered on. This IC can be packaged within a pharmaceutically acceptable vehicle, e.g., as described above. When the IEM is swallowed and inside the stomach, the integrated voltaic cell, or battery, uses the stomach acid as the battery electrolyte to power up the main chip and commences broadcasting there-after. Furthermore, several pills can be ingested and transmit at the same time. During operation, a unique identification code, e.g., using BPSK modulation, is broadcasted. This broadcast can be received and demodulated by a receiver, e.g., as described below, which is either implanted under the skin or in contact with the patient's body tissue. The receiver can decode and store the identification code with a time stamp.

In one embodiment, a IEM IC includes an impedance-detection circuitry. This circuitry is configured to detect the impedance between the anode and cathode electrodes. When the electrodes are not submerged in an electrolyte fluid, e.g., stomach acid, the impedance between the electrodes is high and the IC is not activated. When the electrodes are in contact with the electrolyte fluid and the impedance-detection circuit detects the drop in impedance, the IC is then activated.

Embodiments of the present invention allow the smart pill to operate at unconventionally low voltages. In general, the IC can operate with a power supply at 0.8-2 V. In one embodiment, the IC is configured to operate with a power supply at approximately 1.0-1.6 V. In addition, the voltaic cell exhibits an internal impedance of 200-10K Ohm. In one embodiment, the voltaic cell exhibits in internal impedance of approximately 500-5K Ohm. The IC also provides an ultra stable carrier clock frequency, thereby facilitating error-resistant communications.

In one embodiment, an IC includes three parts of circuitry. The first part is an impedance-detection circuitry that uses the battery as the power supply. The second part is the main circuit that broadcasts the messages. The impedance detection circuit can hold the main circuit at substantially zero power consumption before the battery detects an impedance lower than 10K Ohms. When the impedance drops to approximately 10K Ohms, the main circuit is activated and the impedance detection circuit can decouple itself from the battery. The third part is a watchdog circuitry designed to protect the patient's safety when hazardous situation occurs.

Figure 4:
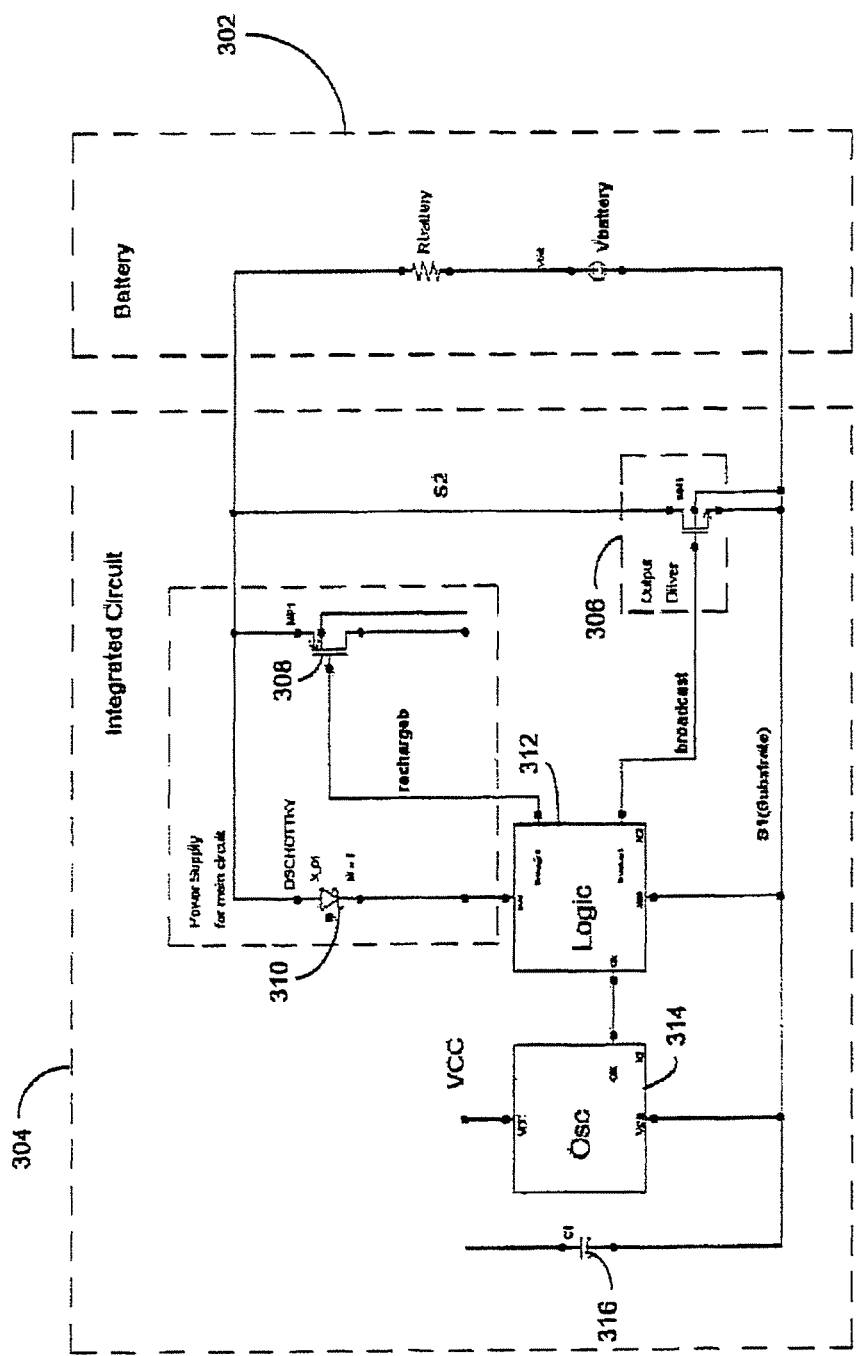
FIG. 4 presents an exemplary schematic diagram illustrating the design of an IEM IC in accordance with one embodiment of the present invention.

FIG. 4 presents an exemplary schematic diagram illustrating the design of a IEM IC in accordance with one embodiment of the present invention. In general, the IEM chip has a battery section 302 and an IC circuitry 304. Battery section 302 includes the voltaic-cell electrodes, which when coupled with electrolyte fluid form a voltaic cell. The two battery electrodes are coupled to the high-voltage rail (VCC) and ground for the IC circuitry, respectively. IC circuitry 304 includes a transmission switch transistor 306, a recharge transistor 308, a recharge-protection diode 310, a recharge capacitor 316, a local oscillator 314, and control logic 312. Local oscillator 314 produces one or more carrier frequencies which is used by control logic 312 to issue a transmission command (labeled as "broadcast") to turn on and off transmission switch transistor 306. For example, oscillator 316 can produce a 20 KHz signal, based on which control logic 312 can generate a binary-phase shift keying (BPSK)-encoded message. Control logic 312 then switches on and off transistor 306 to transmit these messages.

When transistor 312 is turned on, a low-impedance external return circuit is provided between the two voltaic-cell electrodes. Consequently, the current flowing through the patient's body is also increased. When transistor 312 is turned off, the external return circuit between the two voltaic-cell electrodes exhibits a high impedance. Correspondingly, the current flowing through the patient's body is significantly lower. Note that the current draw of the rest of the circuitry, e.g., the oscillator 314 and control logic 312, is sufficiently low so that there is a significant difference in the body current between the broadcast period and the silence period.

When transistor 306 is turned on, the two voltaic-cell electrodes are effectively shorted. As a result, the voltage provided by the electrodes is significantly lower than when transistor 306 is turned off. To ensure that control logic 312 continues to operate properly, recharge capacitor 316 provides the necessary voltage (VCC) to control logic 312. Note that recharge capacitor 316 is recharged when the IC chip is in a silence period, i.e., when transistor 306 remains off. When transistor 306 turns on which causes the voltage between the battery electrodes to drop, diode 310 prevents the charges stored in capacitor 316 from flowing back to the battery electrodes. In one embodiment, diode 310 is a Schottky diode to ensure a fast switching time.

It is possible that, during the transmission period, oscillator 314 and/or control logic 312 have depleted the charges stored in capacitor 316, causing VCC to drop below a certain threshold. For example, the voltage provided by recharge capacitor 316 may drop below the voltage provided by the voltaic cell. The difference between these two voltages may not be large enough to turn on Schottky diode 310. In this case, control logic 312 can issue a recharge signal to turn on recharge switching transistor 308, which couples the battery voltage to capacitor 316 and recharges capacitor 316.

In one embodiment, the communication between the IEM IC and the receiver is simplex. That is, the IEM IC only transmits signals without receiving any signals. The communication is performed via direct coupling between the IC electrodes and the receiver circuitry through the patient's body tissue and fluids. The transmission is performed at two frequencies, for example, one at 10 kHz and the other at 20 kHz. Other numbers of frequencies and frequency values are also possible. In general, different data-packet formats can be used with the present inventive system. In one embodiment, the transmitted data packet is 40-bit long, of which 16 bits are used as a synchronization/preamble pattern. The rest 24 bits carry a payload that encodes the IEM's identifier. In one embodiment, the payload can also include a forward error correction (FEC) code so that the transmission is more robust. In one embodiment, a data bit occupies 16 cycles of the carrier clock. The bits are BPSK encoded. Other encoding schemes are also possible. In a further embodiment, the 16-bit synchronization/preamble pattern include 12 bits for synchronization and 4 bits as a preamble.

Table 1 illustrates an exemplary packet format for 16 IEM chips in accordance with one embodiment of the present invention.

TABLE 1

| Chip ID# | Sync | pream | 24 bits payload | broadcast-off mode |
|---|---|---|---|---|
| 0 | 000000000000 | 1010 | 11001011 10001100 10111000 | disabled for 984 bits |
| 1 | 000000000000 | 1010 | 10100101 11001010 01011100 | disabled for 984 bits |
| 2 | 000000000000 | 1010 | 10010010 11101001 00101110 | disabled for 984 bits |
| 3 | 000000000000 | 1010 | 10001001 01111000 10010111 | disabled for 984 bits |
| 4 | 000000000000 | 1010 | 11000100 10111100 01001011 | disabled for 984 bits |
| 5 | 000000000000 | 1010 | 11100010 01011110 00100101 | disabled for 984 bits |

TABLE 1-continued

| Chip ID# | Sync | pream | 24 bits payload | broadcast-off mode |
|---|---|---|---|---|
| 6 | 000000000000 | 1010 | 11110001 00101111 00010010 | disabled for 984 bits |
| 7 | 000000000000 | 1010 | 10111000 10011011 10001001 | disabled for 984 bits |
| 8 | 000000000000 | 1010 | 11011100 01001101 11000100 | disabled for 984 bits |
| 9 | 000000000000 | 1010 | 10010111 00010110 10001110 | disabled for 984 bits |
| 10 | 000000000000 | 1010 | 11001011 10000011 01000111 | disabled for 984 bits |
| 11 | 000000000000 | 1010 | 10100101 11000101 10100011 | disabled for 984 bits |
| 12 | 000000000000 | 1010 | 10010010 11100110 11010001 | disabled for 984 bits |
| 13 | 000000000000 | 1010 | 10001001 01110111 01101000 | disabled for 984 bits |
| 14 | 000000000000 | 1010 | 11000100 10110011 10110100 | disabled for 984 bits |
| 15 | 000000000000 | 1010 | 11100010 01010001 11011010 | disabled for 984 bits |

Figure 5:
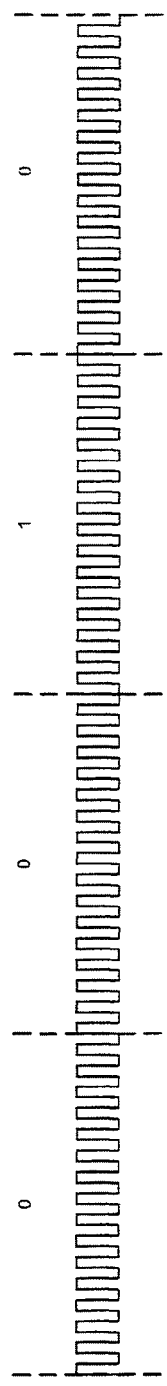
FIG. 5 illustrates an exemplary transmission sequence for a bit pattern of "0010" in accordance with one embodiment of the present invention. Each bit is represented by 16 clock cycles.

FIG. 5 illustrates an exemplary transmission sequence for a bit pattern of "0010" in accordance with one embodiment of the present invention. Each bit is represented by 16 clock cycles. Depending on the battery configuration, it might be desirable to limit drive transistor 306's duty cycle to maintain sufficient power to the oscillator. In one embodiment, the "on" state of drive transistor 306 is maintained to be substantially equal to or less than 25 μs. Thus, during the 20 kHz transmission where a clock cycle is 50 μs, the driver is on for 25 μs and off for 25 μs. During the 10 kHz transmission, the driver is on for 25 μs and off for 75 μs. A logical "0" transmission begins with the rising edge of a data-clock cycle, and lasts for 16 clock cycles). Correspondingly, a logical "1" transmission begins with the falling edge of a data-clock cycle, and also lasts for 16 cycles. Note that other duty-cycle configuration and encoding schemes are also possible.

Figure 6:
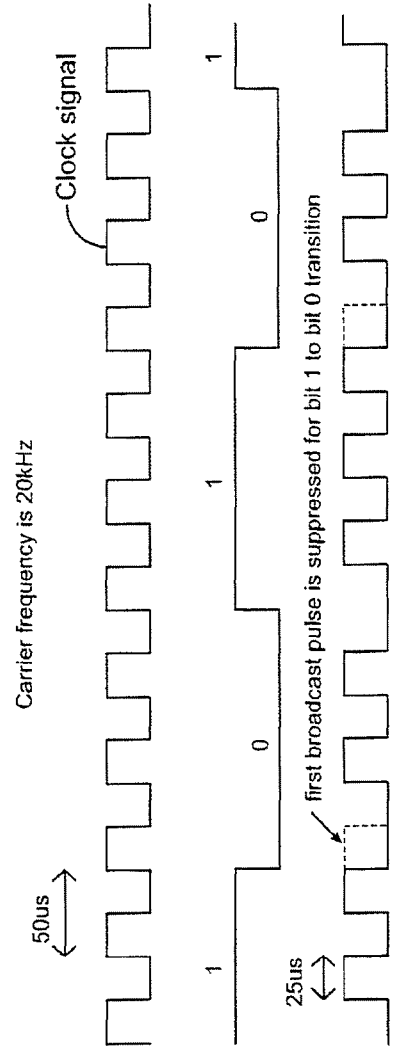
FIG. 6 presents an exemplary waveform for 20 kHz transmission of a sequence "10101" in accordance with one embodiment of the present invention.
Figure 7:
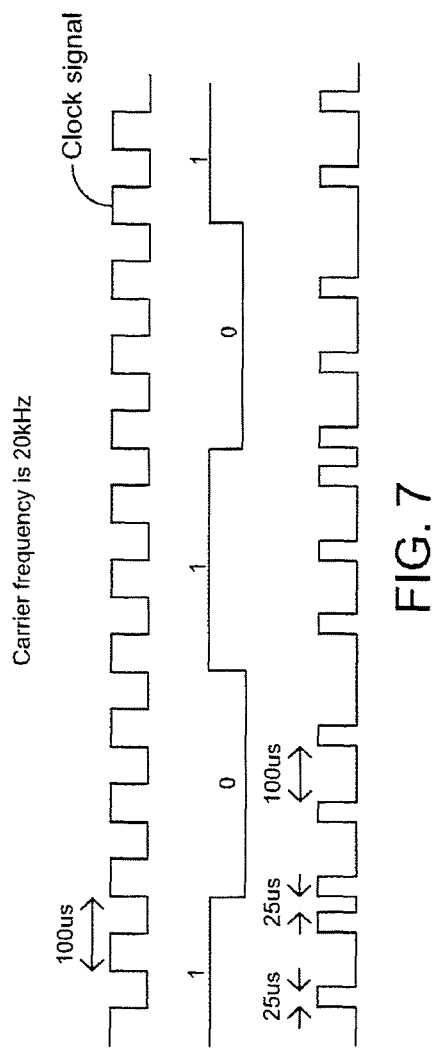
FIG. 7 presents an exemplary waveform of 10 kHz transmission of a sequence "10101" in accordance with one embodiment of the present invention.

FIG. 6 presents an exemplary waveform for 20 kHz transmission of a sequence "10101" in accordance with one embodiment of the present invention. Note that for purposes of illustration, each logical bit occupies 3 clock cycles, instead of 16 cycles. FIG. 7 presents an exemplary waveform of 10 kHz transmission of a sequence "10101" in accordance with one embodiment of the present invention. Note that each logical bit is also shortened to 3 clock cycles.

Figure 8:
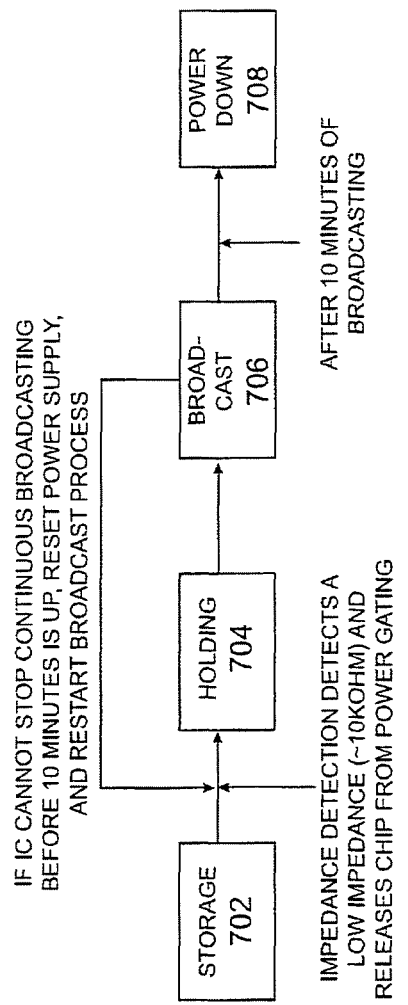
FIG. 8 presents an exemplary state diagram illustrating the operation of an IEM IC in accordance with one embodiment of the present invention.

In certain embodiments, the operation of the IEM can be divided into the following four periods: storage, holding period, broadcast period, and power down. During the storage period, the IC is turned off and typically consumes less than 5 mA. During the holding period, the IC is turned on. However, the broadcast is disabled for the oscillator clock signal to stabilize. In one embodiment, during the broadcast period, a packet is transmitted 256 times. During each transmission, the transmission driver transistor operates to transmit a packet and is then turned off for a period of time. When the transmitter driver transistor is off, the rest of the IEM IC remains powered on. In one embodiment, the average duty cycle during the entire broadcast period is maintained at approximately 3.9%. Other values of the average duty cycle are also possible. During the power-down period, the IEM IC is powered down gracefully. Broadcast is turned off completely. FIG. 8 presents an exemplary state diagram illustrating the operation of a IC in accordance with one embodiment of the present invention. During operation, the system first enters a storage period 702, when an impedance detection circuit operates to detect the impedance between the two battery electrodes. Meantime, the IC is power-gated off. After the impedance detection circuit detects a low impedance, for example an impedance of approximately 10 kOhm, the circuit releases the IEM IC from the power-gated-off state. Correspondingly, the system enters a holding period 704. During holding period 704, the chip's broadcast function is disabled for approximately 10 seconds for the clock signal to stabilize. Next, the system enters a broadcast period 706. During this period, data packets are broadcasted twice in one cycle, one at 10 kHz and one at 20 kHz, with a cycle pattern of ON (10 KHz) for 32 ms-OFF for 768 ms-ON (20 KHz) for 64 ms-OFF for 1536 ms. Each cycle is approximately 2.4 seconds, and the system finishes 256 cycles in approximately 10 minutes. Note that, at each frequency, the chip's transmission duty cycle is maintained at approximately 3.9%. During the remaining 96.1% of the time, the recharge capacitor is recharged. Subsequently, the system enters a power-down state 708, when the oscillator is stopped and the chip is power-gated down. Note that if, for some reason, the chip keeps broadcasting continuously before the end of the 10-minute broadcast period, the system resets the chip's power supply and the broadcast process is started again. Such situation may occur when, for example, the stomach's conductivity suddenly drops so low that the oscillator and its generated clocks cannot function properly.

Table 2 presents a set of exemplary operation parameters for an IC in accordance with one embodiment of the present invention.

TABLE 2

| | Specification | | |
|---|---|---|---|
| Operating Condition | Min | max | Units |
| Operating Temperature | 20 | 45 | C. |
| Storage Temperature | 0 | 60 | C. |
| Storage Humidity | 20% | 90% | Relative |
| Human body conductivity/pH value | 0.01/4 | 1000/11 | $S \cdot m^{-1}$, pH |

Table 3 presents a set of an exemplary IEM circuit's DC parameters in accordance with an embodiment of the present invention.

TABLE 3

| DC | | Specification | | | |
|---|---|---|---|---|---|
| Parameter | Description | Min | Typ | Max | Units |
| Vcc | Power supply for the main chip except the impedance detection circuit, and the output driver. | 1.0 | 1.6 | 1.8 | volts |

TABLE 3-continued

| DC Parameter | Description | Specification Min | Typ | Max | Units |
|---|---|---|---|---|---|
| I(s2) | DC current for the chip during recharging | 8 | 10 | 12 | uA |
| V(s2) | Battery voltage | 1.0 | 1.6 | 1.8 | volts |
| Zon | Output driver's ON-resistance (function of Vbatt.) | 7 | 11 | 55 | Ohms |
| Zoff | Output driver's OFF-resistance. | 75K | 100K | 500k | Ohms |
| Vbattery | Battery voltage when fully wetted | 1.0 | 1.6 | 1.8 | volts |
| Rbattery | Solution's conductivity for Chip to function properly | 500 | 1K-3K | 5K | ohms |

Table 4 presents a set of an exemplary IEM circuit's AC parameters in accordance with an embodiment of the present invention. Note that for actual chip design the targeted value can have +/−5% to +/−10% over temperature, power supply voltage, and transistor's threshold voltage range.

TABLE 4

| | Description | Specification Max | Typ | Min | Units |
|---|---|---|---|---|---|
| f_osc | Oscillator's frequency | 256 | 320 | 384 | kHz |
| f1_broadcast | Low broadcast frequency | 8 | 10 | 12 | kHz |
| f2_broadcast | High broadcast frequency | 16 | 20 | 24 | kHz |
| T_brdcsten | Holding time before enabling chip to do broadcasting at power-on | 8 | 10 | 12 | Sec |
| T_brdcstoff | Time for broadcasting | 8 | 10 | 12 | Minute |
| Signal Amplitude | Signal amplitude = Vbat-(voltage-drop-over-Rbattery) = a strong function of Vbattery and Rbattery. For slow cycle, VCC droops so much that output driver's impedance increase which will reduce the signal's amplitude. Output voltage is the result of voltage divider between Rbatt and ZoutputTRX. | V = 1.6 R = 500 V = 1.6 R = 5K V = 1.2 R = 500 V = 1.2 R = 5K | ~1.57-1.45 ~1.6 (ZoutputTRX can be ignored) ~1.14-1.08 ~1.2 (ZoutputTRX can be ignored) | | volts |

As to a IEM chip's physical size, the chip's dimension can be between 0.1 mm² and 10 mm². Because of the special IC configuration, embodiments of the present invention can provide a IEM chip that is sufficiently small to be included to most types of pills. For example, a IEM IC chip can have a size less than 2×2 mm². In one embodiment, the IC chip can be 1×1 mm² or smaller. In one embodiment, the chip is 1 mm×1 mm. The bottom side of the chip's substrate serves as the S1 electrode, and the S2 is a pad fabricated on the top side of the substrate. The pad's size can be between 2500 μm² and 0.25 mm². In one embodiment, the pad is approximately 85 μm×85 μm.

Although the previous description discloses a chip configuration that uses the same electrodes for battery and signal transmission, in certain embodiments separate electrodes are employed for power generation and signal transmission.

FIG. 9 illustrates one exemplary IEM chip configuration where two separate electrodes are used for battery and signal transmission, respectively. A ground electrode 802 is fabricated on the bottom side of a substrate 800. On the top side of substrate 800 is a battery electrode 804 and a transmission electrode 806. Also fabricated on substrate 800 is a circuitry region 808. During operation, the battery formed by electrodes 802 and 804 provides a power supply to the circuitry within region 808. The circuitry drives transmission electrodes 806 and 802, and produces a current change in the patient's body. It is possible that the current flowing from transmission electrode 806 to ground electrode 802 may flow below the circuitry region 808, causing changes to the electrical potentials in the circuit elements. Such potential changes can cause undesirable latch-ups in the transistors within circuitry region 808.

Figure 11:
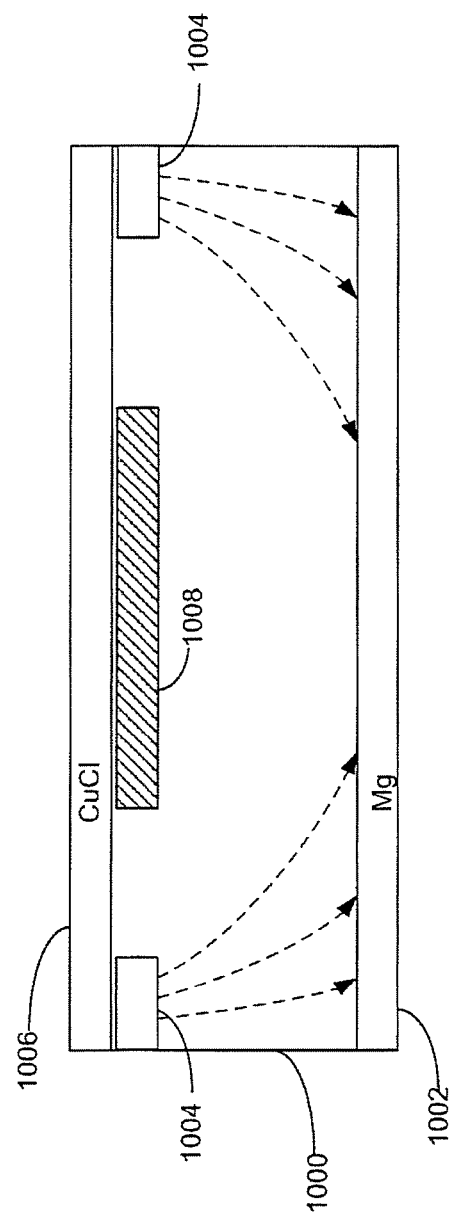
FIG. 11 illustrates an exemplary layout that minimizes latch-ups in an IEM.

One approach to avoid such latch-ups is to separate the transmission-electrode region and the circuitry regions so that there is minimum lateral current flow that would change the potential under the circuits. For example, the substrate contacts can be located in regions that can divert current flow from the circuitry area. FIG. 10 illustrates an exemplary chip configuration that minimizes circuit latch-ups in accordance with one embodiment of the present invention. As shown in FIG. 10, it is possible to place substrate contact regions at the four corners of the substrate. As a result, the electrode current flowing toward the substrate is diverted to the four corners, away from the circuitry region which is in the middle. Similarly, special layout design scan be used for the merged-electrode chip configurations. FIG. 11 illustrates an exemplary layout that minimizes latch-ups in a IEM chip. As shown in FIG. 11, on the bottom of a substrate 1000 is a Mg electrode 1002. On the top side of substrate 1000 is a CuCl electrode 1006. Electrodes 1002 and 1006 serve as both battery electrodes and transmission electrodes. Below CuCl electrode 1006 are a number of transmission driver circuitry regions 1004, which are located at the peripheral of the layout. A control-logic circuitry region 1008 is located at the center of the chip. This way, the current flowing from the transmission drivers toward the Mg electrode 1002 is diverted away from the control-logic circuitry region 1008, thereby avoiding any latch-ups in the transistors.

Figure 12:
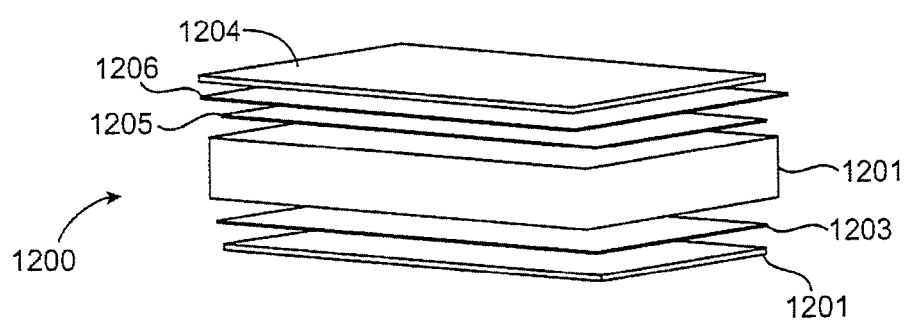
FIG. 12 provides an exploded view of an IEM according to an embodiment of the invention.

FIG. 12 provides an exploded view of a specific embodiment of an IEM in accordance with the invention. In FIG. 12, IEM 1200 includes silicon dioxide substrate 1201, e.g., having a thickness of 300 μm. Present on bottom surface is electrode layer of Magnesium 1202, e.g., having a thickness of 8 μm. Positioned between Mg electrode layer 1202 and bottom surface of substrate 1201 is titanium layer 1203, e.g., having a thickness of 1000 Å. Positioned on upper surface of substrate 1201 is electrode layer (CuCl) 1204, e.g., having a thickness of 6 μm. Positioned between upper electrode layer 1204 and substrate 1201 is titanium layer 1205, e.g., having a thickness of 1000 Å, and gold layer 1206, e.g., have a thickness of 5 μm.

While the signal generation and emission protocol above has been described in terms of activation and transmission occurring at substantially the same time, e.g., following contact with target site and/or environment, in certain embodiments the activation of the IEM and transmission of the signal can be separate events, i.e., that may occur at distinct times separated by some duration. For example, an IEM may include a conducting medium that provides for activation prior to ingestion. In certain embodiments, the IEM is encapsulated in a fluid, electrolyte sponge, or other conducting media such that it can be activated externally prior to digestion. In these embodiments, the receiver is configured to detect a transmitted signal only when the signal is transmitted from the target site of interest. For example, the system may be configured so that transmission will only occur upon contact with body tissue insuring proper event marking. For example, activation can occur with handling of the IEM. Pressure sensitive membranes that break with handling or contact may be employed, where braking causes electrolyte material to enable connection of the battery elements. Alternatively, degradation of the gel capsule in the stomach can also release stored electrolyte and activate the IEM. Encapsulating the IEM in a sponge (composed of conducting material which retains water close to the IEM) allows for activation to occur in the presence of small amounts of liquid. This configuration counteracts poor transmission performance in the absence of conducting fluids.

Note that other layout designs are also possible. In addition, silicon-over-insulator (SOI) fabrication techniques can be used to insulate the logic-control circuitry region from the conductive substrate, so that the transmission current cannot interfere with the control circuit.

In certain embodiments, the identifier compositions are disrupted upon administration to a subject. As such, in certain embodiments, the compositions are physically broken, e.g., dissolved, degraded, eroded, etc., following delivery to a body, e.g., via ingestion, injection, etc. The compositions of these embodiments are distinguished from devices that are configured to be ingested and survive transit through the gastrointestinal tract substantially, if not completely, intact.

In certain embodiments, the identifiers do not include an imaging system, e.g., camera or other visualization or imaging element, or components thereof, e.g., CCD element, illumination element, etc. In certain embodiments, the identifiers do not include a sensing element, e.g., for sensing a physiological parameter, beyond the activator which detects contact with the targeted physiological site. In certain embodiments, the identifiers do not include a propulsion element. In certain embodiments, the identifiers do not include a sampling element, such as a fluid retrieval element. In certain embodiments, the identifiers do not include an actuatable active agent delivery element, such as an element that retains an active agent with the composition until a signal is received that causes the delivery element to release the active agent.

The identifiers may be fabricated using any convenient processing technology. In certain embodiments, planar processing protocols are employed to fabricate power sources having surface electrodes, where the surface electrodes include at least an anode and cathode at least partially on the same surface of a circuitry support element. In certain embodiments, planar processing protocols are employed in a wafer bonding protocol to produce a battery source. Planar processing techniques, such as Micro-Electro-Mechanical Systems (MEMS) fabrication techniques, including surface micromachining and bulk micromachining techniques, may be employed. Deposition techniques that may be employed in certain embodiments of fabricating the structures include, but are not limited to: electrodeposition (e.g., electroplating), cathodic arc deposition, plasma spray, sputtering, e-beam evaporation, physical vapor deposition, chemical vapor deposition, plasma enhanced chemical vapor deposition, etc. Material removal techniques included, but are not limited to: reactive ion etching, anisotropic chemical etching, isotropic chemical etching, planarization, e.g., via chemical mechanical polishing, laser ablation, electronic discharge machining (EDM), etc. Also of interest are lithographic protocols. Of interest in certain embodiments is the use of planar processing protocols, in which structures are built up and/or removed from a surface or surfaces of an initially planar substrate using a variety of different material removal and deposition protocols applied to the substrate in a sequential manner. Illustrative fabrication methods of interest are described in greater detail in copending PCT application serial no. PCT/US2006/016370; the disclosure of which is herein incorporated by reference.

In certain fabrication protocols, a sacrificial layer is used. For example, in certain three-dimensional embodiments, such as ones described in greater detail below, where gaps or spaces are desired, sacrificial layers may be employed during fabrication, where such layers are removed in whole or in part prior to use of the battery. Sacrificial layer materials of interest include, but are not limited to, photoresists which can be hard baked to make them stable processing. The photoresist sacrificial layer can be removed using any convenient protocol, e.g., with acetone, once the deposition of the top electrode is complete. Other materials that can be used as a sacrificial layer include, but are not limited to, a silicon nitride, silicon dioxide, benzocyclobutene or tungsten. Other methods of removing the sacrificial layer include but are not limited to gas phase removal, dry etch removal and hydrogen peroxide.

As mentioned above, in certain embodiments planar processing, e.g., MEMS, fabrication protocols are employed to fabricate batteries that include an anode and cathode that are at least partially present on the same surface of a circuitry support element. By "least partially present on the same surface of a circuitry support element" is meant that at least a portion of a cathode and at least a portion of anode are present on the same surface of a circuitry support element, where both electrodes may be entirely present on the surface of the circuitry support element, one electrode may be wholly present on a surface and the other electrode only partially present on surface, e.g., where the other electrode includes a portion that is present on a different surface than the surface on which the first electrode is positioned, and where both electrodes are partially present on the same surface and then partially present on different surfaces. The implantable on-chip battery can be deposited on the chip in a variety of ways. The circuitry support element may take any convenient configuration, and in certain embodiments is an integrated circuit (IC) chip. The surface upon which the electrode elements are positioned may be the top surface, bottom surface or some other surface, e.g., side surface, as desired, where in certain embodiments the surface upon which the electrode elements are at least partially present is a top surface of an IC chip.

Using MEMS fabrication techniques, batteries of embodiments of the invention can be manufactured to be very small size, e.g., as reviewed above. The electrodes of the batteries can be deposited in a variety of thicknesses, e.g., ranging from about 0.001 to about 1000 µm, such as from about 0.5 to about 10 µm. Where gaps are present between electrodes, the gaps may have a width ranging from about 0.001 to about 1000 µm, such as from about 1 to about 10 µm.

Figure 30:
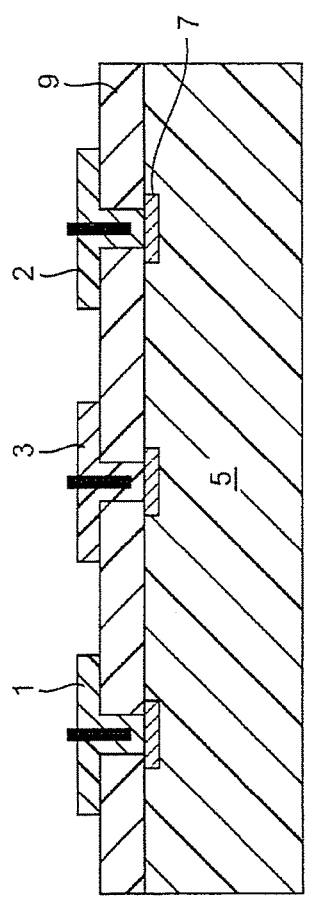
FIG. 30 shows one embodiment of the planar or interdigitated configuration of the implantable on-chip battery with two cathodes and one anode.

In one embodiment two cathodes are deposited on the surface of a chip with an anode separating the two cathodes. A dielectric layer is deposited in between the electrodes and the circuit chip with circuit contacts penetrating the chip surface. This configuration allows multiple batteries to be put into series which provides for a greater voltage to be applied to the circuit chip upon activation of the battery by contact with the target site. FIG. 30 shows a planar, inter-digitated battery layout. The dielectric material 9 is deposited on the circuit chip 5 which contains the circuit contacts 7. The anode 3 separates the first cathode 1 from the second cathode 2. Embodiments employing this configuration include ones in which batteries are in series (e.g., as described above), which provides for higher voltages that may be used by the circuit upon contact with the target physiological site. In certain embodiments, this configuration also provides for low battery impedance because the electrodes are placed so closely together. This embodiment is characterized in that both the cathode and anode elements are wholly present on the same surface of the chip.

Figure 31:
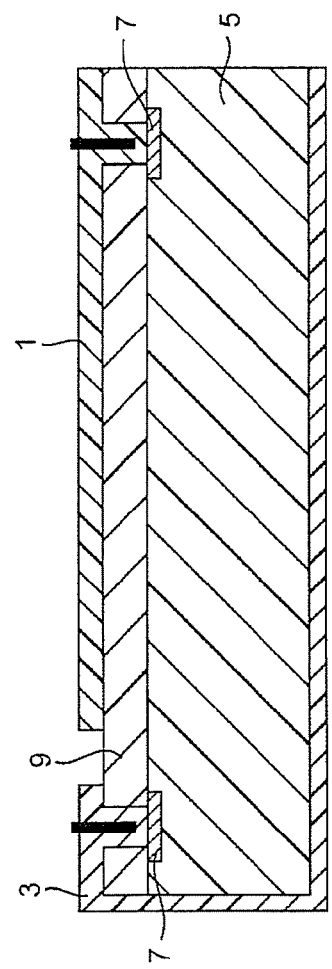
FIG. 31 shows one embodiment of the large plate configuration of the implantable on-chip battery.

In another embodiment, at least one of the anode and cathode elements is partially present on the same surface as the other electrode, but also partially present on another surface, e.g., side, bottom, etc., of the chip. For example, the anode may be present on a small portion of one side of the surface of the circuit chip and wrap around that side to cover the bottom of the circuit chip. The cathode is present on the remainder of the top surface of the circuit chip, and a small gap is provided between the cathode and the anode. In one aspect, a large cathode plate covers a majority of the top surface of the circuit chip while the anode covers the bottom surface of the circuit chip and wraps around the side to the top surface. Both electrodes, e.g., plates, can be connected to the circuit chip via a circuit contact through the dielectric layer on the top surface of the chip. FIG. 31 shows the dielectric material 9 covering the circuit chip 5. Cathode 1 is deposited over a majority of the top surface of the dielectric material 9. The anode 3 is deposited over the remainder of the top surface as well as the side and bottom surfaces of the circuit chip 5 saving a separation between the cathode 1 and anode 3 on the top. In certain embodiments, the separation ranges from about 0.001 to about 1000 µm, such as from about 0.1 to about 100 µm, e.g., about 2.0 µm. In certain embodiments, the circuit chip 5 may be flipped during fabrication in order to deposit the anode 3 on the bottom surface of the chip 5. Circuit contacts 7 for both the anode 3 and cathode 1 are provided on the top surface of the circuit chip 5, traveling down through the dielectric 9. This configuration provides a very large electrode area since it utilizes both the top and bottom of the circuit chip 5 as well as one of the sides.

Figure 32:
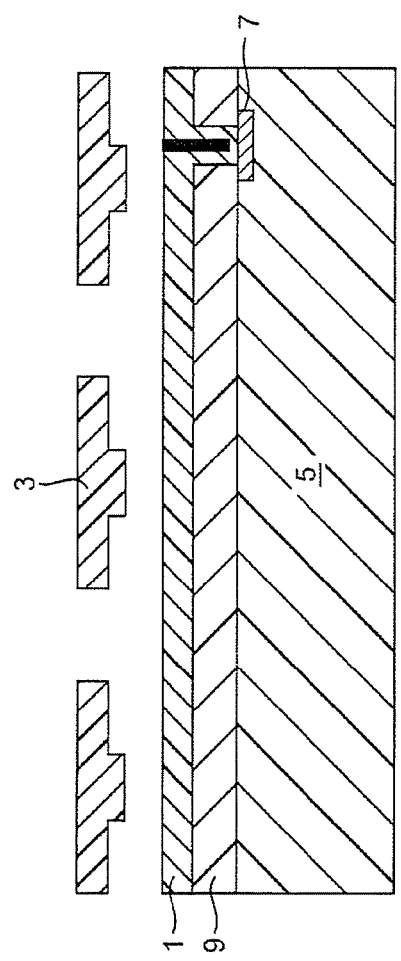
FIG. 32 shows one embodiment of the 3-d configuration of the implantable on-chip battery with three anodes bridged over the cathode.

In another embodiment, a cathode is positioned on a top surface of a circuit chip, e.g., present as a layer that has been deposited over a dielectric on the top surface of the circuit chip. During fabrication, a sacrificial layer is then deposited on top of the cathode layer. An anode layer is then deposited on top of the sacrificial layer. The sacrificial layer can then be removed leaving a gap which provides an area for target site fluids, e.g., electrolytic stomach fluids, to contact the anode and cathode. Using this embodiment, additional electrode layers can be stacked on top of one another after depositing another sacrificial layer on top of the anode. In doing so, the implantable on-chip battery can be put into series, e.g., where a vertical series configuration is desired. FIG. 32 shows dielectric layer 9 disposed on top of circuit chip 5. The cathode 1 is deposited on top of dielectric layer 9 and through to the circuit contact 7. A sacrificial layer (not shown) is deposited on top of the cathode 1 to provide a base for the anodes 3 to be deposited. Once the sacrificial layer is deposited, its surface can be etched to provide a rougher surface. Therefore, when the anodes 3 are deposited onto the sacrificial layer, the bottom of the anodes 3 will conform to a rough surface. The sacrificial layer could also be deposited using cathodic arc, which would deposit it in a rough and porous manner. Multiple anodes 3 can be deposited in multiple sizes to provide multiple voltages to the chip circuit 5. Once the anodes 3 are deposited, the sacrificial layer can be removed to create a gap, where in certain embodiments the gap ranges from about 0.001 to about 1000 µm, such as from about 0.1 to about 100 µm, and including from about 1 to about 10 µm. In certain embodiments, the gab between the anodes 3 and the cathode 1 is chosen to provide a battery with desired impedances and different currents. The areas of the anodes 3 can also be manufactured to provide different voltages to the circuit chip 5, as desired. Therefore, the anodes 3 can be manufactured to provide multiple voltages with multiple impedances and currents for the same chip, with minimal use of chip space.

Figure 33:
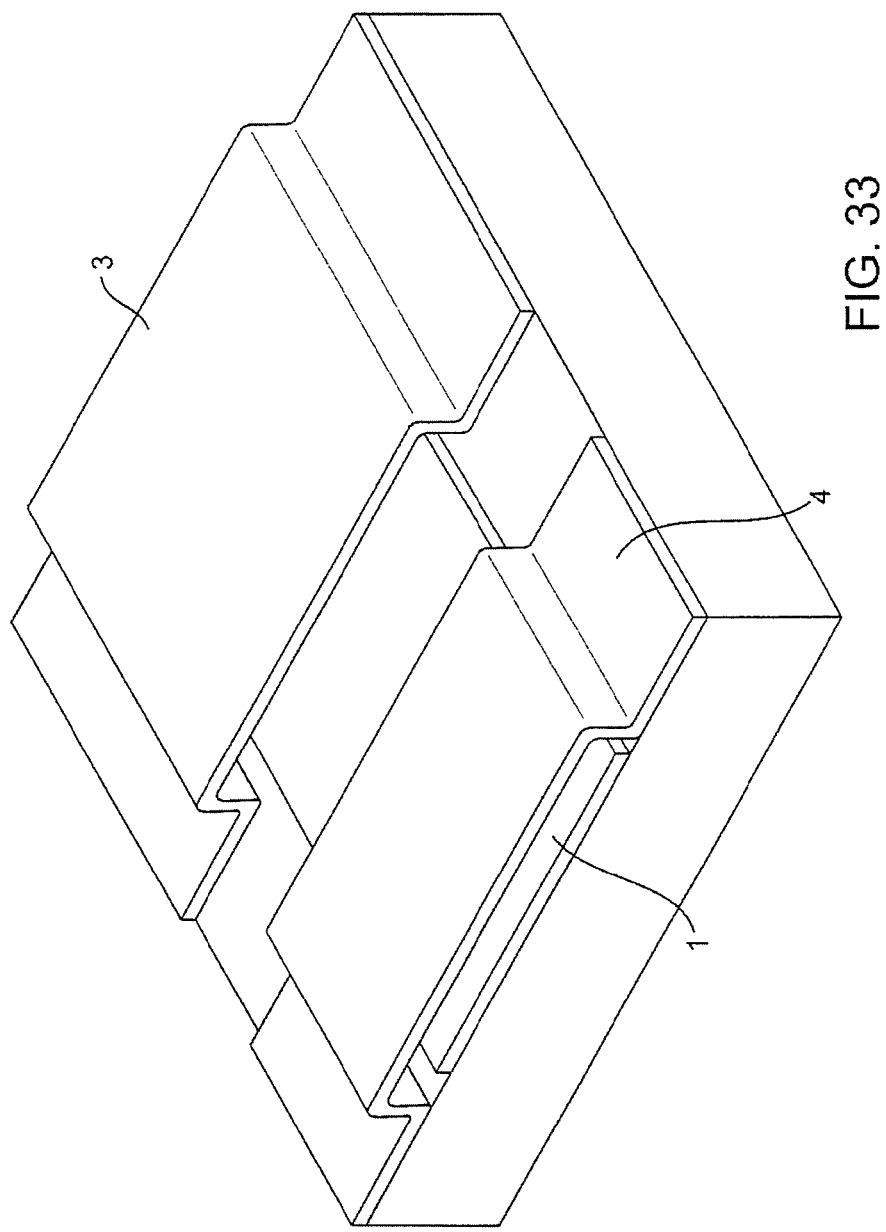
FIG. 33 is another view of an embodiment of the 3-d configuration of the implantable on-chip battery.

In another embodiment, a cathode layer is deposited over the dielectric on the surface of the chip, and multiple anodes are deposited over different areas of the cathode. A sacrificial layer is deposited to separate the anodes from the cathode during fabrication, and upon removal produces a gap between the common cathode and two or more anodes positioned over the cathode. As can be seen in FIG. 33, the anode 3 may be anchored to the outer area of the circuit chip 5. It is at that point 4 where the circuit contact for the anode 3 may be placed. FIG. 33 differs from FIG. 32 in that only two anodes 3 are deposited above the cathode 1. The two anodes 3 are also different sizes, and therefore provide different surface areas. The anodes 3 can be manufactured to meet the requirements of the application. If multiple voltages are desired, the anodes 3 can be manufactured out of different materials. If multiple currents are desired, the anodes 3 can be deposited in multiple sizes. If multiple impedances are desired, the anodes 3 can be deposited with different sized gaps between the anodes 3 and the cathode 1.

Figure 34:
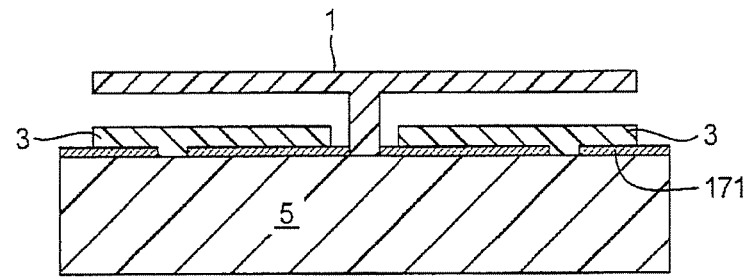
FIG. 34 is another embodiment of the implantable on-chip battery.

In another embodiment, two anode plates are present on the surface of the circuit chip with a cathode circuit contact deposited in the middle of the surface. The cathode is then attached to the circuit contact in a way such that it hangs over the anodes, thereby forming a gap between the cathode and anode. FIG. 34 shows another embodiment of the implantable on-chip capacitor that utilizes the space above the circuit chip 5. An insulating layer 171 is formed on the surface of the circuit chip 5. The circuit contact for the cathode 1 is formed at the center of the chip with anodes 3 formed at either side leaving a gap between the circuit contact and the anodes 3. During fabrication, a sacrificial layer is then deposited on top of the anodes 3 to form a base for the cathode 1. Once the cathode 1 is deposited, the sacrificial layer is removed providing a space for the liquid to enter.

Figure 35:
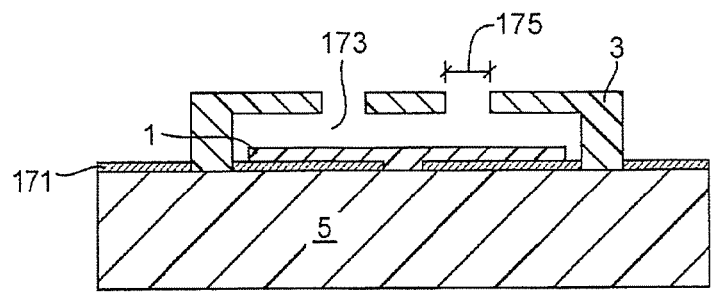
FIG. 35 is another embodiment of the implantable on-chip battery.

In another embodiment, a cathode is present on the surface of the circuit chip with an anode positioned in a manner sufficient to provide an open chamber above and at least partially around the cathode. Openings are provided that allow electrolytic fluid to flow into the chamber, which produces a current path between the anode and the cathode. Multiple openings may be provided as desired, e.g., in order to ensure that no air gets trapped inside of the chamber. In FIG. 35, the anode 3 surrounds the cathode 1 creating a chamber 173 into which an electrolytic fluid will enter. An insulating layer 11 separates the cathode 1 from the circuit chip 5. Upon contact with the target site, the electrolytic fluid will enter the chamber 173 through the openings 175. The openings 175 may be situated in opposite corners of the chamber 173 to make sure that no air gets trapped inside. The configuration of FIG. 35 may be desirable in certain instances. For instances when there may not be an abundant amount of electrolytic fluid present in the stomach, the implantable on-chip battery can be fabricated to contain the fluid it comes in contact with around the electrodes, e.g., as shown in FIG. 35. By doing so the battery would be assured of having a continuous reaction whereas, if it were open, the fluid may enter and exit the reaction area and cause the battery to stop.

Where a given battery unit includes a chamber, e.g., as shown in FIG. 35, surface coating to modulate fluid flow into and out of the chamber may be employed, as desired. In certain embodiments, the surface of a portion of the chamber, e.g., an interior surface of the chamber, may be modified to provide for desired fluid flow properties. For example, the surface energy of one or more surfaces of the chamber and fluid ports may be modified to provide for enhanced fluid flow into the chamber. For example, the surface energy of one or more surfaces of the chamber may be increased, such that the surface becomes more hydrophilic. A variety of different surface energy modification protocols may be employed, where the particular protocol chosen may depend on the particular composition of the barrier and the desired surface energy properties. For example, if one wishes to increase the surface energy of a given surface, the surface may be subjected to plasma treatment, contacted with a surface energy modification such as surface modifying polymer solutions described in, e.g., U.S. Pat. Nos. 5,948,227 and 6,042,710, each of which is incorporated herein in its entirety for all purposes. In certain embodiments, a hydrophilic substance may be employed to attract and retain the electrolytic fluid within the chamber, e.g., as described in PCT application serial no. PCT/US07/82563, the disclosure of which is herein incorporated by reference.

In certain embodiments, one or more surfaces of the battery, e.g., interior surfaces of a chamber, are modified to modulate gas bubble formation and positioning on the surface. For example, activation of a battery may result in bubble production, e.g., hydrogen gas bubble production. Surface modification may be employed so that bubbles produced during activation, e.g., on the active cathode, are drawn from the cathode to another location, e.g., away from the cathode, outside of the chamber, etc.

The above embodiments are examples of the inventive planar processing protocol produced batteries in which at least one anode and at least one cathode are present on the same surface of a circuitry support element. The above description is in no way limiting, as other embodiments may be produced which have the above common characteristic.

Figure 36:
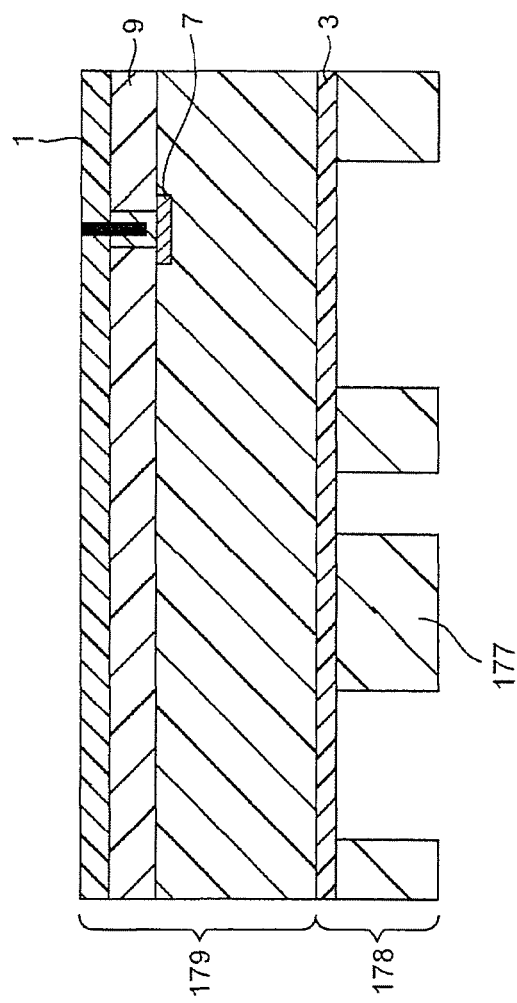
FIG. 36 is another embodiment of the implantable on-chip battery that uses wafer bonding as the fabrication method.

In another embodiment of the invention, planar processing protocols are employed in a wafer bonding protocol to produce a battery source. In certain of such embodiments, a dielectric can be deposited on a circuit chip. A cathode layer can then be deposited on top of the dielectric. An anode can be deposited on a separate support wafer. The anode may then be bonded to the bottom of the circuit chip at which point the support wafer can be etched out to allow the anode surface to come in contact with the electrolytic fluid. As such, another fabrication technique that can be used in making the implantable on-chip battery is wafer bonding. The implantable on-chip battery can be manufactured using two wafers, such as in the embodiment of FIG. 36. The circuit chip 5 provides the base for the cathode 1, which is deposited on top of a dielectric 9. This composes the first wafer assembly 179. The second wafer assembly 178 is comprised of a support wafer 177 and the anode 3. The anode 3 is deposited on the surface of the support wafer 177. The anode 3 is then bonded to the circuit chip 5 and the bulk support wafer 177 is etched away exposing areas of the anode 3. The amount of the support wafer 177 that is etched away is dependent on the areas that are desired for the anode 3. This fabrication method can be useful for the implantable on-chip battery because if more circuitry is desired it can be placed in the support wafer 177.

All of the embodiments and figures discussed above can be altered to switch a cathode with an anode and vice versa, providing yet additional disclosed configurations of the invention. Additional planar process fabricated embodiments of interest include those described in U.S. Provisional Application Ser. No. 60/889,868; the disclosure of which is herein incorporated by reference.

Optional Physiologically Acceptable Carrier Component

In addition to the identifier component described above, the ingestible event markers may be present in (i.e., combined with) a physiologically acceptable carrier component, e.g., a composition or vehicle that aids in ingestion of the identifier and/or protects the identifier until it reaches the target site of interest. By physiologically acceptable carrier component" is meant a composition, which may be a solid or fluid (e.g., liquid), which has is ingestible.

Common carriers and excipients, such as corn starch or gelatin, lactose, dextrose, sucrose, microcrystalline cellulose, kaolin, mannitol, dicalcium phosphate, sodium chloride, and alginic acid are of interest. Disintegrators commonly used in the formulations of the invention include croscarmellose, microcrystalline cellulose, corn starch, sodium starch glycolate and alginic acid.

A liquid composition may comprise a suspension or solution of the compound or pharmaceutically acceptable salt in a suitable liquid carrier(s), for example, ethanol, glycerine, sorbitol, non-aqueous solvent such as polyethylene glycol, oils or water, with a suspending agent, preservative, surfactant, wetting agent, flavoring or coloring agent. Alternatively, a liquid formulation can be prepared from a reconstitutable powder. For example, a powder containing active compound, suspending agent, sucrose and a sweetener can be reconstituted with water to form a suspension; and a syrup can be prepared from a powder containing active ingredient, sucrose and a sweetener.

A composition in the form of a tablet or pill can be prepared using any suitable pharmaceutical carrier(s) routinely used for preparing solid compositions. Examples of such carriers include magnesium stearate, starch, lactose, sucrose, microcrystalline cellulose and binders, for example, polyvinylpyrrolidone. The tablet can also be provided with a color film coating, or color included as part of the carrier(s). In addition, active compound can be formulated in a controlled release dosage form as a tablet comprising a hydrophilic or hydrophobic matrix.

"Controlled release", "sustained release", and similar terms are used to denote a mode of active agent delivery that occurs when the active agent is released from the delivery vehicle at an ascertainable and controllable rate over a period of time, rather than dispersed immediately upon application or injection. Controlled or sustained release may extend for hours, days or months, and may vary as a function of numerous factors. For the pharmaceutical composition of the present invention, the rate of release will depend on the type of the excipient selected and the concentration of the excipient in the composition. Another determinant of the rate of release is the rate of hydrolysis of the linkages between and within the units of the polyorthoester. The rate of hydrolysis in turn may be controlled by the composition of the polyorthoester and the number of hydrolysable bonds in the polyorthoester. Other factors determining the rate of release of an active agent from the present pharmaceutical composition include particle size, acidity of the medium (either internal or external to the matrix) and physical and chemical properties of the active agent in the matrix.

A composition in the form of a capsule can be prepared using routine encapsulation procedures, for example, by incorporation of active compound and excipients into a hard gelatin capsule. Alternatively, a semi-solid matrix of active compound and high molecular weight polyethylene glycol can be prepared and filled into a hard gelatin capsule; or a solution of active compound in polyethylene glycol or a suspension in edible oil, for example, liquid paraffin or fractionated coconut oil can be prepared and filled into a soft gelatin capsule.

Tablet binders that can be included are acacia, methylcellulose, sodium carboxymethylcellulose, poly-vinylpyrrolidone (Povidone), hydroxypropyl methyl-cellulose, sucrose, starch and ethylcellulose. Lubricants that can be used include magnesium stearate or other metallic stearates, stearic acid, silicone fluid, talc, waxes, oils and colloidal silica.

Flavoring agents such as peppermint, oil of wintergreen, cherry flavoring or the like can also be used. Additionally, it may be desirable to add a coloring agent to make the dosage form more attractive in appearance or to help identify the product.

Other components suitable for use in the formulations of the present invention can be found in Remington's Pharmaceutical Sciences, Mace Publishing Company, Philadelphia, Pa., 17th ed. (1985).

Optional Active Agent

In certain embodiments, the ingestible event marker does not include a pharmaceutically active agent. As such, the identifier, and any carrier or other component that make up the ingestible event marker, do not include an active agent.

In yet other embodiments, the ingestible event marker includes an active agent. By "active agent/carrier component" is meant a composition, which may be a solid or fluid (e.g., liquid), which has an amount of active agent, e.g., a dosage, present in a pharmaceutically acceptable carrier. The active agent/carrier component may be referred to as a "dosage formulation."

"Active agent" includes any compound or mixture of compounds which produces a physiological result, e.g., a beneficial or useful result, upon contact with a living organism, e.g., a mammal, such as a human. Active agents are distinguishable from such components as vehicles, carriers, diluents, lubricants, binders and other formulating aids, and encapsulating or otherwise protective components. The active agent may be any molecule, as well as binding portion or fragment thereof, that is capable of modulating a biological process in a living subject. In certain embodiments, the active agent may be a substance used in the diagnosis, treatment, or prevention of a disease or as a component of a medication. In certain embodiments, the active agent may be a chemical substance, such as a narcotic or hallucinogen, which affects the central nervous system and causes changes in behavior.

The active agent (i.e., drug) is capable of interacting with a target in a living subject. The target may be a number of different types of naturally occurring structures, where targets of interest include both intracellular and extracellular targets. Such targets may be proteins, phospholipids, nucleic acids and the like, where proteins are of particular interest. Specific proteinaceous targets of interest include, without limitation, enzymes, e.g., kinases, phosphatases, reductases, cyclooxygenases, proteases and the like, targets comprising domains involved in protein-protein interactions, such as the SH2, SH3, PTB and PDZ domains, structural proteins, e.g., actin, tubulin, etc., membrane receptors, immunoglobulins, e.g., IgE, cell adhesion receptors, such as integrins, etc., ion channels, transmembrane pumps, transcription factors, signaling proteins, and the like.

The active agent (i.e., drug) may include one or more functional groups necessary for structural interaction with the target, e.g., groups necessary for hydrophobic, hydrophilic, electrostatic or even covalent interactions, depending on the particular drug and its intended target. Where the target is a protein, the drug moiety may include functional groups necessary for structural interaction with proteins, such as hydrogen bonding, hydrophobic-hydrophobic interactions, electrostatic interactions, etc., and may include at least an amine, amide, sulfhydryl, carbonyl, hydroxyl or carboxyl group, such as at least two of the functional chemical groups.

Drugs of interest may include cyclical carbon or heterocyclic structures and/or aromatic or polyaromatic structures substituted with one or more of the above functional groups. Also of interest as drug moieties are structures found among biomolecules, including peptides, saccharides, fatty acids, steroids, purines, pyrimidines, derivatives, structural analogs or combinations thereof. Such compounds may be screened to identify those of interest, where a variety of different screening protocols are known in the art.

The active agent may be derived from a naturally occurring or synthetic compound that may be obtained from a wide variety of sources, including libraries of synthetic or natural compounds. For example, numerous means are available for random and directed synthesis of a wide variety of organic compounds and biomolecules, including the preparation of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

As such, the active agent may be obtained from a library of naturally occurring or synthetic molecules, including a library of compounds produced through combinatorial means, i.e., a compound diversity combinatorial library. When obtained from such libraries, the drug moiety employed will have demonstrated some desirable activity in an appropriate screening assay for the activity. Combinatorial libraries, as well as methods for producing and screening such libraries, are known in the art and described in: U.S. Pat. Nos. 5,741,713; 5,734,018; 5,731,423; 5,721,099; 5,708,153; 5,698,673; 5,688,997; 5,688,696; 5,684,711; 5,641,862; 5,639,603; 5,593,853; 5,574,656; 5,571,698; 5,565,324; 5,549,974; 5,545,568; 5,541,061; 5,525,735; 5,463,564; 5,440,016; 5,438,119; 5,223,409, the disclosures of which are herein incorporated by reference.

Broad categories of active agents of interest include, but are not limited to: cardiovascular agents; pain-relief agents, e.g., analgesics, anesthetics, anti-inflammatory agents, etc.; nerve-acting agents; chemotherapeutic (e.g., anti-neoplastic) agents; etc.

Personal Signal Receivers

As reviewed above, in addition to the IEM, the systems of the invention include signal receivers configured to receive a signal from the identifier of the IEM, i.e., to receive a signal emitted by the IEM upon contact of the IEM with the target physiological site following ingestion of the IEM. The signal receiver may vary significantly depending on the nature of the signal that is generated by the signal generation element, e.g., as reviewed below. As such, the signal receiver may be configured to receive a variety of different types of signals, including but not limited to: RF signals, magnetic signals, conductive (near field) signals, acoustic signals, etc., as indicated above.

In certain embodiments, the receiver is configured to receive a signal conductively from another component, e.g., the identifier of an IEM, such that the two components use the body of the patient as a communication medium. As such, the signal that is transferred between identifier of the IEM and the receiver travels through the body, and requires the body as the conduction medium. The identifier emitted signal may be transmitted through and received from the skin and other body tissues of the subject body in the form of electrical alternating current (a.c.) voltage signals that are conducted through the body tissues. As a result, such embodiments do not require any additional cable or hard wire connection, or even a radio link connection for transmitting the sensor data from the autonomous sensor units to the central transmitting and receiving unit and other components of the system, since the sensor data are directly exchanged via the skin and other body tissues of the subject. This communication protocol has the advantage that the receivers may be adaptably arranged at any desired location on the body of the subject, whereby the receivers are automatically connected to the required electrical conductor for achieving the signal transmission, i.e., the signal transmission is carried out through the electrical conductor provided by the skin and other body tissues of the subject. Where the receivers include sensing elements (see below), one may have a plurality of receiver/sensor elements distributed throughout the body and communicating with each other via this body conductive medium protocol. Such a body-based data transmission additionally has the advantage that the transmitting power required therefore is extremely small. This avoids the generation of interference in the electrical operation of other devices, and also helps to prevent the unintended interception or tapping and surveillance of the sensitive medical data. The resulting very low power consumption is additionally advantageous for achieving the goal of a long-term monitoring, especially in applications having a limited power supply.

The signal receiver is configured to receive a signal from an identification element of an IEM. As such, the signal receiver is configured so that it can recognize a signal emitted from an identifier of an IEM. In certain embodiments, the signal detection component is one that is activated upon detection of a signal emitted from an identifier. In certain embodiments, the signal receiver is capable of (i.e., configured to) simultaneously detecting multiple pharma-informatics enabled compositions, e.g., 2 or more, 5 or more, 10 or more, etc.

The signal receiver may include a variety of different types of signal receiver elements, where the nature of the receiver element necessarily varies depending on the nature of the signal produced by the signal generation element. In certain embodiments, the signal receiver may include one or more electrodes (e.g., 2 or more electrodes, 3 or more electrodes, includes multiple, e.g., 2 or more, 3 or more, 4 or more pairs of electrodes, etc.) for detecting signal emitted by the signal generation element. In certain embodiments, the receiver device will be provided with two electrodes that are dispersed at a distance, e.g., a distance that allows the electrodes to detect a differential voltage. This distance may vary, and in certain embodiments ranges from about 0.1 to about 5 cm, such as from about 0.5 to about 2.5 cm, e.g., about 1 cm. In certain embodiments, the first electrode is in contact with an electrically conductive body element, e.g., blood, and the second electrode is in contact with an electrically insulative body element relative to said conductive body element, e.g., adipose tissue (fat). In an alternative embodiment, a receiver that utilizes a single electrode is employed. In certain embodiments, the signal detection component may include one or more coils for detecting signal emitted by the signal generation element. In certain embodiments, the signal detection component includes an acoustic detection element for detecting signal emitted by the signal generation element. In certain embodiments, multiple pairs of electrodes (e.g., as reviewed above) are provided, for example to increase detection probability of the signal.

The signal receivers of interest include both external and implantable signal receivers. In external embodiments, the signal receiver is ex vivo, by which is meant that the receiver is present outside of the body during use. Where the receiver is implanted, the signal receiver is in vivo. The signal receiver is configured to be stably associated with the body, e.g., either in vivo or ex vivo, at least during the time that it receives the emitted signal from the IEM.

In the broadest sense, receivers of the invention may be either mobile or immobile relative to the patient for which they are configured to operate. Mobile embodiments of the signal receiver include ones that are sized to be stably associated with a living subject in a manner that does not substantially impact movement of the living subject. As such, embodiments the signal receiver have dimensions that, when employed with a subject, such as a human subject, will not cause the subject to experience any difference in its ability to move. In these embodiments, the receiver is dimensioned such that its size does not hinder the ability of the subject to physically move.

In certain embodiments, the signal receivers can be configured to have a very small size. Where the signal receiver has a small size, in certain embodiments the signal receiver occupies a volume of space of about 5 $cm^3$ or less, such as about 3 $cm^3$ or less, including about 1 $cm^3$ or less. In certain embodiments, the desired functionality of the signal receiver is achieved with one rechargeable battery.

In addition to receiving a signal from an identifier of an ingestible event marker, the signal receiver may further include one or more distinct physiological parameter sensing abilities. By physiological parameter sensing ability is meant a capability of sensing a physiological parameter or biomarker, such as, but not limited to: heart rate, respiration rate, temperature, pressure, chemical composition of fluid, e.g., analyte detection in blood, fluid state, blood flow rate, accelerometer motion data, IEGM (intra cardiac electrogram) data, etc. Where the signal receiver has physiological parameter or biomarker sensing capability, the number of distinct parameters or biomarkers that the signal receiver may sense may vary, e.g., 1 or more, 2 or more, 3 or more, 4 or more, 5 or more, 10 or more, etc. The term "biomarker" refers to an anatomic, physiologic, biochemical, or molecular parameter associated with the presence and severity of specific disease states. Biomarkers are detectable and measurable by a variety of methods including physical examination, laboratory assays and medical imaging. Depending on the particular embodiment, the signal receiver may accomplish one or more of these sensing functions using the signal receiving element, e.g., using electrodes of the receiver for signal receiving and sensing applications, or the signal receiver may include one or more distinct sensing elements that are different from the signal receiving element. The number of distinct sensing elements that may be present on (or at least coupled to) the signal receiver may vary, and may be 1 or more, 2 or more, 3 or more, 4 or more, 5 or more, 10 or more, etc.

In certain embodiments, the signal receiver includes a set of 2 or more electrodes that provide for dual functions of signal receiving and sensing. For example, in addition to receiving signal, the electrodes can also serve additional sensing functions. In certain embodiments, the electrodes are used to generate electrocardiogram data. From that data, there are many kinds of processing that can be done, e.g., to detect various cardiac events, such as tachycardia, fibrillations, heart rate, etc. The obtained electrocardiogram data can be used to titrate medications, or be used for alerts when an important change or significant abnormality in the heart rate or rhythm is detected. This data is also helpful in certain embodiments for monitoring heart rate in patients who do not have pacemakers (e.g., monitoring heart rate in patients with anorexia nervosa) or as an alternative to patients who might normally require a Holter monitor or a Cardiac Event Monitor, portable devices for continuously monitoring the electrical activity of the heart for 24 hours or other devices. An extended recording period is useful for observing occasional cardiac arrthymias that are difficult to identify in shorter time periods.

Another sensing capability that may be accomplished with two electrodes of the signal receiver employs measuring the impedance between the electrodes. The measured impedance will have some component which is determined by the transthoracic impedance, which relates to respiration. In this manner, the impedance data can be employed to obtain the respiratory rate of the subject. The electrodes may also be employed as sensors of the fluid state of subject. Over time, particularly for a heart failure patient on diuretics, fluid status is a very important quantity. The obtained fluid state can be used to titrate medications. The obtained fluid state can also be used for alerts, because right before people go into the hospital, their lungs start filling up with fluid, which could be detected with this system. In addition to measuring fluid status, impedance measurements could also be used to measure body fat. In certain embodiments, electro-dermal response (see e.g., the discussion of such found at the website having an address made up of "http://" placed before "butler-.cc.tut.fi/~malmivuo/bem/bembook/27/27.htm") may be monitored.

As mentioned above, one or more additional physiological sensors distinct from the electrodes may be included in the signal receiver. For example, a temperature sensor, e.g., a thermistor, may be included in the signal receiver. Alternatively, resistive temperature devices (RTDs), e.g., made out of platinum, may be employed to obtain precise measurements of temperature. Another embodiment of interest is an implantable fertility monitor which could come from monitoring a subject's temperature, such as core body temperature, over time, and if desired combining with additional sensed phsyiological parameters. An additional physiological sensor may include an LED and a photodiode combined into a pulse oximeter, which may be employed to measure blood oxygenation, which would also give information about pulse pressure. A magnetic susceptibility sensor can also be employed to measure anemia. See e.g., Published United States Patent Application No. 20010029329.

In addition, embodiments of the signal receivers include a pressure sensor, e.g., where the signal receiver is implanted next to an artery to get measurements of arterial blood pressure. For example, the pressure inside the body is obtained by putting a pressure sensitive membrane on the surface of the signal receiver. For example, a membrane on the side of the signal receiver is brought in proximity to either an artery or a vein, so that as the artery pulses it pushes on the pressure sensor. With appropriate calibration, an absolute pressure reading is obtained. Alternatively, a sensor having outrigger cuff configuration, e.g., in which the sensor cuffed around the vessel (such as an artery) is employed. Strain gauges are presented in certain embodiments to measure pressure deflections, which are then attached to the signal receiver. In another embodiment, strain gauges are used to detect uterine contractions. Such embodiments find use in a variety of different applications, such as the monitoring of high-risk pregnancies.

The signal receivers may also include analyte detection sensors. For example, specific chemical sensors may be incorporated into the signal receivers to detect the presence of various agents, e.g., glucose, BNP (B-type Natriuretic peptide, which is associated with cardiac disease), etc. In certain embodiments, electively porous impedance cells are employed, where the oxygen changes the pH of a cell, and then the conductivity of that change is measured. Where the signal receiver includes an analyte detecting sensing element, this sensing element can be configured in the signal receiver in a number of different ways. For example, a sensor that includes a selectively permeable membrane which is permeable to the agent one wants to detect may be provided, where there is an isolated cell behind it, and the agent passes through the membrane, and changes the properties, usually electrical properties, of the cell, which are then measured. In certain embodiments, a small reservoir on the side of the signal receiver with a membrane across it is employed, and electrical circuitry behind it is measured. Also of interest are ChemFET sensors, which are based on the binding of analyte to the sensor causing a change in the conductivity. In certain embodiments, a material whose electrical properties (or other properties) are changed when the material, e.g., protein analyte, binds to it are employed.

Sensors of interest further include, but are not limited to, those sensors described in the following applications by at least some of the inventors of the present application: U.S. patent application Ser. No. 10/734,490 published as 20040193021 titled: "Method And System For Monitoring And Treating Hemodynamic Parameters"; U.S. patent application Ser. No. 11/219,305 published as 20060058588 titled: "Methods And Apparatus For Tissue Activation And Monitoring"; International Application No. PCT/US2005/046815 titled: "Implantable Addressable Segmented Electrodes"; U.S. patent application Ser. No. 11/324,196 titled "Implantable Accelerometer-Based Cardiac Wall Position Detector"; U.S. patent application Ser. No. 10/764,429, entitled "Method and Apparatus for Enhancing Cardiac Pacing," U.S. patent application Ser. No. 10/764,127, entitled "Methods and Systems for Measuring Cardiac Parameters," U.S. patent application Ser. No. 10/764,125, entitled "Method and System for Remote Hemodynamic Monitoring"; International Application No. PCT/US2005/046815 titled: "Implantable Hermetically Sealed Structures"; U.S. application Ser. No. 11/368,259 titled: "Fiberoptic Tissue Motion Sensor"; International Application No. PCT/US2004/041430 titled: "Implantable Pressure Sensors"; U.S. patent application Ser.

No. 11/249,152 entitled "Implantable Doppler Tomography System," and claiming priority to: U.S. Provisional Patent Application No. 60/617,618; International Application Serial No. PCT/USUS05/39535 titled "Cardiac Motion Characterization by Strain Gauge". These applications are incorporated in their entirety by reference herein.

Of interest in certain embodiments is a signal receiver that may be viewed as an autonomous sensor unit. In certain of these embodiments, the sensor unit includes a sensor and a pair of transmit/receive electrodes that are adapted to be arranged on the skin or body surface of the subject. The receiver may further include a central transmitting and receiving unit which is adapted to be arranged on the body of the subject, and a portable data recording unit. The autonomous sensor units are adapted to acquire sensor data from the body of the subject, i.e., medical and/or physical data such as one or more of pulse rate, blood oxygen content, blood glucose content, other blood composition data, blood pressure data, electrocardiogram data, electroencephalogram data, respiration rate data, perspiration data, body temperature data, activity, motion, electrode impedance, and the like. In addition, the component includes the ability to receive a signal from an internal device, e.g., the identifier of an IEM. The transmit/receive electrodes of each autonomous sensor unit are adapted to transmit the acquired sensor data into the body of the subject, so that these sensor data are transmitted via the skin and/or other body tissues of the subject to a central transmitting and receiving unit. Other signals, such as monitoring signals and polling signals can be transmitted from the central transmitting and receiving unit through the body tissues of the subject to the sensor unit, where these signals are picked up by the transmit/receive electrodes of the respective sensor unit.

The basic system according to the invention, comprising sensor units, a body transceiver, and a data recorder or data logger, allows the data to be recorded in electronic memory cards, or on magnetic data carriers, or the like, or to be downloaded through an appropriate interface into a computer such as a personal computer or an onboard computer system, for carrying out further processing or evaluation. The data transmission from the body transceiver to the data logger or data recorder is carried out by telemetry, for example by a radio link, whereby the transmission range is limited to a few meters, for example less than 10 meters. The portable data logger itself can be worn on a belt or in a pocket of the clothing of the subject, for example.

The sensors integrated into the present inventive system are predominantly sensors for measuring the medical or physical conditions of the subject, for example measuring parameters such as the body temperature, the EKG, the pulse, the blood oxygen saturation, and/or the skin conductivity, of the subject. Nonetheless, additional so-called environmental sensors can also be combined into the inventive system, for example sensors adapted to measure the prevailing ambient air quality such as the oxygen content, the surrounding ambient temperature, and/or the respective location of the sensor by means of a global positioning system (GPS) or the like. Thus, the sensor data transmitted or exchanged via the skin or other body tissues of the subject are not limited to the data relating to the medical or physical condition of the subject, but instead can also provide information regarding the surroundings of the subject. All of these different types of data are received, processed, and retransmitted by the body transceiver. Alternatively, the various data streams of interest may be fused or correlated/processed at a remote location, e.g., a network.

In certain embodiments, the signal receiver (i.e., signal detection component) is an implantable component. By implantable is meant that the signal receiver is designed, i.e., configured, for implantation into a subject, e.g., on a semi-permanent or permanent basis. In these embodiments, the signal receiver is in vivo during use. By implantable is meant that the receivers are configured to maintain functionality when present in a physiological environment, including a high salt, high humidity environment found inside of a body, for 2 or more days, such as about 1 week or longer, about 4 weeks or longer, about 6 months or longer, about 1 year or longer, e.g., about 5 years or longer. In certain embodiments, the implantable circuits are configured to maintain functionality when implanted at a physiological site for a period ranging from about 1 to about 80 years or longer, such as from about 5 to about 70 years or longer, and including for a period ranging from about 10 to about 50 years or longer.

For implantable embodiments, the signal receiver may have any convenient shape, including but not limited to: capsule-shaped, disc-shaped, etc. The signal receiver may be configured to be placed in a number of different locations, e.g., the abdomen, small of the back, shoulder (e.g., where implantable pulse generators are placed) etc.

The implantable receivers of the invention generally include a power source. In certain embodiments, the power source of the receiver is a rechargeable battery. The power source may have a natural life of 2 weeks, and recharge automatically off of coils in the patient's bed so that it would be constantly recharging. In certain embodiments, the signal receiver may be one that is powered during use by RF signal.

In certain implantable embodiments, the signal receiver is a stand alone device, in that it is not physically connected to any other type of implantable device. In yet other embodiments, the implantable signal receiver may be physically coupled to a second implantable device, e.g., a device which serves as a platform for one or more physiological sensors, where the device may be a lead, such as a cardiovascular lead, where in certain of these embodiments the cardiovascular lead includes one or more distinct physiological sensors, e.g., where the lead is a multi-sensor lead (MSL). Implantable devices of interest further include, but are not limited to: implantable pulse generators (e.g., ICDs), neurostimulator devices, implantable loop recorders, etc.

Aspects of the invention include receivers that have at least a receiver element, e.g., in the form of one or more electrodes (such as two spaced apart electrodes) and a power generation element, e.g., a battery, where the battery may be rechargeable, etc., as mentioned above. In certain embodiments the power generation element is converted to receive power wirelessly from an external location.

Additional elements that may be present in the signal receiver include, but are not limited to: a signal demodulator, e.g., for decoding the signal emitted from ingestible event marker; a signal transmitter, e.g., for sending a signal from the signal receiver to an external location; a data storage element, e.g., for storing data regarding a received signal, physiological parameter data, medical record data, etc.; a clock element, e.g., for associated a specific time with an event, such as receipt of a signal; a pre-amplifier; a microprocessor, e.g., for coordinating one or more of the different functionalities of the signal receiver.

Aspects of implantable versions of the signal receiver will have a biologically compatible enclosure, two or more sense electrodes, a power source, which could either be a primary cell or rechargeable battery, or one that is powered by broadcast inductively to a coil. The signal receiver may also have circuitry that includes a demodulator to decode the transmitted signal, some storage to record events, a clock, and a way to transmit outside the body. The clock and transmit functionality may, in certain embodiments, be omitted. The transmitter could be an RF link or conductive link to transfer information from local data storage to an external data storage device.

The demodulator component, when present, may be any convenient demodulator configured to demodulate the signal emitted from the identifier of the pharma-informatics enabled pharmaceutical composition. In certain embodiments, the demodulator is an in-vivo transmission decoder that allows for accurate signal decoding of a low-level signal, even in the presence of significant noise, using a small-scale chip which consumes very low power. In one embodiment, the in-vivo transmission decoder is designed to decode signals which were modulated using binary phase shift keying (BPSK). The signal can then be demodulated using a Costas loop. The binary code is recovered by applying a symbol recovery technique to the Costas loop output. In some embodiments, the in-vivo transmission decoder can include an automatic gain control (AGC) block. The AGC block can determine the strongest frequency component and signal power of the incoming signal. The strongest frequency of the signal can be used to adjust filters and voltage-controlled oscillators in other parts of the algorithm. This can help the receiver to actively adjust to variations of the incoming signal frequency and drift of the incoming signal frequency. By measuring the signal power, the AGC block can then calculate and apply the gain necessary to normalize the signal power to a predetermined value. This gain can further be adjusted by reading the signal power at the Costas loop. In one embodiment, the in-vivo transmission decoder can actively adjust the sampling rate of the incoming signal to adjust to conditions such as the amount of noise present. For example, if the signal to noise ratio (SNR) is sufficient, the sampling rate can be maintained at a low value. If the SNR decreases below a set threshold during the decoding process, the sampling rate can be increased. In this manner, the sampling rate can be kept as low as possible without compromising the accuracy of the recovered signal. By actively adjusting the sampling rate to be as low as possible, the algorithm saves power. Further aspects of such in-vivo transmission decoders are provided in pending U.S. Provisional Application Ser. No. 60/866,581 titled "In-Vivo Transmission Decoder," the disclosure of which application is herein incorporated by reference.

In certain embodiments, the components or functional blocks of the present receivers are present on integrated circuits, where the integrated circuits include a number of distinct functional blocks, i.e., modules. Within a given receiver, at least some of, e.g., two or more, up to an including all of, the functional blocks may be present in a single integrated circuit in the receiver. By single integrated circuit is meant a single circuit structure that includes all of the different functional blocks. As such, the integrated circuit is a monolithic integrated circuit (also known as IC, microcircuit, microchip, silicon chip, computer chip or chip) that is a miniaturized electronic circuit (which may include semiconductor devices, as well as passive components) that has been manufactured in the surface of a thin substrate of semiconductor material. The integrated circuits of certain embodiments of the present invention may be hybrid integrated circuits, which are miniaturized electronic circuits constructed of individual semiconductor devices, as well as passive components, bonded to a substrate or circuit board.

Figure 13:
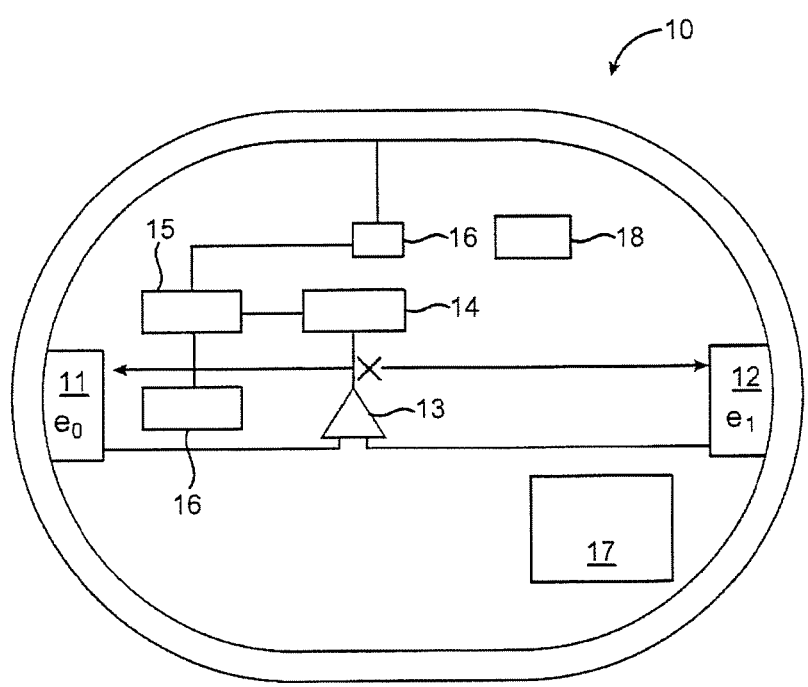
FIG. 13 shows diagrammatically a signal receiver according to an embodiment of the invention.

FIG. 13 provides a schematic representation of a functional block diagram according to an embodiment of the invention. In FIG. 13, receiver 10 includes first and second electrodes, $e_0$ and $e_1$ (11 & 12 respectively), which are separated by distance X and serve as an antenna to receive a signal generated by an identifier of a pharma-informatics enabled pharmaceutical composition. The distance X may vary, and in certain embodiments ranges from about 0.5 to about 5 cm, such as from about 0.5 to about 1.5 cm, e.g., about 1 cm. Amplifier 13 detects the differential signal across the electrodes. The detected signal then goes into the demodulator 14. Also shown is memory 15 to store the demodulated data. Clock 16 which writes to that memory which time-stamps the events. Transmit circuit (Tx) (16) transfers data from the memory out to the external receiver (not shown). There is also a power source 17 which powers all the microelectronics. In the embodiment depicted, also present is a microprocessor 18, which coordinates the function between all these blocks. Finally, a coil 19 wound around the perimeter provides for RF transmission out. As summarized above, all of the different functional blocks shown in the embodiment of FIG. 13 could be on the same integrated circuit.

Figure 14:
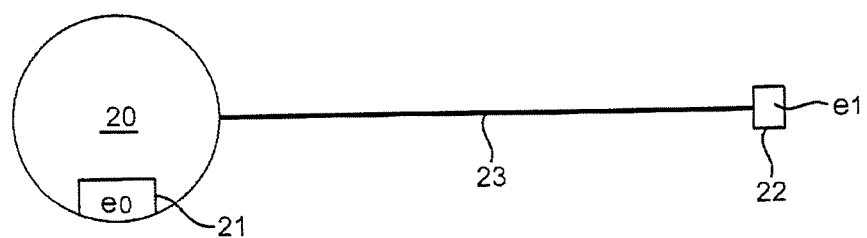
FIG. 14 shows diagrammatically a signal receiver according to a second embodiment of the invention.

An alternative embodiment is depicted in FIG. 14. In FIG. 14, the main portion of the receiver 20 includes all of the functionalities listed above (not shown) and $e_0$ (21). Also shown is $e_1$ which is at the end of wire 23. This configuration provides for sufficient distance between $e_0$ and $e_1$ to serve as an effective receiver and yet minimizes the overall size of the receiver 20.

Figure 15:
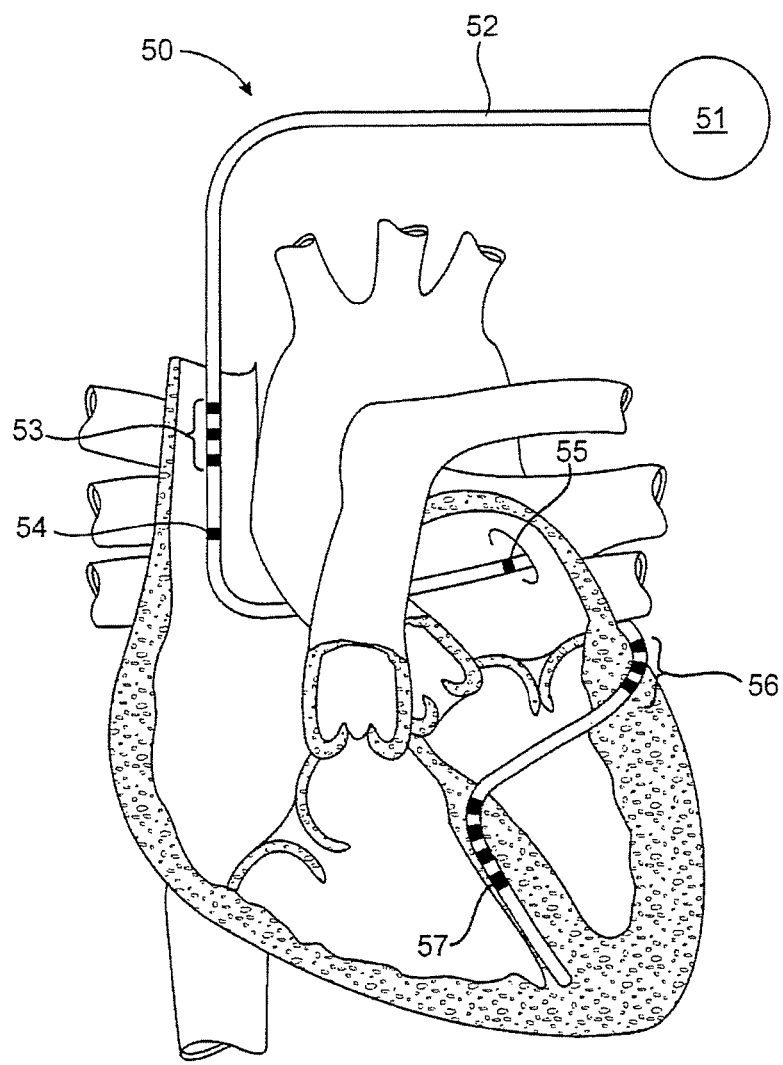
FIG. 15 shows diagrammatically a signal receiver having a multi-sensor lead (MSL) according to another embodiment of the invention.

As reviewed above, in certain embodiments the signal receiver is physically coupled to a medical carrier, e.g., a lead, which has on it one or more distinct physiological sensors. In such embodiments, the lead may have one or more, e.g., two or more, three or more, four or more, 5 or more, about 10 or more, about 15 or more, etc., distinct physiological sensors, where the sensors may be any sensor of interest, including those referred to above. FIG. 15 provides a representation of a signal receiver that is configured specifically for use in monitoring and treating cardiac condition. In FIG. 15, receiver 50 includes main receiver component 51 and cardiovascular lead 52, where lead 52 includes a number of different sensors and therefore may be referred to as a multi-sensor lead or MSL. Also shown on lead 52 are conductive blood flow sensors 53, temperature sensor 54 positioned to measure the temperature of blood entering the heart, temperature sensor 55 positioned to measure the coronary sinus temperature, sense electrodes 56, positioned to measure movement of relevant cardiac tissue and stimulating electrodes 57. The sense and stimulating electrodes may be ring electrodes or segmented electrodes. By segmented electrode structure is meant an electrode structure that includes two or more, e.g., three or more, including four or more, disparate electrode elements. Embodiments of segmented electrode structures are disclosed in Application Serial Nos.: PCT/US2005/031559 titled "Methods and Apparatus for Tissue Activation and Monitoring," filed on Sep. 1, 2006; and PCT/US2005/46811 titled "Implantable Addressable Segmented Electrodes" filed on Dec. 22, 2005; the disclosures of the various segmented electrode structures of these applications being herein incorporated by reference. One or more such electrode assemblies may be placed along a cardiac pacing lead.

In the embodiment shown in FIG. 15, the MSL goes from the receiver down into the heart, and can be employed to measure cardiac parameters of interest, e.g., blood temperature, heart rate, blood pressure, movement data, including synchrony data, IEGM data, as well as pharmaceutical therapy compliance. The obtained data is stored in the receiver. Embodiments of this configuration may be employed as an early heart failure diagnostic tool. This configuration may be put into a subject before they got very sick from heart failure, with the goal of monitoring them closely and keep them from getting sicker. Ultimately, when stimulation therapy is required, the receiver may be replaced with an implantable pulse generator, which may then employ the stimulating electrodes to provide appropriate pacing therapy to the patient.

Figure 16:
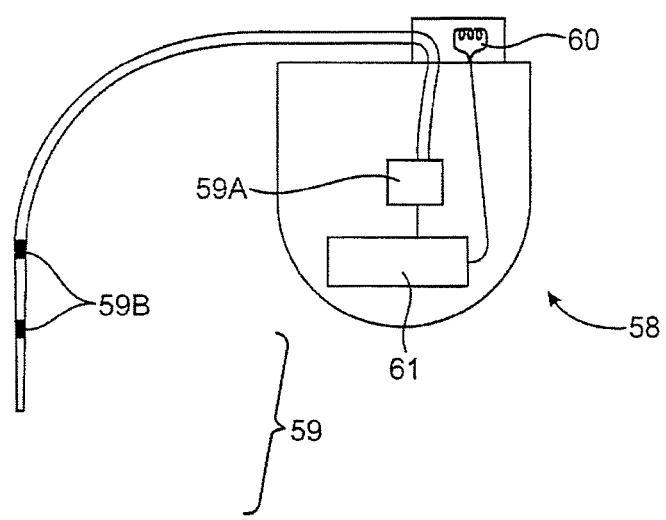
FIG. 16 provides a view of an implantable pulse generator that includes a receiver component according to an embodiment of the invention.
Figure 17A:
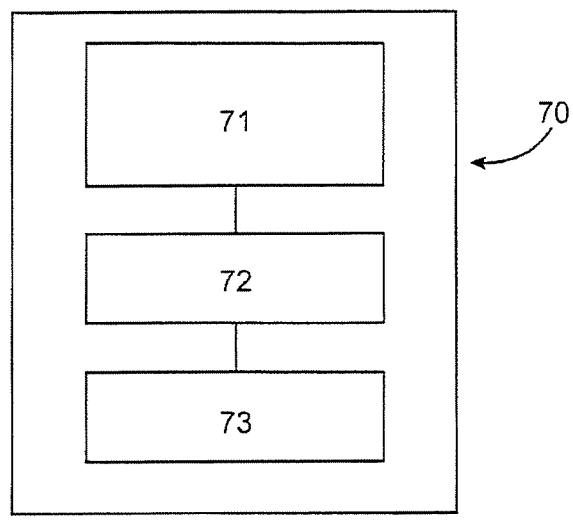
FIGS. 17A and 17B provide additional information about various aspects of embodiments of external receivers according to embodiments of the invention.
Figure 17B:
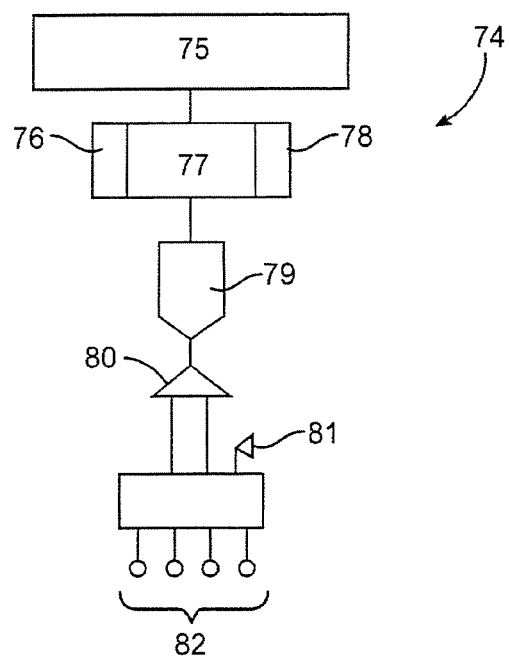

The signal receiver can be a component of an implantable device that includes other functionality. For example, the signal receiver can be a component of an implantable pulse generator 58, such as a pacemaker, etc. FIG. 16 provides a view of an implantable pulse generator 58 that includes a receiver component 59 according to an embodiment of the invention, where the receiver component includes receive circuitry 59A and receive electrodes 59B. Also shown is external interface antenna 60 and pacing electronics 61.

Where the signal receivers are external, they may be configured in any convenient manner. External configuration may include any of the elements described above with respect to implantable embodiments, as desired. As such, external receivers may include circuits as depicted in FIG. 13, and described above. Accordingly, elements as described above, such as signal receivers, transmitters, memory, processors, demodulators, etc., may be present in external receivers of the invention, as desired. For example, functional diagrams of circuitry that may be present in external receivers of the invention are provides in FIGS. 17A and 17B. FIG. 17A provides a functional block diagram of a receiver 70 according to the invention, where the receiver includes an external interface block 71, where the external interface block may include a wireless communication element (e.g., antenna), serial port, conductive interface, etc. Also presence is signal receive circuitry block 72. Also present is receive electrodes functional block 73. FIG. 17B provides a view of a circuit 74 found in a receiver according to an embodiment of the invention. Circuit 74 includes external interface 75, memory 76, digital signal processor (DSP) 77 and real time clock (RTC) 78. Also shown is analog to digital converter (ADC) 79, pre-amplifier 80, optional reference (common mode cancellation circuit) 81 and electrodes 82.

In certain embodiments, the signal receivers are configured to be associated with a desirable skin location. As such, in certain embodiments the external signal receivers are configured to be contacted with a topical skin location of a subject. Configurations of interest include, but are not limited to: patches, wrist bands, belts, harnesses, devices configured to associates with articles of clothing, e.g., shoes, necklaces, etc., or other body associated devices, e.g., hearing aids, eye glasses, and the like. For instance, a watch or belt worn externally and equipped with suitable receiving element, e.g., electrode or pair of electrodes as described in greater detail below, can be used as a signal receiver in accordance with one embodiment of the present invention.

Figure 18:
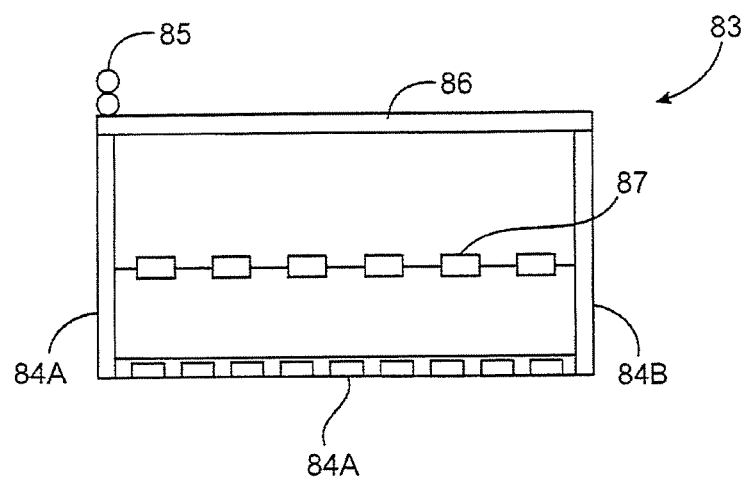
FIG. 18 provides a view of receiver/pill dispenser device according to an embodiment of the invention.

In certain external embodiments, the receiver may be configured to be in contact with or associated with a patient only temporarily, i.e., transiently, for example while the ingestible event marker is actually being ingested. For example, the receiver may be configured as an external device having two finger electrodes or handgrips. Upon ingestion of the IEM, the patient touches the electrodes or grabs the handgrips completely to produce a conductive circuit with the receiver. Upon emission of the signal from the IEM, e.g., when the IEM contacts the stomach, the signal emitted by the identifier of the IEM is picked up by the receiver. At this point, the receiver may provide an indication to the patient, e.g., in the form of an audible or visual signal, that the signal from the IEM has been received. As indicated above, in certain external embodiments, the receiver is configured to be in contact with or associated with a patient only temporarily, i.e., transiently, for example while the pill, ingestible marker, etc., is actually being ingested. For example, the receiver may be configured as an external device, such as the medication dispenser box 83 shown in FIG. 18. Dispense box 83 includes two finger electrodes 84A and 84B. In certain embodiments these electrodes are in the form of handgrips or other convenient patient contact format. During use, the patient initially activates the device and receiver by opening the lid 86. To alert the patient that it is time to take medication, the box may be configured to provide a signal or alarm. Upon removal of a dosage from the box (where the dosage is present in a compartment 87, a first signal may be provided, e.g., a red light, for example at indicator light 85. The patient then ingests the pill which includes the IEM, and touches a right finger to the right finger electrode 84B and a left finger to the left finger electrode 84A to complete a conductive circuit with the receiver. Upon emission of the signal from the IEM which is associated with the pill, e.g., when the pill dissolves in the stomach, the signal emitted by the identifier of the pill is picked up by the receiver. At this point, the receiver may provide an indication to the patient, e.g., the form of an audible or visual signal (such as a green light) that the signal from the pill has been received. The patient can then release the receiver until the next time that the patient is scheduled to take pill. The box 83 includes detection circuitry, memory and transmit functionality 88, e.g., as described above. Such embodiments have applications in a wide variety of different settings, e.g., for Tuberculosis patients on long term therapeutic regimens.

Figure 19:
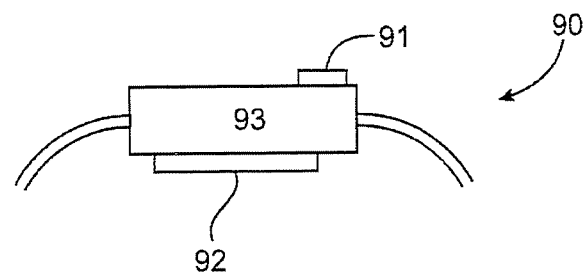
FIG. 19 provides a view of a wrist band receiver embodiment of the invention.

FIG. 19 provides a view of a wrist band receiver embodiment of the invention. As shown, the receiver is in the form of a wrist band 90 which includes a top 91 and bottom 92 contact, where the bottom contact is for contacting the wrist of the patient. The top contact is for the patient to touch with a right finger during use. During use of this device, upon ingestion of an IEM, the patient then touches the right finger to the contact 91 on the receiver 93 which is also in contact with the left wrist via contact 92, thereby completing the circuit. Upon detection of the IEM generated signal, the patient can remove the finger from the receiver.

Such a system is useful in monitoring patient compliance with a therapeutic regimen, e.g., where ingestion of the IEM is associated with administration of therapeutic active agent (as described in greater detail below). The patient can then release the receiver until the next time that the patient is scheduled to take the active agent. Such embodiments have applications in a wide variety of different settings, e.g., for tuberculosis patients on long term therapeutic regimens, where embodiments of such systems are further described in greater detail below.

In certain embodiments, the external signal receiver includes miniaturized electronics which are integrated with the electrodes to form a band-aid style patch. The patch includes electrodes that when applied, contact the skin. The bandaid style patch may be configured to be positioned on a desirable target skin site of the subject, e.g., on the chest, back, side of the torso, etc. In these embodiments, the receiver circuitry may be configured to receive signals from devices inside of the subject, e.g., from an identifier IEM. Bandaid style receivers that may be readily adapted for use in the present systems include, but are not limited to: those described in U.S. Pat. No. 6,315,719 and the like, the disclosures of which are herein incorporated by reference.

For the external signal receivers, embodiments include structures that have electrodes opposed to the skin, the demodulator, storage, and power. The communication may be wireless or performed over one or more conductive media, e.g., wires, optical fibers, etc. In certain embodiments, the same electrodes are used for receiving and transmitting signals. One example is a wristwatch format which is conductively in contact with the body, where to move the data from the implant to the wristwatch one would send currents out the pads and those would be received by the wristwatch. There are a number of RF techniques for getting the transmission out of the body that may be employed, such as inductive protocols that employ coils. Alternatively, one could employ electric fields, where one would use insulated electrodes, not conductively contacted electrodes.

Where the signal receiver includes an external component, that component may have output devices for providing, e.g., audio and/or visual feedback; examples include audible alarms, LEDs, display screens, or the like. The external component may also include an interface port via which the component can be connected to a computer for reading out data stored therein.

The signal receivers reviewed above are described primarily in terms of being configured to receive a signal from an ingestible event marker (IEM). However, the signal receivers of the invention may be ones configured to receive a signal from a pharma-informatics enabled pharmaceutical composition (e.g., as described in PCT application Serial No. US2006/016370); an ingestible event marker (e.g., as described in provisional application Ser. No. 60/949,223); or a smart parenteral device (e.g., as described in PCT/US2007/15547); the disclosures of which are herein incorporated by reference, or analogous device.

System Operation

In the methods of the IEM systems of the invention, when an individual wants to mark or note a personal event of interest, the individual ingests one or more ingestible event marker of the invention. The marker may be ingested by the subject using any convenient means capable of producing the desired result, where the administration route depends, at least in part, on the particular format of the composition, e.g., as reviewed above, and involves ingesting the ingestible event marker, e.g., by swallowing the IEM composition. A variety of different types of individuals may practice the methods. Generally such individuals are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In representative embodiments, the subjects will be humans.

Depending on the particular application, the methods may include ingesting an event marker by itself or in conjunction with another composition of matter, where in the later embodiment the identifier may be co-ingested with the other composition of matter or combined with the other composition of matter and then ingested. If co-ingested, the identifier and the other composition of matter may be ingested sequentially or at the same time. A given method may include ingestion of a signal identifier or two or more identifiers (which may be the same or different) depending on the given application. In certain embodiments, multiple identifiers may be employed to mark an event, e.g., to indicate degree of whatever the event is. One could take different markers to indicate different types of events.

Once the ingestible event marker reaches the target physiological site, the identifier of the IEM emits a detectable signal, e.g., as reviewed above. A signal receiver may handle received data (e.g., in the form of a signal emitted from an ingestible event marker) in various ways. In some embodiments, the signal receiver simply retransmits the data to an external device (e.g., using conventional RF communication), e.g., immediately or following some period of time, in which case the data is stored in a storage element of the receiver. Accordingly, in certain embodiments, the signal receiver stores the received data for subsequent retransmission to an external device or for use in processing of subsequent data (e.g., detecting a change in some parameter over time). For instance, an implanted collector may include conventional RF circuitry (operating, e.g., in the 405 MHz medical device band) with which a practitioner can communicate, e.g., using a data retrieval device, such as a wand as is known in the art. In other embodiments, the signal receiver processes the received data to determine whether to take some action such as operating an effector that is under its control, activating a visible or audible alarm, transmitting a control signal to an effector located elsewhere in the body, or the like. The signal receivers may perform any combination of these and/or other operations using received data.

In certain embodiments, the data that is recorded on a data storage element of the receiver includes at least one of, if not all of, time, date, and an identifier (e.g., global unique serial no.) of each composition administered to a patient, where the identifier may be the common name of the composition or a coded version thereof. The data recorded on the data storage element of the receiver may further include medical record information of the subject with which the receiver is associated, e.g., identifying information, such as but not limited to: name, age, treatment record, etc. In certain embodiments, the data of interest includes hemodynamic measurements. In certain embodiments, the data of interest includes cardiac tissue properties. In certain embodiments, the data of interest includes pressure or volume measurements, temperature, activity, respiration rate, pH, etc.

In certain embodiments, the signal receivers are part of a body associated system or network of sensors, receivers, and optionally other devices, both internal and external, which provide a variety of different types of information that is ultimately collected and processed by a processor, such as an external processor, which then can provide contextual data about a patient as output. For example that sensor may be a member of an in-body network of devices which can provide an output that includes data about pill ingestion, one or more physiological sensed parameters, implantable device operation, etc., to an external collector of the data. The external collector, e.g., in the form of a health care network server, etc., of the data then combines this receiver provided data with additional relevant data about the patient, e.g., weight, weather, medical record data, etc., and may process this disparate data to provide highly specific and contextual patient specific data.

In certain embodiments, the signal receiver is configured to provide data of a received signal to a location external to said subject. For example, the signal receiver may be configured to provide data to an external data receiver, e.g., which may be in the form of a monitor (such as a bedside monitor), a computer (e.g., PC or MAC), a personal digital assistant (PDA), phone, messaging device, smart phone, etc. In one embodiment, if a signal receiver failed to detect a signal indicating that a pill had been ingested, the signal receiver could transmit a reminder to take the pill to the subject's PDA or smart phone, which could then provide a prompt to the user to take the medication, e.g., a display or alarm on the PDA, by receiving a phone call on the smart phone (e.g., a recorded message) etc. The signal receiver may be configured to retransmit data of a received signal to the location external to said subject. Alternatively, the signal receiver according may be configured to be interrogated by an external interrogation device to provide data of a received signal to an external location.

As such, in certain embodiments the systems include an external device which is distinct from the receiver (which may be implanted or topically applied in certain embodiments), where this external device provides a number of functionalities. Such an apparatus can include the capacity to provide feedback and appropriate clinical regulation to the patient. Such a device can take any of a number of forms. By example, the device can be configured to sit on the bed next to the patient, e.g., a bedside monitor. Other formats include, but are not limited to, PDAs, smart phones, home computers, etc. The device can read out the information described in more detail in other sections of the subject patent application, both from pharmaceutical ingestion reporting and from physiological sensing devices, such as is produced internally by a pacemaker device or a dedicated implant for detection of the pill. The purpose of the external apparatus is to get the data out of the patient and into an external device. One feature of the external apparatus is its ability to provide pharmacologic and physiologic information in a form that can be transmitted through a transmission medium, such as a telephone line, to a remote location such as a clinician or to a central monitoring agency.

Figure 20:
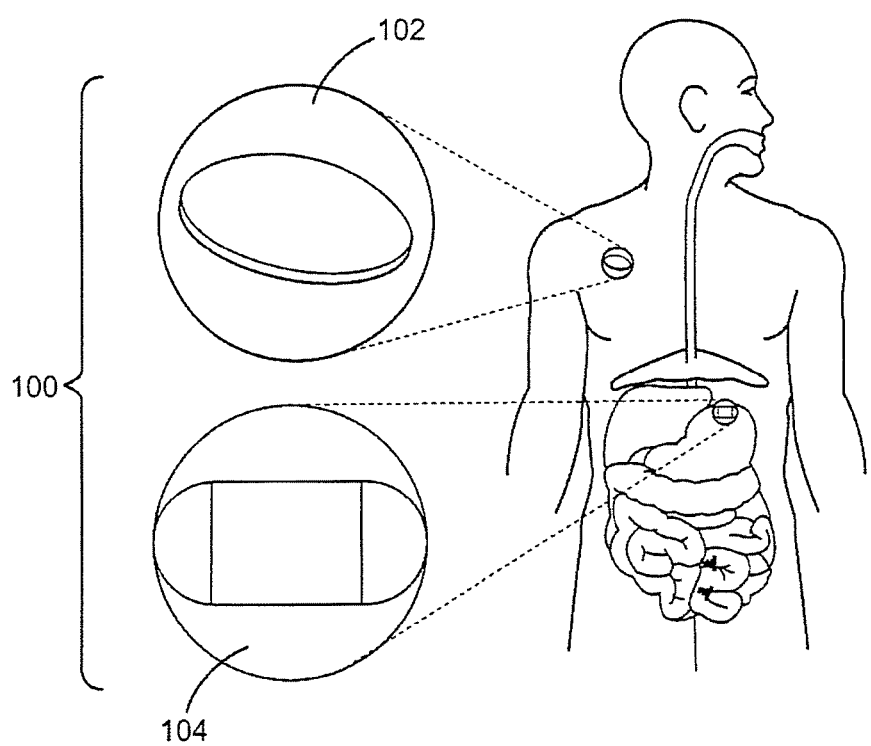
FIG. 20 shows a depiction of a system according to an embodiment of the invention.

FIG. 20 provides a schematic view of a system according to an embodiment of the invention. In FIG. 20, system 100 includes ingestible event marker 104 and personal health receiver 102. In the system shown in FIG. 20, the IEM 104 is a pill that has been outfitted with an identifier in the form of an embedded, digestible microchip-based data transmitter. The data transmitter is activated for a short period of time when ingested and sends a unique signal to a data receiver 102. In the case of multi-drug therapy, each pill ingested by a patient would have a different electronic signal for detection, e.g. provided by a different IEM either taken as part of the pharmaceutical dosage or in conjunction with the pharmaceutical dosage. The microchip is composed of silicon-based materials that pass easily through the digestive tract and other compounds with a long history of use as vitamins.

Also shown in the system of FIG. 20 is the receiver 102, which is a dime-sized, wearable (e.g., as a patch) or subcutaneous implantable receiver that contains a detector to record the ingestion of IEM and physiologic sensors to monitor respiration, heart rate, temperature, blood pressure and/or other key biomarkers. In certain embodiments, the receiver is part of an existing medical implants, such as pump devices, implantable cardiac defibrillators, neurological devices, etc (see e.g., FIG. 16). In certain embodiments, receiver 102 stores other important and related healthcare data, such as a patient's medical record.

Not shown in FIG. 20 is an external recorder. However, as summarized above, the system may include one or more external elements. Software can be installed on a hand-held PDA, such as a Blackberry, or on a laptop or desktop computer, enabling secured wireless data transmission from a receiver and user-controlled information distribution to physicians and caregivers. These systems allow data gathered on the actual time and level of medication dosing by patients to be integrated with physiologic parameters and presented to patients and physicians in ways that support better individual performance and caregiver clinical decisions and disease management.

Figure 21:
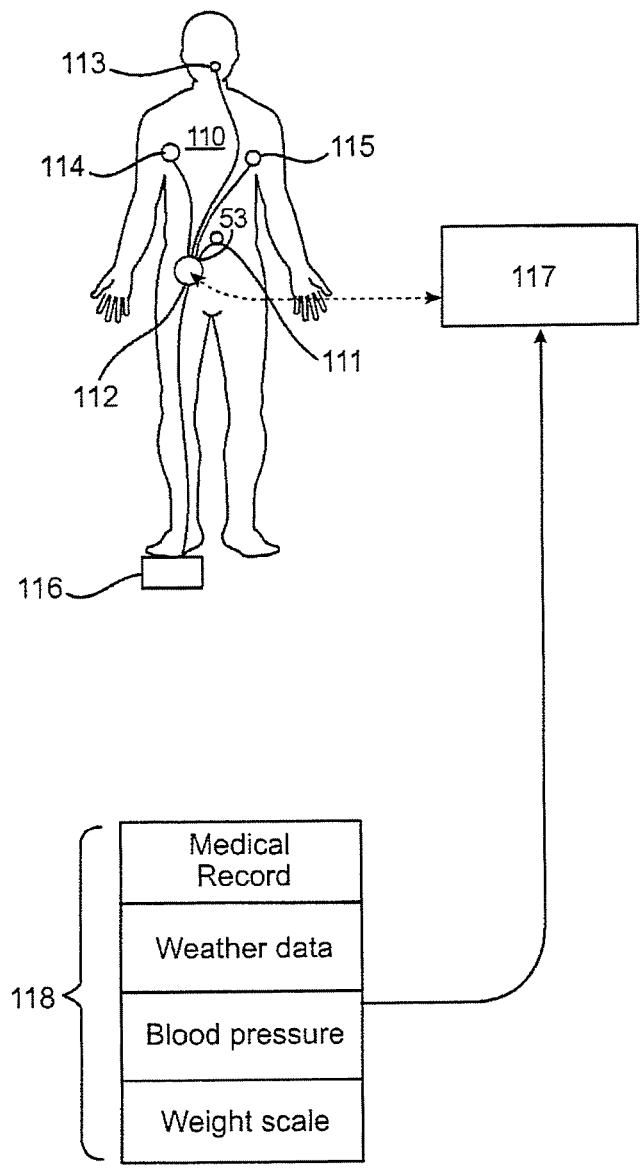
FIG. 21 provides a view of an "in-body" network that includes a receiver according to an embodiment of the invention.

FIG. 21 shows an embodiment of a system of the invention that includes an IEM and receiver, as well as additional physiological parameter sensors and data sources of non-physiological parameters. In FIG. 21, patient 110 ingests an IEM 111 with a pharmaceutically active agent. The IEM 111 emits a signal upon contact with stomach fluid which is received by receiver 112. Receiver 112 also obtains data from neuro stimulator 113, pressure sensor 114, $O_2$ sensor 115 and pedometer 116 in the shoe of the patient. These various data streams are sent by receiver to external server. External server 117 processes these IEM annotated data streams with additional information 118, such as medical records of the patient, weather data, blood pressure data and weight data, to obtain contextualized data. The following table shows different sensors types that may be employed in systems of the invention, and the types of data obtained therefrom. The data obtained from such disparate components of systems of these embodiments may be fused at a network layer, as desired, for subsequent use, e.g., by a health care professional.

| Receiver Sensors | | | | Implanted Sensors | | Networked Sensors | | |
|---|---|---|---|---|---|---|---|---|
| Skin Electrodes EKG Heart Rate Electrodermal Response | Electrode Impedance Respiration Fluid Status | Temperature Sensor Body Temperature Energy flux | Accelerometer Activity estimation Body motion Tremor characterization | Pressure Sensor Blood Pressure Cardiac performance Aneurysm Detection dP/dt | Multi-Sensor Lead Synchrony Contactility Ejection Fraction LV Volume Cardiac Motion | Ambulatory Blood Pressure Hypertension | Glucose Monitor Diabetes | Bathroom Scale Fluid Status Weight Gain |

As reviewed above, in certain embodiments of interest, the receiver element includes a semiconductor support component. Any of a variety of different protocols may be employed in manufacturing the receiver structures and components thereof. For example, molding, deposition and material removal, e.g., planar processing techniques, such as Micro-Electro-Mechanical Systems (MEMS) fabrication techniques, including surface micromachining and bulk micromachining techniques, may be employed. Deposition techniques that may be employed in certain embodiments of fabricating the structures include, but are not limited to: electroplating, cathodic arc deposition, plasma spray, sputtering, e-beam evaporation, physical vapor deposition, chemical vapor deposition, plasma enhanced chemical vapor deposition, etc. Material removal techniques included, but are not limited to: reactive ion etching, anisotropic chemical etching, isotropic chemical etching, planarization, e.g., via chemical mechanical polishing, laser ablation, electronic discharge machining (EDM), etc. Also of interest are lithographic protocols. Of interest in certain embodiments is the use of planar processing protocols, in which structures are built up and/or removed from a surface or surfaces of an initially planar substrate using a variety of different material removal and deposition protocols applied to the substrate in a sequential manner. Illustrative fabrication methods of interest are described in greater detail in copending PCT application serial no. PCT/US2006/016370; the disclosure of which is herein incorporated by reference.

In certain embodiments, off-the-shelf components may be employed to fabricate the receivers. For example, an off-the-shelf instrumentation amplifier for the input amp may be employed, e.g., in bare die form. Custom logic, either in an FPGA or in an ASIC, that handles the demodulator, the memory, the microprocessor functions, and all the interface functions may be used. The transmitter may be an off-the-shelf chip, e.g., made by Zarlink, in the mixed communication band, which is approved for medical implants. The clock may be a stand-alone clock, or the device may have a microprocessor that has a clock built in.

Utility

The subject ingestible event markers, systems and methods of use may be employed in a variety of different applications, which applications may be both medical and non-medical in nature. Different illustrative applications are now reviewed below in greater detail below.

As mentioned above, certain applications involve the use of the ingestible identifiers by themselves to mark a personal event of interest, e.g., onset of a physiological parameter (such as a symptom(s) of interest), onset of an activity, etc. For example, in certain embodiments event markers are employed to mark the onset of a symptom of interest. In such instances, when an individual becomes aware of a symptom of interest, e.g., begins to feel flushed, nauseous, excited, etc., e.g., the individual may ingest an IEM to mark the occurrence of the symptom of interest. For example, the patient may begin to not feel well, and ingest an event marker in response to this ill feeling. Upon ingestion, the marker sends a signal to a receiver, which may then record receipt of the signal for further use, e.g., to combine with physiological data, etc. In certain embodiments, the received signal is employed to provide context for any physiological data that is obtained from the patient, e.g., by sensors on the receiver, from an implantable recorder, etc.

Another symptom of interest is pain. In these embodiments, the ingestible event marker may be employed a pain marker. For example, where a patient is being monitored for pain, if a patient feels no pain, the patient may ingest a first type of marker. If the patient feels pain, the patient may ingest a second type of marker. Different types of markers may be differentiated, such as color coded, where desired, to assist in their identification and proper use by the patient. For example, markers to be ingested when the patient does not feel pain may be color coded blue, while markers that are to be ingested with the patient does have pain may be color coded yellow. Instead of having different types of markers, a protocol may be employed in which the amount of markers ingested, and therefore the signal obtained, e.g., from a single marker or two or more markers, is employed to denote scale of symptom of interest, such as pain. So, if an individual is having intense pain, the individual takes four of the positive pain pills at the same time, while in response to mild pain the individual may take only one marker.

In such embodiments, the onset of the symptom of interest, as marked by the ingestion of the event marker and detection of the signal by the receiver, may be employed as relevant point at which to begin recording one or more physiological parameters of interest, e.g., by using an implantable physiological monitor. In these instances, the emitted signal from the marker is received by the receiver, which then causes a physiological parameter recorder (such as a Reveal® Plus Insertable Loop Recorder (ILR), Medtronic Corporation) to begin recording data and saving the data, e.g., for later use.

For example, an implantable physiological parameter recorder may have only a limited possible amount of time for recording (such as 42 minutes). In such situations, the data may be automatically overwritten unless somehow flagged or marked for protection. In the present methods, an IEM may be ingested to mark the onset of a symptom of interest, as perceived by the patient, and receiver upon receipt of the signal may act with the recorder to protect the data obtained around the time of the signal (after, or even some time before) to be protected and not overwritten. The system may be further configured to work in response not only to the ingestion of the event marker, but also in response to physiological sensed parameters, e.g., pH. As such, the methods find use as an event recorder in terms of flagging a diagnostic stream of information, and protecting it from being overwritten, so a physician can look at it at a later date.

In certain embodiments, the event marker provides the context for interpreting a given set of physiological data at a later time. For example, if one is employing an activity sensor and one co-administers and event marker with a particular drug, one can note any change in activity that is brought about by that drug. If a drop in activity is observed after a person takes both the event marker and a drug, the drop indicates the drug is probably causing the person to reduce their activity, e.g., by making them feel sleepy or actually causing them to fall asleep. Such data may be employed to adjust the does of a drug or be the basis for a decision to switch to an alternative medication.

In certain embodiments the event marker is employed to construct a database of multiple events. Such a database may be employed to find commonality between the multiple marked events. Simple or complex protocols for finding commonality among multiple marked events may be employed. For example, multiple events may be averaged. Alternatively techniques such as impulse response theory may be employed, where such techniques provide information on what exactly are the common features in a set of multiple sensor streams that are tied to a particular event.

The IEM systems of the invention enable one to use subjective symptoms, such as "I'm feeling funny," to impart context and background to obtained objective measures of what's really going on physiologically. So, if every time somebody felt abnormal they took an event marker, one could reference a database of the objective sensor data, and find common features in the database. Such an approach may be employed to discover the underlying causes of the subjective feeling. For example, such an approach may be employed to determine that every time a person is feeling funny, they have some change in their blood pressure, and that link between a subjective symptom and objective physiological data can be used in their diagnosis. As such, a generalizable event marker brings context to discrete data from any other source. As such, use of the oral medication event markers provides context for any other associated health monitoring information or health event.

In certain embodiments, the event marker can be an alert marker, such that ingestion of the marker causes an alarm signal to be sent from the patient, e.g., indicating that the patient needs medical assistance. For example, when a patient feels an onset of a symptom of interest, such as chest pain, shortness of breath, etc., the patient may ingest an event marker. The signal emitted from the event marker may be received by the receiver, which may then cause an alarm to be generated and distributed to a medical professional.

In certain embodiments, the event marker is employed to instigate or start a therapeutic action, e.g., activate an implantable pulse generator to deliver electrical therapy, activate an implanted drug delivery device to administer a dosage of drug, activate a physiological sensor to begin acquiring data, etc. For example, where a patient has a neural stimulator for treating migraines, upon perception of the onset of aura, the patient could ingest an IEM. The emitted signal would then activate neural stimulator into stimulus mode, and thereby cause the implant to deliver therapy. Alternatively, if one has an implanted drug deliver device, e.g., a device that delivers an oncotic agent, ingestion of the IEM could cause the implanted device to deliver the active agent.

In certain embodiments, the event marker is employed to deliver information to an implanted medical device in the patient. For example, an ingestible event marker may send a signal that includes update data for an implanted medical devices, such as firmware upgrade data for an implantable pulse generator, e.g., a pace maker. In such instances, the signal may include the upgrade code which is broadcast from the IEM conductively to the medical device, where upon receipt of the signal and code, the firmware of the medical device is upgraded.

Other applications where event markers may be employed by themselves is to mark or note the start of non-medical personal event, such as a commute time, the start of an exercise regimen, sleep time, smoking (e.g., so one can log how much one smokes) etc.

As indicated above, embodiments of the invention are characterized in that the event markers are co-ingested with another composition of matter, e.g., a pharmaceutical composition, food, etc. For example, the event markers may be employed to track ingesting a pharmaceutical agent, where one co-administers the marker with the drug of interest. Applications where co-administration of a drug and marker is of interest include, but are not limited to, clinical studies, titration of medicine, e.g., blood pressure medicine, etc. Where desired, the IEM could be provided as just another pill when the fill at the pharmacy essentially.

Instead of co-ingesting the event marker with another composition, e.g., a drug, food, etc., the marker and the other composition may be compounded together, e.g., by the end user. For example, an IEM in the form of a capsule can be opened by the end user and filled with a pharmaceutical composition. The resultant compounded capsule and active agent may then be ingested by the end user. Instead of an end user, the pharmacist or a health care provided may perform the compounding step.

In yet other embodiments, the marker is present already compounded with the other composition at the source of manufacture of the other composition, e.g., the manufacturer or producer of a pharmaceutical composition. An example of such compositions includes those described in PCT application serial no. PCT/US2006/016370; the disclosure of which is herein incorporated by reference.

In certain embodiments, the IEMs of the invention are employed to allow one to look at, on an individual basis, what a given result is with respect to what drugs an individual is taking versus their impact on indicators that correlate to the desired effect. For example, where a given patient is prescribed a regiment of multiple pharmaceutical agents and there are multiple different phsyiological parameters that are monitored as indicators of how the patient is responding to the prescribed therapeutic regimen, a given drug as marked by a given marker can be assessed in terms of its impact on a one or more of the physiological parameters of interest. Following this assessment, adjustments can be made accordingly. In this manner, automation may be employed to tailor therapies based on individual responses. For example, where a patient is undergoing oncotic therapy, the event marker can be used to provide real time context to obtained physiological parameter data. The resultant annotated real time data can be used to make decisions about whether or not to continue therapy, or change to a new therapy.

Figure 22:
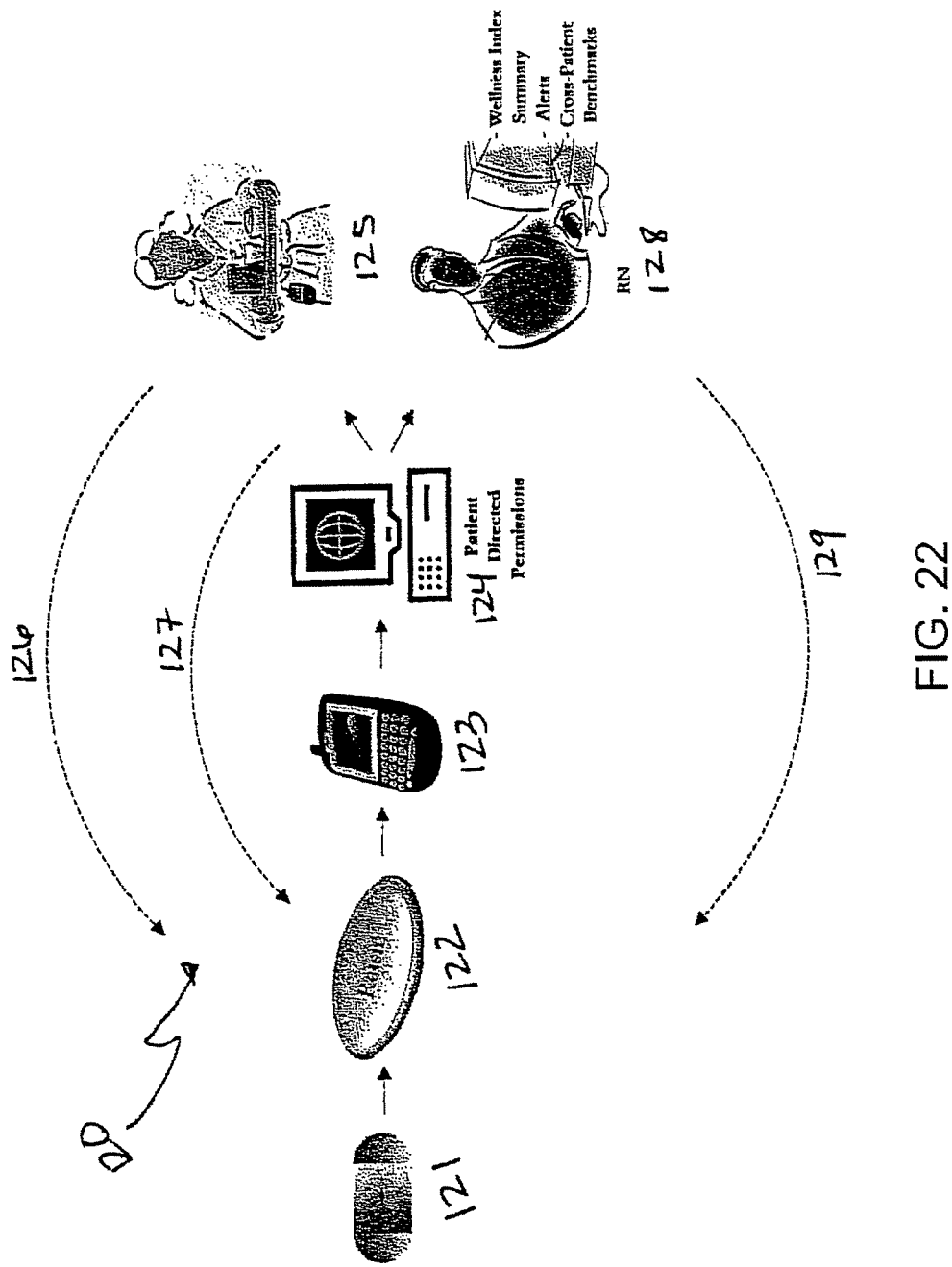
FIG. 22 shows how the system of the invention interacts with external elements and is employed according to an embodiment of the invention.

In certain embodiments, a dosing event (as marked by the IEM) is correlated with sensor data to develop a profile for how a given drug acts, e.g., in terms of a pharmacokinetic and/or pharmacodynamic model. Sensors are employed with the IEM marking of the dosing event to obtain a pharmacokinetic model. Once one has the pharmacokinetic model, one can use the dosing event to drive that model and predict serum drug levels and response. One might find, as determined from various sensors, that this patient is not doing so well at this time. One might look back at the pharmacokinetic model and say the levels of this drug in the blood are getting low when the patient is sensed as not doing well. This data is then used to make a determination to increase the dosing frequency or increase the dose at a given dosing event. The event marker provides a way to develop a model and then apply it.

Where the IEMs are co-administered with a pharmaceutical agent, e.g., as two separate compositions or a single composition (as described above), the systems of the invention, such as the one shown in FIG. 12, enable a dynamic feedback and treatment loop of tracking medication timing and levels, measuring the response to therapy, and recommending altered dosing based on the physiology and molecular profiles of individual patients. For example, a symptomatic heart failure patient takes multiple drugs daily, primarily with the goal of reducing the heart's workload and improving patient quality of life. Mainstays of therapy include angiotensin converting enzyme (ACE) inhibitors, β-blockers and diuretics. For pharmaceutical therapy to be effective, it is vital that patients adhere to their prescribed regimen, taking the required dose at the appropriate time. Multiple studies in the clinical literature demonstrate that more than 50% of Class II and III heart failure patients are not receiving guideline-recommended therapy, and, of those who are titrated appropriately, only 40-60% adhere to the regimen. With the subject systems, heart failure patients can be monitored for patient adherence to therapy, and adherence performance can be linked to key physiologic measurements, to facilitate the optimization of therapy by physicians. In FIG. 22, system 120 includes a pharmaceutical composition 121 that comprises an IEM. Also present in system 120 is receiver 122 (labeled "Raisin" in the figure), which is configured to detect signal emitted from the identifier of the pharmaceutical composition 121. Implanted receiver 122 also includes physiologic sensing capability. Implanted receiver 122 is configured to transmit data to an external PDA 123, which in turn transmits the data to a server 124. Server 124 may be configured as desired, e.g., to provide for patient directed permissions. For example, server may be configured to allow a family caregiver to participate in the patient's therapeutic regimen, e.g., via an interface (such as a web interface) that allows the family caregiver to monitor alerts and trends generated by the server, and provide support back to the patient, as indicated by arrow 126. The server may also be configured to provide responses directly to the patient, e.g., in the form of patient alerts, patient incentives, etc., as indicated by arrow 127. Server 124 may also interact with a health care professional (e.g., RN, physician) 128, which can use data processing algorithms to obtain, e.g., wellness index summaries, alerts, cross-patient benchmarks, etc., and provide informed clinical communication and support back to the patient, as indicated by arrow 129.

In certain embodiments, the systems of the invention may be employed to obtain an aggregate of information that includes sensor data and administration data. For example, one can combine the heart rate, the respiration rate, multi-axis acceleration data, something about the fluid status, and something about temperature, and derive indices that will inform about the total activity of the subject, that can be used to generate a physiological index, such as an activity index. For instance, when there is a rise in temperature, heart rate goes up a bit, and respiration speeds up, which may be employed as an indication that the person is being active. By calibrating this, the amount of calories the person is burning at that instant could be determined. In another example, a particular rhythmic set of pulses or multi-axis acceleration data can indicate that a person is walking up a set of stairs, and from that one can infer how much energy they are using. In another embodiment, body fat measurement (e.g. from impedance data) could be combined with an activity index generated from a combination of measured biomarkers to generate a physiological index useful for management of a weight loss or cardiovascular health program. This information can be combined with cardiac performance indicators to get a good picture of overall health, which can be combined with pharmaceutical therapy administration data. In another embodiment, one might find for example that a particular pharmaceutical correlates with a small increase in body temperature, or a change in the electrocardiogram. One can develop a pharmacodynamic model for the metabolism of the drug, and use the information from the receiver to essentially fit the free parameters in that model to give much more accurate estimation of the levels actually present in the serum of the subject. This information could be fed back to dosing regimes. In another embodiment, one can combine information from a sensor that measures uterine contractions (e.g. with a strain gauge) and that also monitors fetal heart rate, for use as a high-risk pregnancy monitor.

In certain embodiments, the subject specific information that is collected using the systems of the invention may be transmitted to a location where it is combined with data from one or more additional individuals to provide a collection of data which is a composite of data collected from 2 or more, e.g., 5 or more, 10 or more, 25 or more, 50 or more, 100 or more, 1000 or more, etc., individuals. The composite data can then be manipulated, e.g., categorized according to different criteria, and made available to one or more different types of groups, e.g., patient groups, health care practitioner groups, etc., where the manipulation of data may be such as to limit the access of any given group to the type of data that group can access. For example, data can be collected from 100 different individuals that are suffering from the same condition and taking the same medication. The data can be processed and employed to develop easy to follow displays regarding patient compliance with a pharmaceutical dosage regimen and general health. Patient members of the group can access this information and see how their compliance matches with other patient members of the group, and whether they are enjoying the benefits that others are experiencing. In yet another embodiment, doctors can also be granted access to a manipulation of the composite data to see how their patients are matching up with patients of other doctors, and obtain useful information on how real patients respond to a given therapeutic treatment regiment. Additional functionalities can be provided to the groups given access to the composite data, where such functionalities may include, but are not limited to: ability to annotate data, chat functionalities, security privileges, etc.

The inventive pharmacokinetic model allows for drug dosing regimens to be adjusted in real time in response to varying serum levels in the body. The pharmacokinetic model can predict or measure the serum level of a given medication in the body. This data can then be used to calculate when the next dose of medication should be taken by the patient. An alarm can be triggered at that time to alert the patient to take a dose. If the serum level remains high, an alarm can be triggered to alert the patient not to take the next dose at the originally prescribed time interval. The pharmacokinetic model can be used in conjunction with a medication ingestion monitoring system that includes an IEM, such as that described above. Data from this system can be incorporated into the model, as well as population data, measured data, and data input by the patient. Utilizing data from multiple sources, a very powerful and accurate tool can be developed.

In some embodiments, the data gathered by the receiver can be used directly by the pharmacokinetic model to determine when a medication was administered, what medication it was and in what amount. This information can be used to calculate an estimate of the serum level of the medication in the patient. Based on the calculated serum level, the pharmacokinetic model can send an alert to the patient to say either that the serum level is too high and is near or above the toxic level, or that the serum level is too low and they should take another dose. The pharmacokinetic model can be run on the implanted receiver itself or on an external system which receives data from the implanted receiver.

A simple form of the pharmacokinetic model can assume that every patient is the same, and use average population data to model the serum level. A more complex and more accurate model can be obtained by inputting other information about the patient. This information can be inputted by the user, such as a physician, or gathered by the receiver from associated sensors. Information that can be used to adjust the model include other medications being taken, diseases the patient suffers from, patient's organ function, enzyme levels, metabolism, body weight, and age, among other factors. Information can also be inputted by the patient themselves, such as if they feel hypoglycemic, or have pain or dizziness. This can be used as further evidence to validate the predictions of the model.

Serum levels can also be estimated based on physiological parameters, such as body temperature and heart rate. For example, if a patient is taking a beta blocker, that affects heart rate, and there could be feedback built into the model. If the heart rate is going up, and there is no other physiological reason for it, such as increased activity, then the model can assume that it is going up because the beta blocker is wearing off.

In other embodiments, the actual serum level can be measured directly by the implanted receiver and used in the model. Many serum level sensors have a limited number of wells which can be used for measurements. In this case, several measurements can be taken in the early stages to develop the initial model parameters. After that, the serum level can be measured periodically and compared to the model estimation. The serum level can be measured at regular intervals, or in specific circumstances, such as a time of high uncertainty, or a time in relation to another event such as the ingestion of a pill. The model can be adjusted using optimal estimation techniques in order for the model to adjust to the data. Model fitting techniques are well known in the art. In one embodiment, techniques such as those discussed in "Optimal Control and Estimation," by Robert F. Stengel (Dover Publications, 1994), herein incorporated by reference in its entirety, can be used to fit the model to the measured data.

By gathering some initial data from the individual patient, the pharmacokinetic model can be adjusted to fit the individual. During a hospital visit, patients often receive routine labs that gather a wide range of data. During this time, serum levels can be measured. In cases where the patient is outfitted with a system which records the consumption of medications, the system will know when the medications were taken, and can use that information in conjunction with the measured serum levels to fit the model. Alternatively, the information on time, type, and amount of medication administered can be input by a health care administrator. In situations where the patient would not otherwise receive lab tests, the physician can decide whether lab tests should be performed specifically for the purpose of gathering data to fit the pharmacokinetic model to.

When a medication is first introduced to a patient, it will not be at steady state, and the reaction measured in the body is not necessarily indicative of how the body will react after adjusting to the medication. This can be accounted for in the model. Also, later measurements from the implant unit can help to adjust the model to the steady state.

Once the model is fitted to the individual patient, it can be run on the implant device in the patient. The implant device can communicate wirelessly with external devices to relay model data as well as measured data, such as the patient's actual medication dosing schedule. The implant can also send alerts to an external device to send a message to the patient, such as to take another dose of medication. In some cases, such as if the patient has taken too much medication, the pharmacokinetic model can send an alert to the patient to tell them to visit the doctor. Also, the pharmacokinetic model can contact the doctor or a hospital directly if it detects a medical problem.

In other embodiments, data gathered from a subset of the population which includes the patient can be used to give an initial model. For instance, a model can be developed which more closely resembles the drug interactions in a patient that suffers from kidney failure by looking at population data. This model can then be used as a starting point for any patient that has kidney failure, then adjusted for any other data which is input.

Other medications being taken can greatly affect the way the individual drugs are processed in the body. When incorporated with the pharma-informatics system, the receiver will know when multiple medications are being taken, and can adjust the model accordingly.

The dynamic dosing regimen made possible by the pharmacokinetic model can be a very valuable tool in prescribing medication to patients. In the case of insulin, insulin levels in the body are dependant on metabolism and the formulation of the insulin, among other factors. The pharmacokinetic model can take these factors into account when determining the serum level of insulin. Also, blood sugar can be measured directly and incorporated into the model. Using this information, the pharmacokinetic model can alert the patient when it determines that another shot of insulin should be administered.

The pharmacokinetic model can also incorporate the sleeping habits of the patient when determining the suggested timing of doses. Since the patient will not be able to administer a dose of medication while sleeping, the pharmacokinetic model can keep track of the usual hours that the patient is asleep, and use this information to determine when doses should be taken to keep the serum level in the optimum range.

In some cases, where it is possible to take varying amounts of a medication in a particular dose, that can be incorporated into the model. For example, a patient can be told to take either one or two pills depending on current serum level and other factors.

Figure 23:
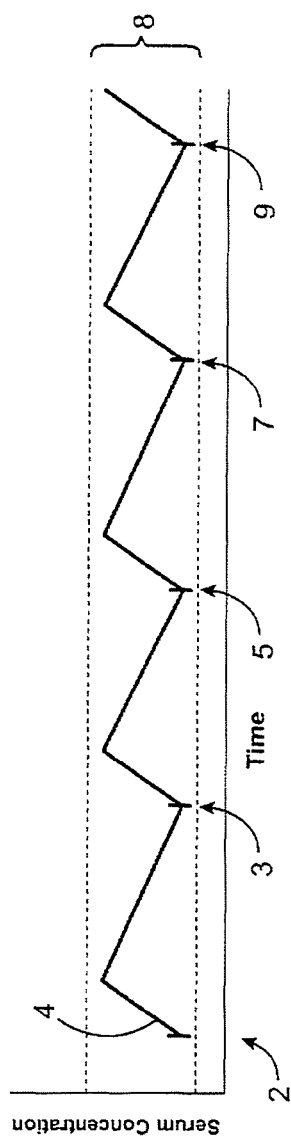
FIG. 23 shows a graph of medication serum level over time which depicts the ideal situation where the patient takes a dose of medication at regular time intervals.

FIG. 23 shows the ideal situation, where a medication dose is taken at time 2, and serum level 4 rises and then decays. Another dose is taken at time 3, 5, 7, and 9. Serum level 4 stays within therapeutic range 8 throughout. The times that doses are taken are evenly spaced, and the decay always occurs at the same rate. This graph depicts the ideal situation on which prescribed dosing regimens are based.

Figure 24:
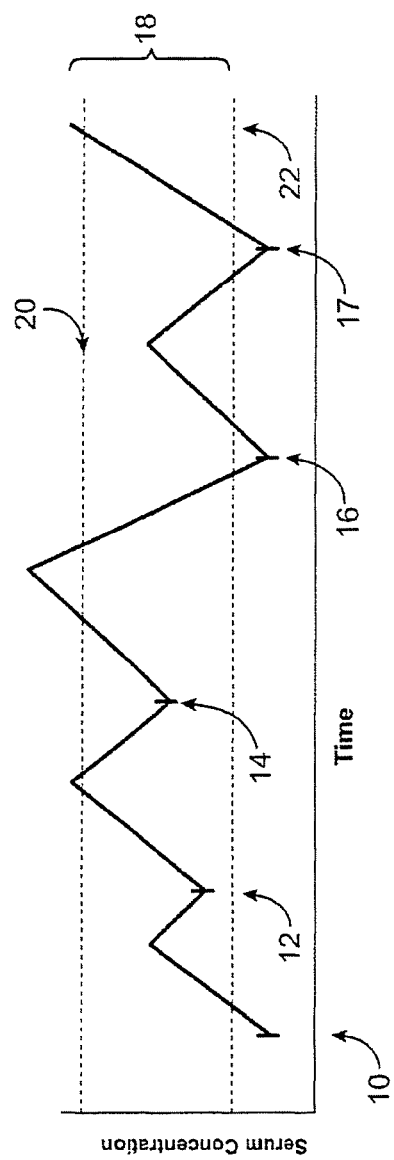
FIG. 24 shows a graph of medication serum level over time which depicts the situation where the patient takes doses of medication at uneven time intervals.

FIG. 24 shows a hypothetical graph which depicts a more real world situation, where doses of medication are taken at uneven intervals. Doses are taken at times 10, 12, 14, 16, and 17. Therapeutic range 18 is bound by toxic limit 20 and lower limit 22. The serum concentration in this graph rises above toxic limit 20 and also drops below lower limit 22 due to the uneven dosing times. The situation in FIG. 24 would be avoided using the pharmacokinetic model. At point 14, the system can send an alert to the patient to tell them not to take a dose at that time. The system can tell the patient the next time they should take a dose. In the case of an implant, the alerts can be sent wirelessly to an external unit which can display the message to the patient, such as a personal data assistant (PDA), computer, watch, cell phone, or other device. The time the next dose should be taken may change as new measurements are obtained, and the displayed message can be changed accordingly. The system will not assume that the patient complies with the message displayed to them. When the pharmacokinetic model is used in conjunction with a system which detects the ingestion of medications, the system will record when a medication is taken. Alternatively, when the estimated or measured serum level rises, the system can make the determination that a dose was taken. The system can be configured to continue to remind the patient to take a dose until it determines that a dose was taken. Alternatively, the patient can input data to the system that they have taken a dose.

The pharmacokinetic model can be used in conjunction with a more robust model, such as that discussed in U.S. provisional application "ET Constrained Heart Model," Ser. No. 60/893,545, filed Mar. 7, 2007, hereby incorporated by reference in its entirety. When enough data is incorporated into the model, the model can become predictive of the individual patient. This allows the physician to experiment with different treatment options on the model instead of on the patient themselves. For example, the physician can study the effect different medication regimens would have on the patient, and depending on the results, choose the optimal treatment. All of the data which is gathered by the implant receiver, as well as data from health records, and data input by the medical staff and the patient themselves can be incorporated directly into the model.

In an embodiment of the pharmacokinetic model, several free parameters can be adjusted until the results of the model agree with the measured results in the patient. When the results of the model agree with measured results in the patient, one can then draw the conclusion that the model is predictive for that particular patient, and base therapy upon those predictions.

Newly gathered or inputted data can be checked against the model, and the model can be fitted to the new data in order to keep up with changes in the patient, and to make the model more accurate. If the data coming in varies greatly from what the model predicts, this may be a sign that something else is going on in the patient, and an alarm can be sent alerting of the discrepancy. This can be very powerful in identifying changes in the patient before they develop more visible symptoms.

Figure 25:
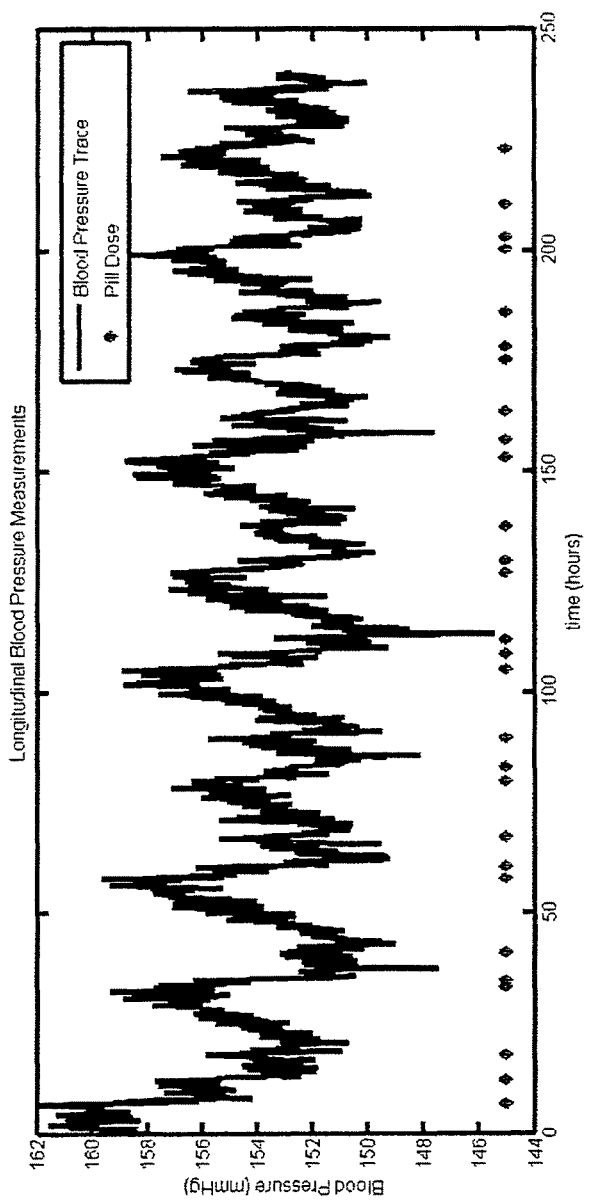
FIGS. 25 to 27 provide views of various aspects of different embodiments of the invention.
Figure 26:
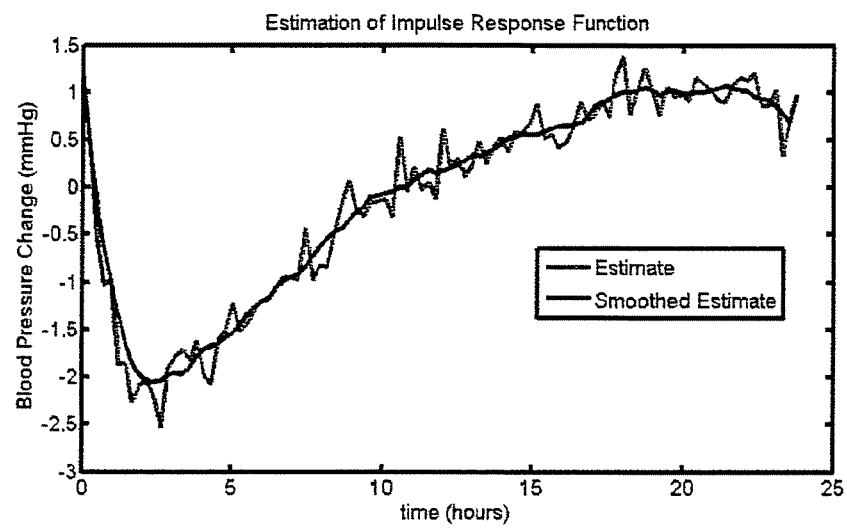
Figure 27:
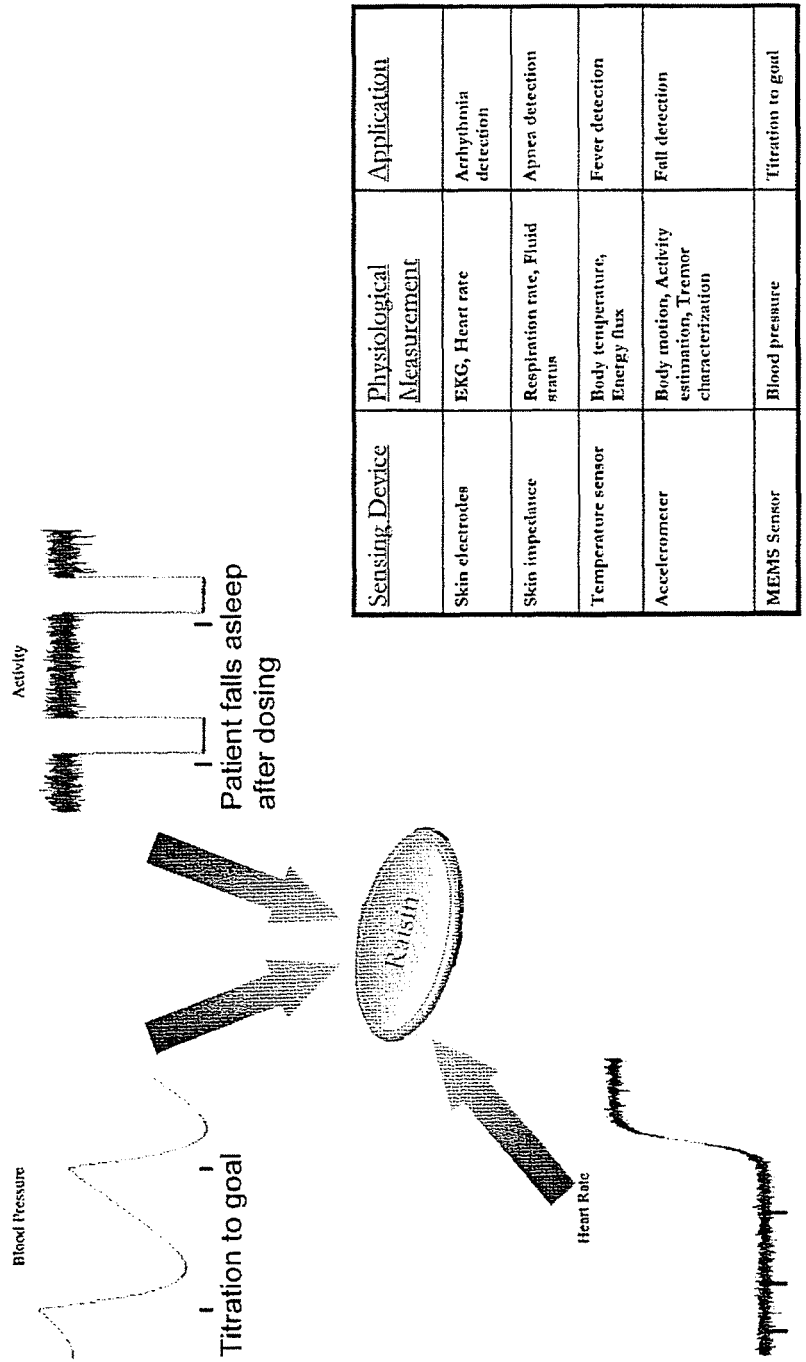

FIG. 25 provides a depiction of use of an embodiment of the system to provide an estimation of dose response from longitudinal blood pressure measurements. In FIG. 26 it is apparent that given a longitudinal blood pressure trace with knowledge of pill ingestion times (e.g., provided by an IEM system of the invention), the individual dose response can be determined using a general linear model of the pharmacokinetics. An example of a general linear model of dose response that may be employed is shown in FIG. 26. FIG. 27 provides a depiction of different physiologic sensing nodalities that may find use in systems of invention (The element denoted "Raisin" is a personal health receiver in accordance with the invention).

Examples of food applications include the following. In certain disease conditions, such as diabetes, it can be important what a patient ate and when. In such instances, event markers of the invention are keyed or linked to the type of food a patient eats. For example, one can have a set of event markers for different food items, and one can co-administer them with the food items. From the resultant data, one can do a complete individual metabolic profile on an individual. One knows how many calories the patient is consuming. By obtaining activity and heart rate and ambient temperature versus body temperature data, one can calculate how many calories one is expending. As a result, guidance can be provided to the patient as to what foods to eat and when. Non disease patients may also track food ingestion in this manner. For example, athletes adhering to a strict training diet may employ IEMs to better monitor food ingestion and the effect of the food ingestion on one or more physiological parameters of interest.

As reviewed in the above discussion, IEM systems of invention find use in both therapeutic and non-therapeutic applications. In therapeutic applications, the IEM may or may not be compounded with a pharmaceutically active agent. In those embodiments where the IEM is compounded with active agent, the resultant compounded composition may be viewed as a pharma-informatics enabled pharmaceutical composition.

In such pharma-informatics embodiments, an effective amount of a composition that includes an IEM and an active agent is administered to a subject in need of the active agent present in the composition, where "effective amount" means a dosage sufficient to produce the desired result, e.g. an improvement in a disease condition or the symptoms associated therewith, the accomplishment of a desired physiological change, etc. The amount that is administered may also be viewed as a therapeutically effective amount. A "therapeutically effective amount" means the amount that, when administered to a subject for treating a disease, is sufficient to effect treatment for that disease.

The composition may be administered to the subject using any convenient means capable of producing the desired result, where the administration route depends, at least in part, on the particular format of the composition, e.g., as reviewed above. As reviewed above, the compositions can be formatted into a variety of formulations for therapeutic administration, including but not limited to solid, semi solid or liquid, such as tablets, capsules, powders, granules, ointments, solutions, suppositories and injections. As such, administration of the compositions can be achieved in various ways, including, but not limited to: oral, buccal, rectal, parenteral, intraperitoneal, intradermal, transdermal, intracheal, etc., administration. In pharmaceutical dosage forms, a given composition may be administered alone or in combination with other pharmaceutically active compounds, e.g., which may also be compositions having signal generation elements stably associated therewith.

The subject methods find use in the treatment of a variety of different conditions, including disease conditions. The specific disease conditions treatable by with the subject compositions are as varied as the types of active agents that can be present in the subject compositions. Thus, disease conditions include, but are not limited to: cardiovascular diseases, cellular proliferative diseases, such as neoplastic diseases, autoimmune diseases, hormonal abnormality diseases, infectious diseases, pain management, and the like.

By treatment is meant at least an amelioration of the symptoms associated with the disease condition afflicting the subject, where amelioration is used in a broad sense to refer to at least a reduction in the magnitude of a parameter, e.g. symptom, associated with the pathological condition being treated. As such, treatment also includes situations where the pathological condition, or at least symptoms associated therewith, are completely inhibited, e.g. prevented from happening, or stopped, e.g. terminated, such that the subject no longer suffers from the pathological condition, or at least the symptoms that characterize the pathological condition. Accordingly, "treating" or "treatment" of a disease includes preventing the disease from occurring in an animal that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease). For the purposes of this invention, a "disease" includes pain.

In certain embodiments, the subject methods, as described above, are methods of managing a disease condition, e.g., over an extended period of time, such as 1 week or longer, 1 month or longer, 6 months or longer, 1 year or longer, 2 years or longer, 5 years or longer, etc. The subject methods may be employed in conjunction with one or more additional disease management protocols, e.g., electrostimulation based protocols in cardiovascular disease management, such as pacing protocols, cardiac resynchronization protocols, etc; lifestyle, such a diet and/or exercise regimens for a variety of different disease conditions; etc.

In certain embodiments, the methods include modulating a therapeutic regimen based data obtained from the compositions. For example, data may be obtained which includes information about patient compliance with a prescribed therapeutic regimen. This data, with or without additional physiological data, e.g., obtained using one or more sensors, such as the sensor devices described above, may be employed, e.g., with appropriate decision tools as desired, to make determinations of whether a given treatment regimen should be maintained or modified in some way, e.g., by modification of a medication regimen and/or implant activity regimen. As such, methods of invention include methods in which a therapeutic regimen is modified based on signals obtained from the composition(s).

In certain embodiments, also provided are methods of determining the history of a composition of the invention, where the composition includes an active agent, an identifier element and a pharmaceutically acceptable carrier. In certain embodiments where the identifier emits a signal in response to an interrogation, the identifier is interrogate, e.g., by a wand or other suitable interrogation device, to obtain a signal. The obtained signal is then employed to determine historical information about the composition, e.g., source, chain of custody, etc.

In certain embodiments, a system is employed that is made up of a multiple different IEMs, e.g., 2 or more distinct IEMS, 3 or more distinct IEMS, 4 or more distinct IEMs, etc., including 5 or more, 7 or more, 10 or more distinct IEMs. The distinct IEMs may be configured to provide distinguishable signals, e.g., where the signals may be distinguishable in terms of nature of the signal itself, in terms of timing of emission of the signal, etc. For example, each IEM in such sets may emit a differently coded signal. Alternatively, each IEM may be configured to emit the signal at a different physiological target site, e.g., where each IEM is configured to be activated at a different target physiological site, e.g., where an first IEM is activated in the mouth, a second is activated in the esophagus, a third is activated in the small intestine and a fourth is activated in the large intestine. Such sets of multiple different distinguishable IEMs find use in a variety of different applications. For example, where one has the above described 4 IEM set, one can use the set in a diagnostic application to determine function of the digestive system, e.g., motility through the digestive tract, gastric emptying etc. For example, by noting when each IEM emits its respective signal, a plot of signal time may be generated from which information regarding digestive tract functioning may be obtained.

The present invention provides the clinician an important new tool in their therapeutic armamentarium: automatic detection and identification of pharmaceutical agents actually delivered into the body. The applications of this new information device and system are multi-fold. Applications include, but are not limited to: (1) monitoring patient compliance with prescribed therapeutic regimens; (2) tailoring therapeutic regimens based on patient compliance; (3) monitoring patient compliance in clinical trials; (4) monitoring usage of controlled substances; and the like. Each of these different illustrative applications is reviewed in greater detail below in copending PCT Application Serial No. PCT/US2006/016370; the disclosure of which is herein incorporated by reference.

Additional applications in which the subject systems find use include those described in U.S. Pat. No. 6,804,558, the disclosure of which is herein incorporated by reference. For example, the subject systems may be used in a medical information communication system which permits monitoring the performance of an implantable medical device (IMD) implanted within a body of a patient, monitoring the health of the patient, and/or remotely delivering a therapy to the patient through the IMD. A signal receiver of the invention, e.g., in an external format such as a bandaid or implanted format, communicates with the IMD and is capable of bi-directional communication with a communication module, a mobile telephone and/or a Personal Data Assistant (PDA) located outside the patient's body. The system may comprise the IMD, the signal receiver with the communication module and/or a mobile telephone and/or a PDA, a remote computer system, and a communication system capable of bi-directional communication, where the communication module, the mobile telephone and/or the PDA are capable of receiving information from the IMD or relaying information thereto via the signal receiver, which is internal or external to the patient, as reviewed above.

Additional applications in which receivers of the invention may find use include, but are not limited to: fertility monitoring, body fat monitoring, satiety monitoring, satiety control, total blood volume monitoring, cholesterol monitoring, smoking detecting, etc.

Computer Readable Media & Programming

In certain embodiments, the system further includes an element for storing data, i.e., a data storage element, where this element is present on an external device, such as a bedside monitor, PDA, smart phone, etc. Typically, the data storage element is a computer readable medium. The term "computer readable medium" as used herein refers to any storage or transmission medium that participates in providing instructions and/or data to a computer for execution and/or processing. Examples of storage media include floppy disks, magnetic tape, CD-ROM, a hard disk drive, a ROM or integrated circuit, a magneto-optical disk, or a computer readable card such as a PCMCIA card and the like, whether or not such devices are internal or external to the computer. A file containing information may be "stored" on computer readable medium, where "storing" means recording information such that it is accessible and retrievable at a later date by a computer. With respect to computer readable media, "permanent memory" refers to memory that is permanent. Permanent memory is not erased by termination of the electrical supply to a computer or processor. Computer hard-drive ROM (i.e. ROM not used as virtual memory), CD-ROM, floppy disk and DVD are all examples of permanent memory. Random Access Memory (RAM) is an example of non-permanent memory. A file in permanent memory may be editable and re-writable.

The invention also provides computer executable instructions (i.e., programming) for performing the above methods, e.g., for programming the IEM, receiver, and other components of the system. The computer executable instructions are present on a computer readable medium. Accordingly, the invention provides a computer readable medium containing programming for use in detecting and processing a signal generated by a composition of the invention, e.g., as reviewed above.

As such, in certain embodiments the systems include one or more of: a data storage element, a data processing element, a data display element, data transmission element, a notification mechanism, and a user interface. These additional elements may be incorporated into the receiver and/or present on an external device, e.g., a device configured for processing data and making decisions, forwarding data to a remote location which provides such activities, etc.

The above described systems are reviewed in terms of communication between an identifier on a pharmaceutical composition and a receiver. However, the systems are not so limited. In a broader sense, the systems are composed of two or more different modules that communicate with each other, e.g., using the transmitter/receiver functionalities as reviewed above, e.g., using the monopole transmitter (e.g., antenna) structures as described above. As such, the above identifier elements may be incorporated into any of a plurality of different devices, e.g., to provide a communications system between two self-powered devices in the body, where the self-powered devices may be sensors, data receivers and storage elements, effectors, etc. In an exemplary system, one of these devices may be a sensor and the other may be a communication hub for communication to the outside world. This inventive embodiment may take a number of forms. There can be many sensors, many senders and one receiver. They can be transceivers so both of these can take turns sending and receiving according to known communication protocols. In certain embodiments, the means of communication between the two or more individual devices is the mono polar system, e.g., as described above. In these embodiments, each of these senders may be configured to take turns sending a high frequency signal into the body using a monopole pulling charge into and out of the body which is a large capacitor and a conductor. The receiver, a monopole receiver is detecting at that frequency the charge going into and out of the body and decoding an encrypted signal such as an amplitude modulated signal or frequency modulated signal. This embodiment of the present invention has broad uses. For example, multiple sensors can be placed and implanted on various parts of the body that measure position or acceleration. Without having wires connecting to a central hub, they can communicate that information through a communication medium.

Kits

Also provided are kits for practicing the subject methods. Kits may include components of the IEM systems of the invention, e.g., one or more IEMs (including sets of distinguishable IEMs), one or more receivers, a third external device, etc., as described above. In addition, the kits may include one or more dosage compositions, e.g., pharma-informatics enabled dosage compositions or compositions to be co-administered with an IEM. The dosage amount of the one or more pharmacological agents provided in a kit may be sufficient for a single application or for multiple applications. Accordingly, in certain embodiments of the subject kits a single dosage amount of a pharmacological agent is present and in certain other embodiments multiple dosage amounts of a pharmacological agent may be present in a kit. In those embodiments having multiple dosage amounts of pharmacological agent, such may be packaged in a single container, e.g., a single tube, bottle, vial, and the like, or one or more dosage amounts may be individually packaged such that certain kits may have more than one container of a pharmacological agent.

Suitable means for delivering one or more pharmacological agents to a subject may also be provided in a subject kit. The particular delivery means provided in a kit is dictated by the particular pharmacological agent employed, as describe above, e.g., the particular form of the agent such as whether the pharmacological agent is formulated into preparations in solid, semi solid, liquid or gaseous forms, such as tablets, capsules, powders, granules, ointments, solutions, suppositories, injections, inhalants and aerosols, and the like, and the particular mode of administration of the agent, e.g., whether oral, buccal, rectal, parenteral, intraperitoneal, intradermal, transdermal, intracheal, etc. Accordingly, certain systems may include a suppository applicator, syringe, I.V. bag and tubing, electrode, etc.

In certain embodiments, the kits may also include an external monitor device, e.g., as described above, which may provide for communication with a remote location, e.g., a doctor's office, a central facility etc., which obtains and processes data obtained about the usage of the composition.

In certain embodiments, the kits may include a smart parenteral delivery system that provides specific identification and detection of parenteral beneficial agents or beneficial agents taken into the body through other methods, for example, through the use of a syringe, inhaler, or other device that administers medicine, such as described in copending application serial no. PCT/US2007/015547 filed Jul. 6, 2007 and titled "Smart Parenteral Administration System"; the disclosure of which is herein incorporated by reference.

The subject kits may also include instructions for how to practice the subject methods using the components of the kit. The instructions may be recorded on a suitable recording medium or substrate. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Some or all components of the subject kits may be packaged in suitable packaging to maintain sterility. In many embodiments of the subject kits, the components of the kit are packaged in a kit containment element to make a single, easily handled unit, where the kit containment element, e.g., box or analogous structure, may or may not be an airtight container, e.g., to further preserve the sterility of some or all of the components of the kit.

It is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A system comprising:
    an ingestible event marker (IEM) composition configured to emit a signal upon contact with a target physiological site and does not include an active agent;
    wherein the IEM comprises:
        a first battery structure comprising:
            a first cathode;
            a first anode, wherein the first cathode and the first anode are made at least in part from dissimilar materials selected to provide a voltage potential difference when the first cathode and the first anode contact an electrolyte made up at least in part by fluid present at the target physiological site;
            a first chamber containing the first cathode and the first anode, wherein the first chamber defines at least one opening providing for entry and exit from the first chamber of the fluid; and
        a second battery structure comprising:
            a second cathode;
            a second anode, wherein the second cathode and the second anode are made from dissimilar materials selected to provide a voltage potential difference when the second cathode and the second anode contact the electrolyte; and
            a second chamber containing the second cathode and the second anode, wherein the second chamber defines at least one opening providing for entry and exit from the second chamber of the fluid; and
    a signal receiver configured to receive a signal produced by the IEM, wherein the receiver is sized to be stably associated with a living subject in a manner that does not substantially impact movement of said living subject.

2. The system according to claim 1, wherein the IEM composition comprises an integrated circuit that includes a signal generation element.

3. The system according to claim 2, wherein the IEM composition further comprises a solid support that includes the integrated circuit, and wherein the first and second battery structures are present on a surface of the solid support.

4. The system according to claim 1, wherein the signal receiver comprises at least one electrode.

5. The system according to claim 1, wherein the signal receiver comprises two electrodes.

6. The system according to claim 1, wherein the signal receiver further comprises a power generation element.

7. The system according to claim 1, wherein the signal receiver further comprises a data storage element.

8. The system according to claim 1, wherein the signal receiver further comprises a physiological sensor.

9. The system according to claim 8, wherein the physiological sensor is configured to provide data selected from the group consisting of respiration, heart rate, temperature and blood pressure.

10. The system according to claim 1, wherein the signal receiver comprises:
    first and second electrodes configured to receive a signal;
    a signal demodulator;
    a signal transmitter;
    a data storage element; and
    a power source.

11. The system according to claim 10, wherein the signal receiver comprises an integrated circuit that comprises at least one of the elements selected from the group consisting of:
    the first and second electrodes configured to receive a signal;
    the signal demodulator;
    the signal transmitter; and
    the data storage element.

12. The system according to claim 11, wherein the signal receiver further comprises a clock element.

13. The system according to claim 12, wherein the signal receiver further comprises a preamplifier.

14. The system according to claim 13, wherein the signal receiver further comprises a microprocessor.

15. The system according to claim 10, wherein the first and second electrodes are configured to receive a signal and to sense a biomarker.

16. The system according to claim 15, wherein the biomarker is selected from the group consisting of electrocardiogram, heart rate, respiration rate and fluid status.

17. The system according to claim 15, wherein the signal receiver further comprises a physiological sensor distinct from the first and second electrodes.

18. The system according to claim 17, wherein the physiological sensor distinct from the first and second electrodes is selected from the group consisting of temperature sensor, pressure sensor and analyte detector, motion sensor or a strain gauge.

19. The system according claim 1, wherein the system further comprises an external data receiver configured to receive data from the signal receiver.

20. The system according to claim 19, wherein the external data receiver further comprises at least one of a data storage element, a data processing element, a data display element, data transmission element, a notification mechanism, and a user interface.

21. The system according to claim 20, wherein the external data receiver is selected from the group consisting of a bedside monitor, a PDA, a cell phone and a PC.

22. An ingestible event marker (IEM) composition configured to emit a signal upon contact with a target physiological site and does not include an active agent, wherein the IEM comprises:
a first battery structure comprising:
a first cathode;
a first anode, wherein the first cathode and the first anode are made at least in part from dissimilar materials selected to provide a voltage potential difference when the first cathode and the first anode contact an electrolyte made up at least in part by fluid present at the target physiological site;
a first chamber containing the first cathode and the first anode, wherein the first chamber defines at least one opening providing for entry and exit from the first chamber of the fluid; and
a second battery structure comprising:
a second cathode;
a second anode, wherein the second cathode and the second anode are made from dissimilar materials selected to provide a voltage potential difference when the second cathode and the second anode contact the electrolyte; and
a second chamber containing the second cathode and the second anode, wherein the second chamber defines at least one opening providing for entry and exit from the second chamber of the fluid.

23. A signal receiver configured to receive a signal produced by an identifier of a pharmaceutical composition upon contact with a target physiological site and sized to be stably associated with a living subject in a manner that does not substantially impact movement of said living subject, wherein the identifier comprises:
a first battery structure comprising:
a first cathode;
a first anode, wherein the first cathode and the first anode are made at least in part from dissimilar materials selected to provide a voltage potential difference when the first cathode and the first anode contact an electrolyte made up at least in part by fluid present at the target physiological site;
a first chamber containing the first cathode and the first anode, wherein the first chamber defines at least one opening providing for entry and exit from the first chamber of the fluid; and
a second battery structure comprising:
a second cathode;
a second anode, wherein the second cathode and the second anode are made from dissimilar materials selected to provide a voltage potential difference when the second cathode and the second anode contact the electrolyte; and
a second chamber containing the second cathode and the second anode, wherein the second chamber defines at least one opening providing for entry and exit from the second chamber of the fluid.

24. A method comprising:
administering to a subject an ingestible event marker (IEM) configured to emit a signal upon contact with a target physiological site and does not include an active agent, wherein the IEM comprises:
a first battery structure comprising:
a first cathode;
a first anode, wherein the first cathode and the first anode are made at least in part from dissimilar materials selected to provide a voltage potential difference when the first cathode and the first anode contact an electrolyte made up at least in part by fluid present at the target physiological site;
a first chamber containing the first cathode and the first anode, wherein the first chamber defines at least one opening providing for entry and exit from the first chamber of the fluid; and
a second battery structure comprising:
a second cathode;
a second anode, wherein the second cathode and the second anode are made from dissimilar materials selected to provide a voltage potential difference when the second cathode and the second anode contact the electrolyte; and
a second chamber containing the second cathode and the second anode, wherein the second chamber defines at least one opening providing for entry and exit from the chamber of the fluid; and
detecting a signal emitted from said identifier with a signal receiver.

25. A kit comprising:
an ingestible event marker (IEM) configured to emit a signal upon contact with a target physiological site and does not include an active agent, wherein the IEM comprises:
a first battery structure comprising:
a first cathode;
a first anode, wherein the first cathode and the first anode are made at least in part from dissimilar materials selected to provide a voltage potential difference when the first cathode and the first anode contact an electrolyte made up at least in part by fluid present at the target physiological site;
a first chamber containing the first cathode and the first anode, wherein the first chamber defines at least one opening providing for entry and exit from the first chamber of the fluid; and
a second battery structure comprising:
a second cathode;
a second anode, wherein the second cathode and the second anode are made from dissimilar materials selected to provide a voltage potential difference when the second cathode and the second anode contact the electrolyte; and
a second chamber containing the second cathode and the second anode, wherein the second chamber defines at least one opening providing for entry and exit from the chamber of the fluid; and
a signal receiver.

* * * * *